(12) United States Patent
Rascon et al.

(10) Patent No.: US 12,043,667 B2
(45) Date of Patent: Jul. 23, 2024

(54) CLEC12A BINDING POLYPEPTIDES AND USES THEREOF

(71) Applicant: Inhibrx Biosciences, Inc., La Jolla, CA (US)

(72) Inventors: Lucas Rascon, San Diego, CA (US); Angelica Sanabria, La Jolla, CA (US); John C. Timmer, San Diego, CA (US); Brendan P. Eckelman, Encinitas, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 0 days.

(21) Appl. No.: 16/864,481

(22) Filed: May 1, 2020

(65) Prior Publication Data

US 2020/0347139 A1    Nov. 5, 2020

Related U.S. Application Data

(60) Provisional application No. 62/844,426, filed on May 7, 2019, provisional application No. 62/843,411, filed on May 4, 2019.

(51) Int. Cl.
| | |
|---|---|
| *C07K 16/28* | (2006.01) |
| *A61K 39/00* | (2006.01) |
| *C07K 16/46* | (2006.01) |
| *C12N 15/63* | (2006.01) |
| *A61K 45/06* | (2006.01) |

(52) U.S. Cl.
CPC ........ *C07K 16/2851* (2013.01); *C07K 16/468* (2013.01); *C12N 15/63* (2013.01); *A61K 2039/505* (2013.01); *A61K 45/06* (2013.01); *C07K 2317/24* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,871,753 A | 2/1999 | Crabtree et al. |
| 5,910,573 A | 6/1999 | Pluckthun et al. |
| 6,291,158 B1 | 9/2001 | Winter et al. |
| 6,291,161 B1 | 9/2001 | Lerner et al. |
| 6,423,498 B1 | 7/2002 | Markland et al. |
| 6,649,595 B2 | 11/2003 | Clackson et al. |
| 6,972,193 B1 | 12/2005 | Crabtree et al. |
| 9,587,020 B2 | 3/2017 | Wu et al. |
| 10,196,444 B2 | 2/2019 | Jarjour et al. |
| 10,287,354 B2 | 5/2019 | Broqdon et al. |
| 10,428,142 B2 | 10/2019 | Clackson et al. |
| 10,457,731 B2 | 10/2019 | Jariour et al. |
| 11,530,265 B2 | 12/2022 | Jariour et al. |
| 2007/0065431 A1 | 3/2007 | Coia et al. |
| 2011/0286980 A1 | 11/2011 | Brenner |
| 2012/0100160 A1 | 4/2012 | Lucas et al. |
| 2013/0287752 A1 | 10/2013 | Davila et al. |
| 2015/0266973 A1 | 9/2015 | Jariour et al. |
| 2016/0017302 A1 | 1/2016 | Dotti et al. |
| 2016/0051651 A1 | 2/2016 | Brogdon et al. |
| 2016/0185862 A1 | 6/2016 | Wu et al. |
| 2016/0311901 A1 | 10/2016 | Jarjour et al. |
| 2016/0318996 A1 | 11/2016 | Hollands et al. |
| 2018/0237533 A1 | 8/2018 | Cellectis |
| 2020/0071399 A1 | 3/2020 | Jarjour et al. |
| 2020/0347139 A1 | 11/2020 | Rascon et al. |

FOREIGN PATENT DOCUMENTS

| | | |
|---|---|---|
| CN | 101045926 A | 10/2007 |
| WO | WO-1999/036553 A2 | 7/1999 |
| WO | WO-1999/041258 A1 | 8/1999 |
| WO | WO-2006/072620 A1 | 7/2006 |
| WO | WO-2006/095164 A1 | 9/2006 |
| WO | WO-2007/098934 A1 | 9/2007 |
| WO | WO-2012/082841 A2 | 6/2012 |
| WO | 2014051433 A1 | 4/2014 |
| WO | WO-2014/127261 A1 | 8/2014 |
| WO | WO-2015/017214 A1 | 2/2015 |
| WO | WO-2015/150771 A1 | 10/2015 |
| WO | 2016014535 A1 | 1/2016 |
| WO | WO-2016/014553 A1 | 1/2016 |
| WO | 2016040868 A1 | 3/2016 |
| WO | 2016205200 A1 | 12/2016 |
| WO | 2017125897 A1 | 7/2017 |
| WO | WO-2017/180993 A1 | 10/2017 |
| WO | 2019055677 A1 | 3/2019 |
| WO | WO-2019/118895 A1 | 6/2019 |
| WO | WO-2019/188885 A1 | 10/2019 |
| WO | 2020052543 A1 | 3/2020 |
| WO | 2020113063 A1 | 6/2020 |
| WO | WO-2020/123933 A1 | 6/2020 |
| WO | WO-2020/123936 A1 | 6/2020 |
| WO | WO-2020/123938 A1 | 6/2020 |

(Continued)

OTHER PUBLICATIONS

Bannas et al., Front. Immunol., 8:1603 (2017). doi: 10.3389/fimmu.2017.01603.*
Ma et al., Journal of Hematology & Oncology, 12:41, 2019, https://doi.org/10.1186/s13045-019-0726-5.*
International Search Report and Written Opinion for International Application No. PCT/US2020/030970, dated Jul. 9, 2020, 13 pages.
International Search Report and Written Opinion for International Application No. PCT/US2020/31781 dated Oct. 9, 2020, 13 pages.
Invitation to Pay Fees for International Application No. PCT/US2020/031781, dated Aug. 14, 2020, 3 pages.
Dahlen et al., "Bispecific antibodies in cancer immunotherapy" Therapeutic Advances in Vaccines an Immunotherapy, vol. 6(1) 3-17 (2018).

(Continued)

*Primary Examiner* — Marianne P Allen
(74) *Attorney, Agent, or Firm* — McNeill Baur PLLC

(57) ABSTRACT

Provided herein are VHH-containing polypeptides that bind CLEC12a. Uses of the VHH-containing polypeptides are also provided.

27 Claims, 8 Drawing Sheets

Specification includes a Sequence Listing.

(56) References Cited

FOREIGN PATENT DOCUMENTS

| WO | WO-2020/123947 A1 | 6/2020 |
| WO | WO 2020/227073 | * 11/2020 |
| WO | WO 2020/227475 | * 11/2020 |
| WO | WO-2020/227481 A1 | 11/2020 |
| WO | WO-2021/067347 A1 | 4/2021 |
| WO | WO-2021/207613 A1 | 10/2021 |

OTHER PUBLICATIONS

Atilla et al., "Optimizing C-Type Lectin-like Molecule 1 (CLL-1) Directed CAR T Cell Therapy of Acute Myeloid Leukemia" Abstracts/ Biol Blood Marro Transplant 25, S100-S289; pp. S167-S168 (2019).
Tashiro et al., "Treatment of Acute Myeloid Leukemia with T Cells Expressing Chimeric Antigen Receptors Directed to C-type Lectin-like Molecule 1" Molecular Therapy, vol. 25, No. 9, pp. 2202-2213 (2017).
Muyldermans, S., "Nanobodies: Natural Single-Domain Antibodies," Annual Review of Biochemistry, vol. 82, No. 1, pp. 775-797 (2013).
Vincke et al., "Generation of Single Domain Antibody Fragments Derived from Camelids and Generation of Manifold Constructs Ed," Methods in Molecular Biology, Humana PR, US, vol. 907, pp. 145-176, (2012).
Abate-Daga et al., CAR models: next-generation CAR modifications for enhanced T-cell function. Mol Ther Oncolytics. May 18, 2016;3:16014, 7 pages.
Alder et al., Antibody responses of variable lymphocyte receptors in the lamprey. Nat Immunol. Mar. 2008;9(3):319-27.
Banaszynski et al., Characterization of the FKBP-Rapamycin-FRB Ternary Complex. J Am Chem Soc. 2005;127(13):4715-4721.
Baral et al., Experimental therapy of African trypanosomiasis with a nanobody-conjugated human trypanolytic factor. Nat Med. May 2006; 12(5):580-4.
Barthelemy et al., Comprehensive analysis of the factors contributing to the stability and solubility of autonomous human VH domains. J Biol Chem. Feb. 8, 2008;283(6):3639-3654.
Bayle et al., Rapamycin analogs with differential binding specificity permit orthogonal control of protein activity. Chem Biol. Jan. 2006;13(1):99-107.
Beavil et al., Alpha-helical coiled-coil stalks in the low-affinity receptor for IgE (Fc epsilon RII/CD23) and related C-type lectins. Proc Natl Acad Sci US A. Jan. 15, 1992;89(2):753-7.
Belshaw et al., Controlling protein association and subcellular localization with a synthetic ligand that induces heterodimerization of proteins. Proc Natl Acad Sci U S A. May 14, 1996;93(10):4604-7.
Beste et al., Small antibody-like proteins with prescribed ligand specificities derived from the lipocalin fold. Proc Natl Acad Sci US A. Mar. 2, 1999;96(5):1898-903.
Binz et al., Designing repeat proteins: well-expressed, soluble and stable proteins from combinatorial libraries of consensus ankyrin repeat proteins. J Mol Biol. Sep. 12, 2003;332(2):489-503.
Binz et al., Engineering novel binding proteins from nonimmunoglobulin domains. Nat Biotechnol. Oct. 2005;23(10):1257-68.
Brentjens et al., CD19-targeted T cells rapidly induce molecular remissions in adults with chemotherapy-refractory acute lymphoblastic leukemia. Sci Transl Med. Mar. 20, 2013;5(177):177ra38; pp. 1-19.
Brentjens et al., Safety and persistence of adoptively transferred autologous CD19-targeted T cells in patients with relapsed or chemotherapy refractory B-cell leukemias. Blood. Nov. 3, 2011;118(18):4817-28.
Brown et al., A mammalian protein targeted by G1-arresting rapamycin-receptor complex. Nature. Jun. 30, 1994;369(6483) :756-8.
Capon et al. Designing CD4 immunoadhesins for AIDS therapy. Nature. Feb. 9, 1989;337(6207):525-31.
Carpenito et al., Control of large, established tumor xenografts with genetically retargeted human T cells containing CD28 and CD137 domains. Proc Natl Acad Sci US A. Mar. 3, 2009;106(9):3360-5.

Challita et al., Multiple modifications in cis elements of the long terminal repeat of retroviral vectors lead to increased expression and decreased DNA methylation in embryonic carcinoma cells. J Virol. Feb. 1995;69(2):748-55.
Cortez-Retamozo et al., Efficient cancer therapy with a nanobody-based conjugate. Cancer Res. Apr. 15, 2004;64(8):2853-7.
Craik et al., Plant cyclotides: A unique family of cyclic and knotted proteins that defines the cyclic cystine knot structural motif. J Mol Biol. Dec. 17, 1999;294(5):1327-36.
Curran et al., Chimeric antigen receptors for T cell immunotherapy: current understanding and future directions. J Gene Med. Jun. 2012;14(6):405-15.
Donnelly et al., The 'cleavage' activities of foot-and-mouth disease virus 2A site-directed mutants and naturally occurring '2A-like' sequences. J Gen Virol. May 2001;82(Pt 5):1027-1041.
Dotti et al., Design and development of therapies using chimeric antigen receptor- exoressina T cells. Immunol Rev. Jan. 2014;257(1):107-26.
Duong et al., Enhancing the specificity of T-cell cultures for adoptive immunotherapy of cancer. Immunotherapy_ Jan. 2011;3(1):33-48.
Fegan et al., Chemically controlled protein assembly: techniques and applications. Chem Rev. Jun. 9, 2010;110(6):3315-36.
Ghahroudi et al., Selection and identification of single domain antibody fragments from camel heavy-chain antibodies. FEBS Lett. Sep. 15, 1997;414(3):521-6.
Grunberg et al., Building blocks for protein interaction devices. Nucleic Acids Res. May 2010;38(8):2645-62.
Grupp et al., Chimeric antigen receptor-modified T cells for acute lymphoid leukemia. N Engl J Med. Apr. 18, 2013;368(16):1509-1518.
Hackel et al., Picomolar affinity fibronectin domains engineered utilizing loop length diversity, recursive mutagenesis, and loop shuffling. J Mol Biol. Sep. 19, 2008;381(5):1238-52.
Hamers-Casterman et al., Naturally occurring antibodies devoid of light chains. Nature. Jun. 3, 1993;363(6428):446-8.
Herrin et al., Structure and specificity of lamprey monoclonal antibodies. Proc Natl Acad Sci US A. Feb. 12, 2008;105(6):2040-5.
Hoet et al., Generation of high-affinity human antibodies by combining donor-derived and synthetic comolementarity-determining-region diversity. Nat Biotechnol. Mar. 2005;23(3):344-8.
Hsu et al., Primary human T lymphocytes engineered with a codon-optimized IL-15 gene resist cytokine withdrawal-induced apoptosis and persist long-term in the absence of exogenous cytokine. J Immunol. Dec. 1, 2005;175(11):7226-34.
Hu et al., Minibody: A novel engineered anti-carcinoembryonic antigen antibody fragment (single-chain Fv-CH3) which exhibits rapid, high-level targeting of xenografts. Cancer Res. Jul. 1, 1996;56(13):3055-61.
Huang et al., Scorpion-toxin mimics of CD4 in complex with human immunodeficiency virus gp120 crystal structures, molecular mimicry, and neutralization breadth. Structure. May 2005; 13(5):755-68.
Irion et al., Identification and targeting of the ROSA26 locus in human embryonic stem cells Nat Biotechnol. Dec. 2007;25(12):1477-82.
Janeway et al., Immunobiology: The Immune System in Health and Disease, 4th Edition. Current Biology Publications. pp. 148, 149 and 172 (1999).
Jespers et al., Aggregation-resistant domain antibodies selected on phage by heat denaturation. Nat Biotechnol. Sep. 2004;22(9):1161-5.
June et al., T-cell therapy at the threshold. Nat Biotechnol. Jul. 10, 2012;30(7):611-4.
Kalos et al., T cells with chimeric antigen receptors have potent antitumor effects and can establish memory in patients with advanced leukemia. Sci Transl Med. Aug. 10, 2011;3(95):95ra73; pp. 1-21.
Kay. Structure-function relationships in the FK506-binding protein (FKBP) family of peptidylprolyl cis-trans isomerases. Biochem J. Mar. 1, 1996;314 ( Pt 2)(Pt 2):361-85.
Klemm et al., Dimerization as a regulatory mechanism in signal transduction. Annu Rev Immunol. 1998;16:569-92.

(56) References Cited

OTHER PUBLICATIONS

Kochenderfer et al., B-cell depletion and remissions of malignancy along with cytokine-associated toxicity in a clinical trial of anti-CD19 chimeric-antigen-receptor-transduced T cells. Blood. Mar. 22, 2012;119(12):2709-20.
Kochenderfer et al., Treating B-cell cancer with T cells expressing anti-CD19 chimeric antigen receptors. Nat Rev Clin Oncol. May 2013;10(5):267-76.
Kowolik et al., D28 costimulation provided through a CD19-specific chimeric antigen receptor enhances in vivo persistence and antitumor efficacy of adoptively transferred T cells. Cancer Res. Nov. 15, 2006;66(22):10995-1004.
Lee et al., Design of a binding scaffold based on variable lymphocyte receptors of jawless vertebrates by module engineering. Proc Natl Acad Sci US A. Feb. 28, 2012;109(9):3299-304.
Leung et al., Small Molecule-Regulated Antigen Recognition System for Inducible T Cell Targeting of CAncer Cells. Mol Ther. 2016;24:S110, Abstract No. 277; 1 page.
Main et al., Design of stable alpha-helical arrays from an idealized TPR motif. Structure. May 2003; 11(5):497-508.
Manzke et al., CD3X anti-nitrophenyl bispecific diabodies: universal immunotherapeutic tools for retargeting T cells to tumors. Int J Cancer. Aug. 27, 1999;82(5):700-8.
Martin et al., Rational design of a CD4 mimic that inhibits HIV-1 entry and exposes cryptic neutralization epitopes. Nat Biotechnol. Jan. 2003;21(1):71-6.
Milone et al., Chimeric receptors containing CD137 signal transduction domains mediate enhanced survival of T cells and increased antileukemic efficacy in vivo. Mol Ther. Aug. 2009;17(8):1453-64.
Nguyen et al., Heavy-chain antibodies in Camelidae; a case of evolutionary innovation. Immunogenetics. Apr. 2002;54(1):39-47.
Nguyen et al., The specific variable domain of camel heavy-chain antibodies is encoded in the qermline. J Mol Biol. Jan. 23, 1998;275(3):413-8.
Nord et al., A combinatorial library of an alpha-helical bacterial receptor domain. Protein Eng. Jun. 1995;8(6):601-8.
Nord et al., Binding proteins selected from combinatorial libraries of an alpha-helical bacterial receptor domain. Nat Biotechnol. Aug. 1997; 15(8):772-7.
Nord et al., Recombinant human factor VIII-specific affinity ligands selected from phage- displayed combinatorial libraries of protein A. Eur J Biochem. Aug. 2001;268(15):4269-77.
Parker et al., Antibody mimics based on human fibronectin type three domain engineered for thermostability and high-affinity binding to vascular endothelial growth factor receptor two. Protein Enq Des Sel. Sep. 2005;18(9):435-44.
Pule et al., A chimeric T cell antigen receptor that augments cytokine release and supports clonal expansion of primary human T cells. Mol Ther. Nov. 2005;12(5):933-41.
Quintarelli et al., Co-expression of cytokine and suicide genes to enhance the activity and safety of tumor-specific cytotoxic T lymphocytes. Blood. Oct. 15, 2007;110(8):2793-802.
Restifo et al., Adoptive immunotherapy for cancer: harnessing the T cell response. Nat Rev Immunol. Mar. 22, 2012;12(4):269-81.

Richards et al., Engineered fibronectin type III domain with a RGDWXE sequence binds with enhanced affinity and specificity to human alphavbeta3 integrin. J Mol Biol. Mar. 7, 2003;326(5):1475-88.
Roux et al., Structural analysis of the nurse shark (new) antigen receptor (NAR): molecular convergence of NAR and unusual mammalian immunoglobulins. Proc Natl Acad Sci U S A. Sep. 29, 1998;95(20):11804-9.
Ryan et al., Virus-encoded proteinases of the picornavirus supergroup. J Gen Virol. Apr. 1997;78 ( Pt 4):699-723.
Sato et al., Genes encoding putative natural killer cell C-type lectin receptors in teleostean fishes. Proc Natl Acad Sci US A. Jun. 24, 2003;100(13):7779-84.
Schlessinger. Cell signaling by receptor tyrosine kinases. Cell. Oct. 13, 2000;103(2):211-25.
Schonfeld et al., An engineered lipocalin specific for CTLA-4 reveals a combining site with structural and conformational features similar to antibodies. Proc Natl Acad Sci U S A. May 19, 2009;106(20):8198-203.
Skerra, Alternative binding proteins: anticalins - harnessing the structural plasticity of the lipocalin ligand pocket to engineer novel binding activities. Febs J. Jun. 2008;275(11):2677-83.
Spencer et al., Controlling signal transduction with synthetic ligands. Science. Nov. 12, 1993;262(5136):1019-24.
Standaert et al., Molecular cloning and overexpression of the human FK506-binding protein FKBP. Nature. Aug. 16, 1990;346(6285): 671-4.
Stephan et al., T cell-encoded CD80 and 4-1BBL induce auto- and transcostimulation, resulting in potent tumor rejection. Nat Med. Dec. 2007;13(12):1440-9.
Stumpp et al., Designing repeat proteins: modular leucine-rich repeat protein libraries based on the mammalian ribonuclease inhibitor family. J Mol Biol. Sep. 12, 2003;332(2):471-87.
Tal et al., An NCR1-based chimeric receptor endows T-cells with multiple anti-tumor specificities. Oncotarget. Nov. 15, 2014;5(21):10949-58.
Till et al., CD20-specific adoptive immunotherapy for lymphoma using a chimeric antigen receptor with both CD28 and 4-1BB domains: pilot clinical trial results. Blood. Apr. 26, 2012;119(17):3940-50.
Varadamsetty et al., Designed Armadillo repeat proteins: library generation, characterization and selection of peptide binders with high specificity. J Mol Biol. Nov. 23, 2012;424(1-2):68-87.
Vincke et al., General strategy to humanize a camelid single-domain antibody and identification of a universal humanized nanobody scaffold. J Biol Chem. Jan. 30, 2009;284(5) :3273-3284.
Vita et al., Scorpion toxins as natural scaffolds for protein engineering. Proc Natl Acad Sci U SA. Jul. 3, 1995;92(14):6404-8.
Weisel et al., A model for fibrinogen: domains and sequence. Science. Dec. 20, 1985;230(4732):1388-91.
White et al., Comparison of the glycosyl-phosphatidylinositol cleavage/attachment site between mammalian cells and parasitic protozoa. J Cell Sci. Feb. 2000;113 ( Pt 4):721-7.
Wilkie et al., Dual targeting of ErbB2 and MUC1 in breast cancer using chimeric antigen receptors engineered to provide complementary signaling. J Clin Immunol. Oct. 2012;32(5):1059-70.
Zelensky et al., The C-type lectin-like domain superfamily. Febs J. Dec. 2005;272(24):6179-217.

* cited by examiner

CLEC12A BINDING POLYPEPTIDES AND USES THEREOF

CROSS-REFERENCE TO RELATED APPLICATIONS

This application claims the benefit of priority of U.S. Provisional Application No. 62/843,411, filed May 4, 2019, and U.S. Provisional Application No. 62/844,426, filed May 7, 2019, each of which is incorporated by reference herein in its entirety for any purpose.

SEQUENCE LISTING

This application contains a Sequence Listing submitted in electronic format. The Sequence Listing is provided as a file entitled "2020-05-01_01202-0023-00US_Sequence_ Listing_ST25" created on Apr. 28, 2020, which is 116,241 bytes in size. The information in the electronic format of the sequence listing is incorporated herein by reference in its entirety.

FIELD

The present invention relates to CLEC12a-binding polypeptides, and methods of using CLEC12a-binding polypeptides to modulate the biological activity of CLEC12a. Such methods include, but are not limited to, methods of treating cancer.

BACKGROUND

CLEC12a, also known as CLL-1, CLL1, DCAL-2, MICL, CD371, or C-type lectin domain family 12 member A, is a member of the C-type lectin/C-type lectin-like domain (CTL/CTLD) superfamily and regulates myeloid cell activation. CLEC12a is also a marker of blasts and leukemic stem cells in patients with acute myeloid leukemia (AML). Further, CLEC12a has been used to detect minimal residual disease in patients after treatment for AML. Therefore, there exists a therapeutic need for more potent treatments for CLEC12a-expressing cancers.

SUMMARY

Provided herein are CLEC12a-binding polypeptides and methods of using CLEC12a-binding polypeptides to treat, for example, leukemia. In some embodiments, a CLEC12a-binding polypeptide comprises at least one VHH domain. Some embodiments are provided below.

Embodiment 1

A polypeptide comprising at least one VHH domain that binds CLEC12a and that comprises a CDR1 comprising the amino acid sequence of SEQ ID NO: 47, 32, 3, 7, 11, 15, 19, 23, 35, 38, 41, or 44; a CDR2 comprising the amino acid sequence of SEQ ID NO: 48, 33, 4, 8, 12, 16, 20, 24, 36, 39, 42, or 45; and a CDR3 comprising the amino acid sequence of SEQ ID NO: 49, 34, 5, 9, 13, 17, 21, 25, 37, 40, 43, or 46.

Embodiment 2

The polypeptide of embodiment 1, wherein at least one VHH domain comprises a CDR1 comprising the amino acid sequence of SEQ ID NO: 47 or 23; a CDR2 comprising the amino acid sequence of SEQ ID NO: 48 or 24; and a CDR3 comprising the amino acid sequence of SEQ ID NO: 49 or 25.

Embodiment 3

The polypeptide of embodiment 1 or embodiment 2, wherein at least one VHH domain comprises a CDR1 comprising the amino acid sequence of SEQ ID NO: 32 or 3; a CDR2 comprising the amino acid sequence of SEQ ID NO: 33 or 4; and a CDR3 comprising the amino acid sequence of SEQ ID NO: 34 or 5.

Embodiment 4

The polypeptide of any one of embodiments 1-3, wherein at least one VHH domain comprises a CDR1 comprising the amino acid sequence of SEQ ID NO: 7 or 35; a CDR2 comprising the amino acid sequence of SEQ ID NO: 8 or 36; and a CDR3 comprising the amino acid sequence of SEQ ID NO: 9 or 37.

Embodiment 5

The polypeptide of any one of embodiments 1-4, wherein at least one VHH domain comprises a CDR1 comprising the amino acid sequence of SEQ ID NO: 11 or 38; a CDR2 comprising the amino acid sequence of SEQ ID NO: 12 or 39; and a CDR3 comprising the amino acid sequence of SEQ ID NO: 13 or 40.

Embodiment 6

The polypeptide of any one of embodiments 1-5, wherein at least one VHH domain comprises a CDR1 comprising the amino acid sequence of SEQ ID NO: 15 or 41; a CDR2 comprising the amino acid sequence of SEQ ID NO: 16 or 42; and a CDR3 comprising the amino acid sequence of SEQ ID NO: 17 or 43.

Embodiment 7

The polypeptide of any one of embodiments 1-6, wherein at least one VHH domain comprises a CDR1 comprising the amino acid sequence of SEQ ID NO: 19 or 44; a CDR2 comprising the amino acid sequence of SEQ ID NO: 20 or 45; and a CDR3 comprising the amino acid sequence of SEQ ID NO: 21 or 46.

Embodiment 8

The polypeptide of any one of embodiments 1-7, wherein at least one VHH domain comprises a CDR1, a CDR2, and a CDR3, respectively comprising the amino acid sequences of SEQ ID NOs: 32, 33, and 34; SEQ ID NOs: 47, 48, and 49; SEQ ID NOs: 3, 4, and 5; SEQ ID NOs: 7, 8, and 9; SEQ ID NOs: 11, 12, and 13; SEQ ID NOs: 15, 16, and 17; SEQ ID NOs: 19, 20, and 21; SEQ ID NOs: 23, 24, and 25; SEQ ID NOs: 35, 36, and 37; SEQ ID NOs: 38, 39, and 40; SEQ ID NOs: 41, 42, and 43; SEQ ID NOs: 44, 45, and 46.

Embodiment 9

The polypeptide of any one of embodiments 1-8, wherein at least one VHH domain is humanized.

Embodiment 10

The polypeptide of any one of embodiments 1-9, wherein at least one VHH domain comprises an amino acid sequence at least 85%, at least 90%, at least 95%, or at least 99% identical to the amino acid sequence of SEQ ID NO: 26, 94, 31, 99, 27, 28, 29, 30, 95, 96, 97, or 98.

Embodiment 11

The polypeptide of any one of embodiments 1-9, wherein at least one VHH domain comprises the amino acid sequence of SEQ ID NO: 26, 94, 31, 99, 27, 28, 29, 30, 95, 96, 97, or 98.

Embodiment 12

The polypeptide of any one of embodiment 1-8, wherein at least one VHH domain comprises an amino acid sequence at least 85%, at least 90%, at least 95%, or at least 99% identical to the amino acid sequence of SEQ ID NO: 2, 6, 10, 14, 18, 22, 88, 89, 90, 91, 92, or 93.

Embodiment 13

The polypeptide of any one of embodiments 1-8, wherein at least one VHH domain comprises the amino acid sequence of SEQ ID NO: 2, 6, 10, 14, 18, 22, 88, 89, 90, 91, 92, or 93.

Embodiment 14

The polypeptide of any one of embodiments 1-13, comprising two VHH domains.

Embodiment 15

The polypeptide of any one of embodiments 1-13, comprising three VHH domains.

Embodiment 16

The polypeptide of any one of embodiments 1-15, wherein the polypeptide comprises at least one binding domain that binds an antigen other than CLEC12a.

Embodiment 17

The polypeptide of embodiment 16, wherein the polypeptide comprises at least one binding domain that binds CD3, T-cell receptor (TCR) α, TCRβ, CD28, CD16, CD32A, CD64, CD89, NKp46, or NKG2D.

Embodiment 18

The polypeptide of embodiment 14 or 15, wherein each VHH domain binds CLEC12a.

Embodiment 19

The polypeptide of embodiment 18, wherein each VHH domain comprises the same CDR1, CDR2, and CDR3 amino acid sequences.

Embodiment 20

The polypeptide of embodiment 18, wherein each VHH domain comprises the same VHH sequence.

Embodiment 21

The polypeptide of any one of embodiments 1-13, comprising one VHH domain.

Embodiment 22

The polypeptide of any one of embodiments 1-21, wherein the polypeptide comprises an Fc region.

Embodiment 23

The polypeptide of embodiment 22, wherein the Fc region comprises an amino acid sequence selected from SEQ ID NOs: 50 to 85.

Embodiment 24

The polypeptide of embodiment 22 or embodiment 23, which forms a dimer under physiological conditions.

Embodiment 25

The polypeptide of any one of embodiments 1-24, wherein the CLEC12a is human CLEC12a.

Embodiment 26

The polypeptide of embodiment 25, wherein the human CLEC12a comprises the sequence of SEQ ID NO: 1.

Embodiment 27

An immunoconjugate comprising the polypeptide of any one of embodiments 1-26 and a cytotoxic agent.

Embodiment 28

The immunoconjugate of embodiment 27, wherein the cytotoxic agent is selected from a calicheamicin, an auristatin, a dolastatin, a tubulicin, a maytansinoid, a cryptophycin, a duocarmycin, an esperamicin, a pyrrolobenzodiazepine, and an enediyne antibiotic.

Embodiment 29

A pharmaceutical composition comprising the polypeptide of any one of embodiments 1-26 or the immunoconjugate of embodiment 27 or embodiment 28, and a pharmaceutically acceptable carrier.

Embodiment 30

An isolated nucleic acid that encodes the polypeptide of any one of embodiments 1-26.

Embodiment 31

A vector comprising the nucleic acid of embodiment 30.

Embodiment 32

A host cell comprising the nucleic acid of embodiment 34 or the vector of embodiment 31.

Embodiment 33

A host cell that expresses the polypeptide of any one of embodiments 1-26.

Embodiment 34

A method of producing the polypeptide of any one of embodiments 1-26, comprising incubating the host cell of embodiment 32 or embodiment 33 under conditions suitable for expression of the polypeptide.

Embodiment 35

The method of embodiment 34, further comprising isolating the polypeptide.

Embodiment 36

A method of treating cancer comprising administering to a subject with cancer a pharmaceutically effective amount of the polypeptide of any one of embodiments 1-26, the immunoconjugate of embodiment 27 or embodiment 28, or the pharmaceutical composition of embodiment 29.

Embodiment 37

The method of embodiment 36, wherein the cancer is selected from lymphoma; Hodgkin's lymphoma; non-Hodgkin's lymphoma; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; chronic lymphocytic leukemia (CLL); acute lymphoblastic leukemia (ALL); acute myeloid leukemia (AML); Hairy cell leukemia; and chronic myeloblastic leukemia.

Embodiment 38

The method of embodiment 36 or 37, wherein the cancer is acute myeloid leukemia (AML).

Embodiment 39

The method of any one of embodiments 36-38, further comprising administering an additional therapeutic agent.

Embodiment 40

The method of embodiment 39, wherein the additional therapeutic agent is an anti-cancer agent.

Embodiment 41

The method of embodiment 40, wherein the anti-cancer agent is selected from a chemotherapeutic agent, an anti-cancer biologic, radiation therapy, CAR-T therapy, and an oncolytic virus.

Embodiment 42

The method of any one of embodiments 36-39, wherein the cancer is a CLEC12a-expressing cancer.

BRIEF DESCRIPTION OF THE FIGURES

FIGS. 1A and 1B show Bio-Layer Interferometry data for polypeptides comprising a VHH domain that binds CLEC12a. FIG. 1A shows Bio-Layer Interferometry data for hzMB11v13 compared to other CLEC12a-binding sdAbs described herein. FIG. 1B shows Bio-Layer Interferometry data for hzME06v16 compared to other CLEC12a-binding sdAbs described herein.

FIG. 2A shows binding of MB11-IgG1 to CLEC12a. FIG. 2B shows binding of hzMB11v13-IgG1 to CLEC12a. FIG. 2C shows binding of ME06-IgG1 to CLEC12a. FIG. 2D shows binding of hzME06v16-IgG1 to CLEC12a. FIG. 2E shows binding of MC02-IgG1 to CLEC12a. FIG. 2F shows binding of hzMC02v6-IgG1 to CLEC12a. FIG. 2G shows binding of MH07-IgG1 to CLEC12a. FIG. 2H shows binding of hzMH07v3-IgG1 to CLEC12a. FIG. 2I shows binding of MC06-IgG1 to CLEC12a. FIG. 2J shows binding of hzMC06v2-IgG1 to CLEC12a. FIG. 2K shows binding of ME02-IgG1 to CLEC12a. FIG. 2L shows binding of hzME02v4-IgG1 to CLEC12a.

DETAILED DESCRIPTION

Figure 1A:
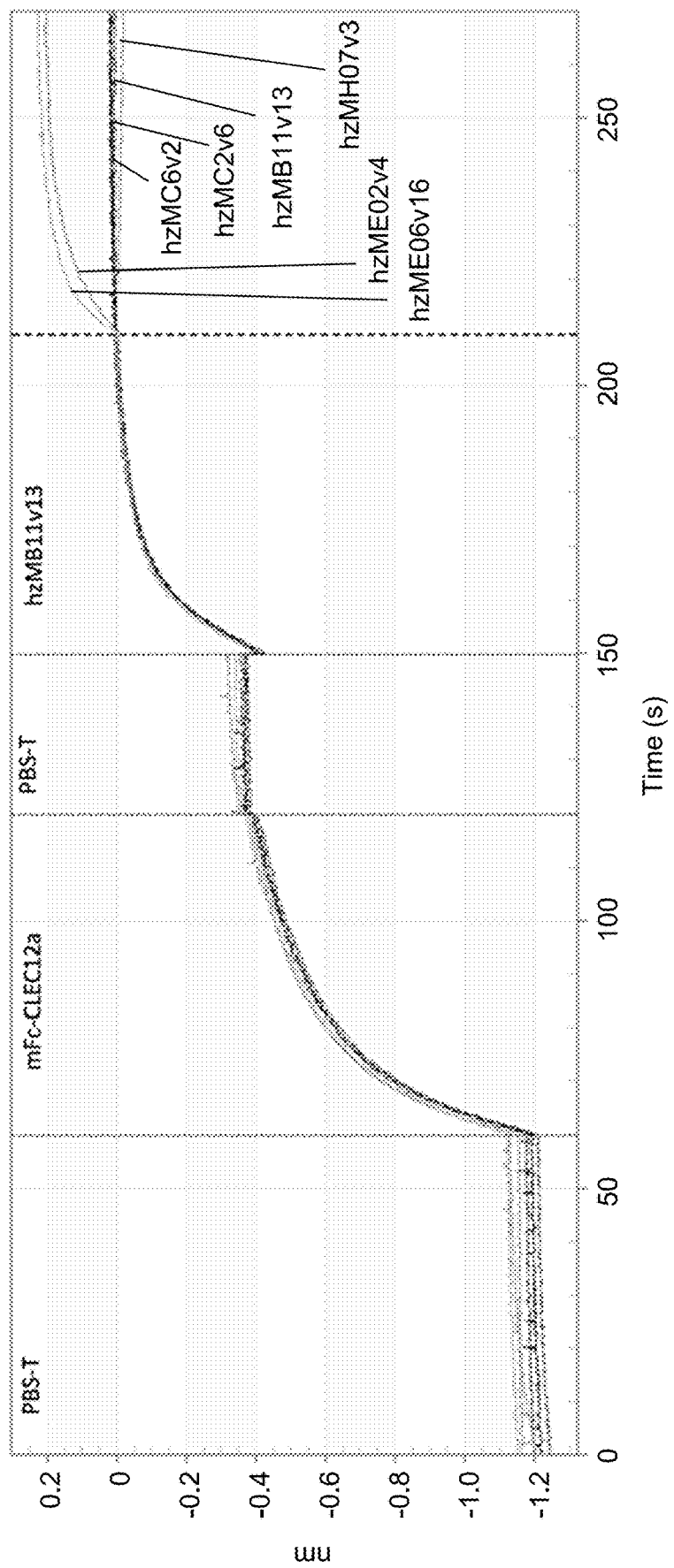

Embodiments provided herein relate to CLEC12a-binding polypeptides and their use in various methods of treating cancer.

Definitions and Various Embodiments

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

In general, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991). The "EU index as in Kabat" refers to the residue numbering of the human IgG1 EU antibody.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The phrase "reference sample", "reference cell", or "reference tissue", denote a sample with at least one known characteristic that can be used as a comparison to a sample with at least one unknown characteristic. In some embodiments, a reference sample can be used as a positive or negative indicator. A reference sample can be used to establish a level of protein and/or mRNA that is present in, for example, healthy tissue, in contrast to a level of protein and/or mRNA present in the sample with unknown characteristics. In some embodiments, the reference sample comes from the same subject, but is from a different part of the subject than that being tested. In some embodiments, the reference sample is from a tissue area surrounding or adjacent to the cancer. In some embodiments, the reference sample is not from the subject being tested, but is a sample from a subject known to have, or not to have, a disorder in question (for example, a particular cancer or CLEC12a-related disorder). In some embodiments, the reference sample is from the same subject, but from a point in time before the subject developed cancer. In some embodiments, the reference sample is from a benign cancer sample, from the same or a different subject. When a negative reference sample is used for comparison, the level of expression or amount of the molecule in question in the negative reference sample will indicate a level at which one of skill in the art will appreciate, given the present disclosure, that there is no and/or a low level of the molecule. When a positive reference sample is used for comparison, the level of expression or amount of the molecule in question in the positive reference sample will indicate a level at which one of skill in the art will appreciate, given the present disclosure, that there is a level of the molecule.

The terms "benefit", "clinical benefit", "responsiveness", and "therapeutic responsiveness" as used herein in the context of benefiting from or responding to administration of a therapeutic agent, can be measured by assessing various endpoints, e.g., inhibition, to some extent, of disease progression, including slowing down and complete arrest; reduction in the number of disease episodes and/or symptoms; reduction in lesion size; inhibition (that is, reduction, slowing down or complete stopping) of disease cell infiltration into adjacent peripheral organs and/or tissues; inhibition (that is, reduction, slowing down or complete stopping) of disease spread; relief, to some extent, of one or more symptoms associated with the disorder; increase in the length of disease-free presentation following treatment, for example, progression-free survival; increased overall survival; higher response rate; and/or decreased mortality at a given point of time following treatment. A subject or cancer that is "non-responsive" or "fails to respond" is one that has failed to meet the above noted qualifications to be "responsive".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides comprised in the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"CLEC12a" as used herein refers to any native, mature CLEC12a that results from processing of a CLEC12a precursor in a cell. The term includes CLEC12a from any vertebrate source, including mammals such as primates (e.g., humans and cynomolgus or rhesus monkeys) and rodents (e.g., mice and rats), unless otherwise indicated. The term also includes naturally-occurring variants of CLEC12a, such as splice variants or allelic variants. A nonlimiting exemplary human CLEC12a amino acid sequence is shown, e.g., in UniProt Accession No. Q5QGZ9.3. See SEQ ID NO. 1.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to a CLEC12a epitope is a sdAb or VHH-containing polypeptide that binds this epitope with greater affinity, avidity, more readily, and/or with greater duration than it binds to other CLEC12a epitopes or non-CLEC12a epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 10% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time. As used herein, the term "inhibit" with regard to the activity of CLEC12a refers to a decrease in an activity of CLEC12a, such as binding to monosodium urate. In some embodiments, "inhibit" refers to a decrease in a CLEC12a activity compared to the CLEC12a activity in the absence of the modulator. In some embodiments, a CLEC12a-binding polypeptide inhibits binding of CLEC12a to monosodium urate.

As used herein, the term "epitope" refers to a site on a target molecule (for example, an antigen, such as a protein, nucleic acid, carbohydrate or lipid) to which an antigen-binding molecule (for example, a sdAb or VHH-containing polypeptide) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between a residue of the antigen-binding molecule and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antigen-binding molecule. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antigen-binding molecule specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antigen-binding molecule specific to the epitope binds. It is noted that, in some embodiments, not every one of the residues within the linear epitope need be directly bound (or involved in a bond) by the antigen-binding molecule. In some embodiments, linear epitopes can be from immunizations with a peptide that effectively consisted of the sequence of the linear epitope, or from structural sections of a protein that are relatively isolated from the remainder of the protein (such that the antigen-binding molecule can interact, at least primarily), just with that sequence section.

The term "antibody" is used in the broadest sense and encompass various polypeptides that comprise antibody-like antigen-binding domains, including but not limited to conventional antibodies (typically comprising at least one heavy chain and at least one light chain), single-domain antibodies (sdAbs, comprising at least one VHH domain and an Fc region), VHH-containing polypeptides (polypeptides comprising at least one VHH domain), and fragments of any of the foregoing so long as they exhibit the desired antigen-binding activity. In some embodiments, an antibody comprises a dimerization domain. Such dimerization domains include, but are not limited to, heavy chain constant domains (comprising CH1, hinge, CH2, and CH3, where CH1 typically pairs with a light chain constant domain, CL, while the hinge mediates dimerization) and Fc regions (comprising hinge, CH2, and CH3, where the hinge mediates dimerization).

The term antibody also includes, but is not limited to, chimeric antibodies, humanized antibodies, and antibodies of various species such as camelid (including llama), shark, mouse, human, cynomolgus monkey, etc.

The term "antigen-binding domain" as used herein refers to a portion of an antibody sufficient to bind antigen. In some embodiments, an antigen binding domain of a conventional antibody comprises three heavy chain CDRs and three light chain CDRs. Thus, in some embodiments, an antigen binding domain comprises a heavy chain variable region comprising CDR1-FR2-CDR2-FR3-CDR3, and any portions of FR1 and/or FR4 required to maintain binding to antigen, and a light chain variable region comprising CDR1-FR2-CDR2-FR3-CDR3, and any portions of FR1 and/or FR4 required to maintain binding to antigen. In some embodiments, an antigen-binding domain of an sdAb or VHH-containing polypeptide comprises three CDRs of a VHH domain. Thus, in some embodiments, an antigen binding domain of an sdAb or VHH-containing polypeptide comprises a VHH domain comprising CDR1-FR2-CDR2-FR3-CDR3, and any portions of FR1 and/or FR4 required to maintain binding to antigen.

The term "VHH" or "VHH domain" or "VHH antigen-binding domain" as used herein refers to the antigen-binding portion of a single-domain antibody, such as a camelid antibody or shark antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprises only a partial FR1 and/or FR4, or lacks one or both of those framework regions, so long as the VHH substantially maintains antigen binding and specificity.

The terms "single domain antibody" and "sdAb" are used interchangeably herein to refer to an antibody comprising at least one monomeric domain, such as a VHH domain, without a light chain, and an Fc region. In some embodiments, an sdAb is a dimer of two polypeptides wherein each polypeptide comprises at least one VHH domain and an Fc region. As used herein, the terms "single domain antibody" and "sdAb" encompass polypeptides that comprise multiple VHH domains, such as a polypeptide having the structure $VHH_1$-$VHH_2$-Fc or $VHH_1$-$VHH_2$-$VHH_3$-Fc, wherein $VHH_1$, $VHH_2$, and $VHH_3$ may be the same or different.

The term "VHH-containing polypeptide" refers to a polypeptide that comprises at least one VHH domain. In some embodiments, a VHH polypeptide comprises two, three, or four or more VHH domains, wherein each VHH domain may be the same or different. In some embodiments, a VHH-containing polypeptide comprises an Fc region. In some such embodiments, the VHH-containing polypeptide may be referred to as an sdAb. Further, in some such embodiments, the VHH polypeptide may form a dimer. Nonlimiting structures of VHH-containing polypeptides, which are also sdAbs, include $VHH_1$-Fc, $VHH_1$-$VHH_2$-Fc, and $VHH_1$-$VHH_2$-$VHH_3$-Fc, wherein $VHH_1$, $VHH_2$, and $VHH_3$ may be the same or different. In some embodiments of such structures, one VHH may be connected to another VHH by a linker, or one VHH may be connected to the Fc by a linker. In some such embodiments, the linker comprises 1-20 amino acids, preferably 1-20 amino acids predominantly composed of glycine and, optionally, serine. In some embodiments, when a VHH-containing polypeptide comprises an Fc, it forms a dimer. Thus, the structure $VHH_1$-$VHH_2$-Fc, if it forms a dimer, is considered to be tetravalent (i.e., the dimer has four VHH domains). Similarly, the structure $VHH_1$-$VHH_2$-$VHH_3$-Fc, if it forms a dimer, is considered to be hexavalent (i.e., the dimer has six VHH domains).

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, and/or the contact definition. A VHH comprises three CDRs, designated CDR1, CDR2, and CDR3.

The term "heavy chain constant region" as used herein refers to a region comprising at least three heavy chain constant domains, $C_H1$, hinge, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

A "Fc region" as used herein refers to a portion of a heavy chain constant region comprising CH2 and CH3. In some embodiments, an Fc region comprises a hinge, CH2, and CH3. In various embodiments, when an Fc region comprises a hinge, the hinge mediates dimerization between two Fc-containing polypeptides. An Fc region may be of any antibody heavy chain constant region isotype discussed herein. In some embodiments, an Fc region is an IgG1, IgG2, IgG3, or IgG4.

An "acceptor human framework" as used herein is a framework comprising the amino acid sequence of a heavy chain variable domain ($V_H$) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some embodiments, the number of amino acid changes are fewer than 10, or fewer than 9, or fewer than 8, or fewer than 7, or fewer than 6, or fewer than 5, or fewer than 4, or fewer than 3, across all of the human frameworks in a single antigen binding domain, such as a VHH.

"Affinity" refers to the strength of the sum total of noncovalent interactions between a single binding site of a molecule (for example, an antibody, such as an sdAb, or VHH-containing polypeptide) and its binding partner (for example, an antigen). The affinity or the apparent affinity of a molecule X for its partner Y can generally be represented by the dissociation constant ($K_d$) or the $K_{d\text{-}apparent}$, respectively. Affinity can be measured by common methods known in the art (such as, for example, ELISA $K_d$, KinExA, flow cytometry, and/or surface plasmon resonance devices), including those described herein. Such methods include, but are not limited to, methods involving BIAcore®, Octet®, or flow cytometry.

The term "$K_a$", as used herein, refers to the equilibrium dissociation constant of an antigen-binding molecule/antigen interaction. When the term "$K_a$" is used herein, it includes $K_a$ and $K_{d\text{-}apparent}$.

In some embodiments, the $K_d$ of the antigen-binding molecule is measured by flow cytometry using an antigen-expressing cell line and fitting the mean fluorescence measured at each antibody concentration to a non-linear one-site binding equation (Prism Software graphpad). In some such embodiments, the $K_d$ is $K_{d\text{-}apparent}$.

The term "biological activity" refers to any one or more biological properties of a molecule (whether present naturally as found in vivo, or provided or enabled by recombinant means).

An "agonist" or "activating" antibody is one that increases and/or activates a biological activity of the target antigen. In some embodiments, the agonist antibody binds to an antigen and increases its biologically activity by at least about 20%, 40%, 60%, 80%, 85% or more.

An "antagonist", a "blocking" or "neutralizing" antibody is one that inhibits, decreases and/or inactivates a biological activity of the target antigen. In some embodiments, the neutralizing antibody binds to an antigen and reduces its biologically activity by at least about 20%, 40%, 60%, 80%, 85% 90%, 95%, 99% or more.

An "affinity matured" sdAb or VHH-containing polypeptide refers to a sdAb or VHH-containing polypeptide with one or more alterations in one or more CDRs compared to a parent sdAb or VHH-containing polypeptide that does not possess such alterations, such alterations resulting in an improvement in the affinity of the sdAb or VHH-containing polypeptide for antigen.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to further refine and optimize sdAb VHH-containing polypeptide performance. In some embodiments, a humanized sdAb or VHH-containing polypeptide comprises a human Fc region. As will be appreciated, a humanized sequence can be identified by its primary sequence and does not necessarily denote the process by which the antibody was created.

An "effector-positive Fc region" possesses an "effector function" of a native sequence Fc region. Exemplary "effector functions" include Fc receptor binding; Clq binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, for example, Daeron, Annu. Rev. Immunol. 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. For example, the term "Fe receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

A "chimeric antigen receptor" as used herein refers to an engineered polypeptide that comprises an extracellular antigen recognition domain, a transmembrane domain, and an intracellular signaling domain. In some embodiments, the extracellular antigen recognition domain comprises a VHH domain.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |

TABLE 1-continued

| Original Residue | Exemplary Substitutions |
|---|---|
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NS0 cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example, a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

A "disease" or "disorder" as used herein refers to a condition where treatment is needed and/or desired.

The term "tumor cell", "cancer cell", "cancer", "tumor", and/or "neoplasm", unless otherwise designated, are used herein interchangeably and refer to a cell (or cells) exhibiting an uncontrolled growth and/or abnormal increased cell survival and/or inhibition of apoptosis which interferes with the normal functioning of bodily organs and systems. Included in this definition are benign and malignant cancers, hematologic cancers such as leukemias, lymphomas, and multiple myelomas, polyps, hyperplasia, as well as dormant tumors or micrometastases.

The terms "cancer" and "tumor" encompass solid and hematological/lymphatic cancers and also encompass malignant, pre-malignant, and benign growth, such as dysplasia. Exemplary cancers include, but are not limited to: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; acute myeloid leukemia (AML); chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

The term "non-tumor cell" or "non-cancer cell" as used herein refers to a normal cells or tissue. Exemplary non-tumor cells include, but are not limited to: T-cells, B-cells, natural killer (NK) cells, natural killer T (NKT) cells, dendritic cells, monocytes, macrophages, epithelial cells, fibroblasts, hepatocytes, interstitial kidney cells, fibroblast-like synoviocytes, osteoblasts, and cells located in the breast, skeletal muscle, pancreas, stomach, ovary, small intestines, placenta, uterus, testis, kidney, lung, heart, brain, liver, prostate, colon, lymphoid organs, bone, and bone-derived mesenchymal stem cells. The term "a cell or tissue located in the periphery" as used herein refers to non-tumor cells not located near tumor cells and/or within the tumor microenvironment.

The term "cells or tissue within the tumor microenvironment" as used herein refers to the cells, molecules, extracellular matrix and/or blood vessels that surround and/or feed a tumor cell. Exemplary cells or tissue within the tumor microenvironment include, but are not limited to: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells (Treg cells); macrophages; neutrophils; myeloid-derived suppressor cells (MDSCs) and other immune cells located proximal to a tumor. Methods for identifying tumor cells, and/or cells/tissues located within the tumor microenvironment are well known in the art, as described herein, below.

In some embodiments, an "increase" or "decrease" refers to a statistically significant increase or decrease, respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.); and/or cellular proliferation or cytokine production, compared to the same conditions but without the presence of a test agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering a therapeutic agent. "Ameliorating" also includes shortening or reduction in duration of a symptom.

The term "anti-cancer agent" is used herein in its broadest sense to refer to agents that are used in the treatment of one or more cancers. Exemplary classes of such agents in include, but are not limited to, chemotherapeutic agents, anti-cancer biologics (such as cytokines, receptor extracellular domain-Fc fusions, and antibodies), radiation therapy, CAR-T therapy, therapeutic oligonucleotides (such as antisense oligonucleotides and siRNAs) and oncolytic viruses.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" or "reference" in the context of an experiment or comparison, refers to a composition known to not contain an analyte ("negative control") or to contain an analyte ("positive control"). A positive control can comprise a known concentration of analyte. A control or reference may also refer to a control agent known to lack the activity of an agent being tested, such as an antibody.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time, but just over the time period being measured.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

The terms "pharmaceutical formulation" and "pharmaceutical composition" are used interchangeably and refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a nontoxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

Administration "in combination with" one or more further therapeutic agents includes simultaneous (concurrent) and sequential administration in any order.

The term "concurrently" is used herein to refer to administration of two or more therapeutic agents, where at least part of the administration overlaps in time, or where the administration of one therapeutic agent falls within a short period of time relative to administration of the other therapeutic agent, or wherein the therapeutic effects of both agents overlap for at least a period of time.

The term "sequentially" is used herein to refer to administration of two or more therapeutic agents that does not overlap in time, or wherein the therapeutic effects of the agents do not overlap.

As used herein, "in conjunction with" refers to administration of one treatment modality in addition to another treatment modality. As such, "in conjunction with" refers to administration of one treatment modality before, during, or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached, for example, to an antibody or antigen to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

Exemplary CLEC12a-Binding Polypeptides

CLEC12a-binding polypeptides are provided herein. In various embodiments, the CLEC12a-binding polypeptides comprise at least one VHH domain that binds CLEC12a. In some embodiments, the CLEC12a is human CLEC12a. In some embodiments, a CLEC12a-binding polypeptide blocks binding of CLEC12a to a ligand. In some embodiments, a CLEC12a-binding polypeptide provided herein comprises one, two, three, four, five, six, seven, or eight VHH domains that bind CLEC12a. In some embodiments, a CLEC12a-binding polypeptide provided herein comprises one, two, three, or four VHH domains that bind CLEC12a. CLEC12a-binding polypeptides may comprise one or more VHH domains that bind one or more target proteins other than CLEC12a. Such polypeptides may be referred to as "multispecific" polypeptides.

In some embodiments, a CLEC12a-binding polypeptide comprises at least one VHH domain that binds CLEC12a and an Fc region. In some embodiments, a CLEC12a-binding polypeptide provided herein comprises one, two, three, or four VHH domains and an Fc region. In some embodiments, an Fc region mediates dimerization of the CLEC12a-binding polypeptide at physiological conditions such that a dimer is formed that doubles the number of CLEC12a binding sites. For example, a CLEC12a-binding polypeptide comprising three VHH domains that bind CLEC12a and an Fc region is trivalent as a monomer, but at physiological conditions, the Fc region may mediate dimerization, such that the CLEC12a-binding polypeptide exists as a hexavalent dimer under such conditions.

In some embodiments, a CLEC12a-binding polypeptide comprises at least two VHH domains, wherein a first VHH domain binds a first epitope of CLEC12a and a second VHH domain binds a second epitope of CLEC12a. When the CLEC12a-binding polypeptide comprises a VHH domain that binds a first epitope of CLEC12a and a VHH domain that binds a second epitope of CLEC12a, the CLEC12a-binding polypeptide may be referred to as "biepitopic" or "bispecific." In some embodiments, a CLEC12a-binding polypeptide comprises at least two VHH domains, wherein a first VHH domain binds CLEC12a and a second VHH domain binds an antigen other than CLEC12a. Such polypeptides may be referred to as "bispecific" or "multispecific."

Nonlimiting exemplary CLEC12a-binding polypeptides are shown in Table 2. The sequences for the indicated single-domain antibodies are shown in the Table of Certain Sequences herein. A polypeptide name that begins with "hz" indicates that it is a humanized version of the corresponding parental polypeptide.

TABLE 2

Polypeptides comprising at least one VHH that binds CLEC12a

| Name | CDRs | VHH (or K version or KP version) |
|---|---|---|
| MB11 | SEQ ID NOs: 3, 4, and 5 | SEQ ID NO: 2 (or SEQ ID NO: 88) |
| MC02 | SEQ ID NOs: 7, 8, and 9 | SEQ ID NO: 6 (or SEQ ID NO: 89) |
| MC06 | SEQ ID NOs: 11, 12, and 13 | SEQ ID NO: 10 (or SEQ ID NO: 90) |
| ME02 | SEQ ID NOs: 15, 16, and 17 | SEQ ID NO: 14 (or SEQ ID NO: 91) |

TABLE 2-continued

Polypeptides comprising at least one VHH that binds CLEC12a

| Name | CDRs | VHH (or K version or KP version) |
|---|---|---|
| ME06 | SEQ ID NOs: 19, 20, and 21 | SEQ ID NO: 18 (or SEQ ID NO: 92) |
| MH07 | SEQ ID NOs: 23, 24, and 25 | SEQ ID NO: 22 (or SEQ ID NO: 93) |
| hzMB11v13 | SEQ ID NOs: 32, 33, and 34 | SEQ ID NO: 26 (or SEQ ID NO: 94) |
| hzMC02v6 | SEQ ID NOs: 35, 36, and 37 | SEQ ID NO: 27 (or SEQ ID NO: 95) |
| hzMC06v2 | SEQ ID NOs: 38, 39, and 40 | SEQ ID NO: 28 (or SEQ ID NO: 96) |
| hzME02v4 | SEQ ID NOs: 41, 42, and 43 | SEQ ID NO: 29 (or SEQ ID NO: 97) |
| hzME06v16 | SEQ ID NOs: 44, 45, and 46 | SEQ ID NO: 30 (or SEQ ID NO: 98) |
| haMH07v3 | SEQ ID NOs: 47, 48, and 49 | SEQ ID NO: 31 (or SEQ ID NO: 99) |

CLEC12a-Binding Polypeptides

In various embodiments, a VHH domain that binds CLEC12a comprises a CDR1 sequence selected from SEQ ID NOs: 3, 7, 11, 15, 19, 23, 32, 35, 38, 41, 44, and 47; a CDR2 sequence selected from SEQ ID NOs: 4, 8, 12, 16, 20, 24, 33, 36, 39, 42, 45, and 48; a CDR3 sequence selected from SEQ ID NOs: 5, 9, 13, 17, 21, 25, 34, 37, 40, 43, 46, and 49. In various embodiments, a VHH domain that binds CLEC12a comprises CDR1, CDR2, and CDR3 sequences selected from: SEQ ID NOs: 3, 4, and 5; SEQ ID NOs: 7, 8, and 9; SEQ ID NOs: 11, 12, and 13; SEQ ID NOs: 15, 16, and 17; SEQ ID NOs: 19, 20, and 21; SEQ ID NOs: 23, 24, and 25; SEQ ID NOs: 32, 33, and 34; SEQ ID NOs: 35, 36, and 37; SEQ ID NOs: 38, 39, and 40; SEQ ID NOs: 41, 42, and 43; SEQ ID NOs: 44, 45, and 46; and SEQ ID NOs: 47, 48, and 49. In various embodiments, the VHH domain is humanized.

In some embodiments, a VHH domain that binds CLEC12a comprises an amino acid sequence that is at least 85%, at least 90%, at least 95%, at least 96%, at least 97%, at least 98%, at least 99% identical to an amino acid sequence selected from SEQ ID NOs: 2, 6, 10, 14, 18, 22, 26, 27, 28, 29, 30, 31, 88, 89, 90, 91, 92, 93, 94, 95, 96, 97, 98, and 99. In some embodiments, a VHH domain that binds CLEC12a comprises an amino acid sequence selected from SEQ ID NOs: 2, 6, 10, 14, 18, 22, 26, 27, 28, 29, 30, 31, 88, 89, 90, 91, 92, 93, 94, 95, 96, 97, 98, and 99.

In various embodiments, a CLEC12a-binding polypeptide comprises one, two, three, or four VHH domains that bind CLEC12a.

In various embodiments, a CLEC12a-binding polypeptide comprises at least one VHH domain that binds CLEC12a and at least one VHH domain that binds a natural killer cell antigen or a T-cell antigen. In some such embodiments, the CLEC12a-binding polypeptide may be referred to as a multispecific antibody.

In some embodiments, a CLEC12a binding polypeptide comprises at least one VHH domain described herein fused to an Fc region. In some embodiments, the Fc region has a sequence selected from SEQ ID NOs: 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85.

In some embodiments, a VHH domain that binds CLEC12a is humanized. Humanized antibodies (such as sdAbs or VHH-containing polypeptides) are useful as therapeutic molecules because humanized antibodies reduce or eliminate the human immune response to non-human antibodies, which can result in an immune response to an antibody therapeutic, and decreased effectiveness of the therapeutic. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13: 1619-1633, and are further described, for example, in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272: 10678-10684 and Rosok et al., (1996) *J. Biol. Chem.* 271:22611-22618). Typically, the FR regions of a VHH are replaced with human FR regions to make a humanized VHH. In some embodiments, certain FR residues of the human FR are replaced in order to improve one or more properties of the humanized VHH. VHH domains with such replaced residues are still referred to herein as "humanized."

In various embodiments, an Fc region included in a CLEC12a-binding polypeptide is a human Fc region, or is derived from a human Fc region.

In some embodiments, an Fc region included in a CLEC12a-binding polypeptide is derived from a human Fc region, and comprises a three amino acid deletion in the lower hinge corresponding to IgG1 E233, L234, and L235, herein referred to as "Fc xELL" Fc xELL polypeptides do not engage FcγRs and thus are referred to as "effector silent" or "effector null", however in some embodiments, xELL Fc regions bind FcRn and therefore have extended half-life and transcytosis associated with FcRn mediated recycling.

In some embodiments, the Fc region included in a CLEC12a-binding polypeptide is derived from a human Fc region and comprises mutations M252Y and M428V, herein referred to as "Fc-YV". In some embodiments, such mutations enhance binding to FcRn at the acidic pH of the endosome (near 6.5), while losing detectable binding at neutral pH (about 7.2), allowing for enhanced FcRn mediated recycling and extended half-life.

In some embodiments, the Fc region included in a CLEC12a-binding polypeptide is derived from a human Fc region and comprises mutations designed for heterodimerization, herein referred to as "knob" and "hole". In some embodiments, the "knob" Fc region comprises the mutation T366W. In some embodiments, the "hole" Fc region comprises mutations T366S, L368A, and Y407V. In some embodiments, Fc regions used for heterodimerization comprise additional mutations, such as the mutation S354C on a first member of a heterodimeric Fc pair that forms an asymmetric disulfide with a corresponding mutation Y349C on the second member of a heterodimeric Fc pair. In some embodiments, one member of a heterodimeric Fc pair comprises the modification H435R or H435K to prevent protein A binding while maintaining FcRn binding. In some embodiments, one member of a heterodimeric Fc pair comprises the modification H435R or H435K, while the second member of the heterodimeric Fc pair is not modified at H435. In various embodiments, the hold Fc region comprises the modification H435R or H435K (referred to as "hole-R" in some instances when the modification is H435R), while the knob Fc region does not. In some instances, the hole-R mutation improves purification of the heterodimer over homodimeric hole Fc regions that may be present.

Nonlimiting exemplary Fc regions that may be used in a CLEC12a-binding polypeptide include Fc regions comprising the amino acid sequences of SEQ ID NOs: 50 to 85.

Chimeric Receptors and Engineered Cells

Provided herein are chimeric antigen receptors (CARs) having an extracellular domain comprising one or more of the CLEC12a-binding VHH domains provided herein. CAR constructs provided herein include an extracellular domain containing the one or more CLEC12a-binding VHH domain, a transmembrane domain and an intracellular signaling region. The one or more CLEC12a-binding VHH domain which form the antigen binding unit of the CAR binds or is capable of binding, i.e. targets, CLEC12a-binding with sufficient affinity such the CAR is useful in therapy in targeting a cell or tissue expressing CLEC12a-binding.

CARs are synthetic receptors typically containing an extracellular targeting/binding moiety that is associated with one or more signaling domains in a single fusion molecule that is expressed on the surface of a cell, such as a T cell. Thus, CARs combine antigen-specificity and T cell activating properties in a single fusion molecule. First generation CARs typically included the cytoplasmic region of the CD3zeta or Fc 1 receptor γ chain as their signaling domain. First generation CARs have been tested in phase I clinical studies in patients with ovarian cancer, renal cancer, lymphoma, and neuroblastoma, where they have induced modest responses (reviewed in Sadelain et al., Curr Opin Immunol, 21 (2): 215-223, 2009). Second generation CARs, which contain the signaling domains of a costimulatory molecule, such as CD28, and CD3zeta, provide dual signaling to direct combined activating and co-stimulatory signals. Third generation CARs are more complex with three or more signaling domains (reviewed in Sadelain et al., Cancer Discovery (3), 388-398, 2013 and Dotti et al, Immuno. Rev, 257 (1), 1-36, 2014).

In some embodiments, a provided CAR comprises a CLEC12a-binding VHH domain. In some embodiments, the CAR contains at least two VHH domains that target one or more antigen. In one embodiment, the antigen binding domain of a CAR comprises two or at least two CLEC12a-binding VHH domains, thus providing a bivalent molecule. In one embodiment, the antigen binding domain comprises two or at least two CLEC12a-binding VHH domains, but bind to different epitopes on CLEC12a. In such cases, the antigen binding domain comprises a first CLEC12a-binding VHH domain that binds to a first epitope of CLEC12a and a second VHH domain that binds to a second epitope of CLEC12a. The epitopes may be overlapping. Thus, in some embodiments, the antigen binding domain is biparatopic and the CAR is a biparatopic CAR. In yet another embodiment, the antigen binding domain comprises two CLEC12a-binding VHH domains that bind to the same epitopes on CLEC12a.

The transmembrane domain of a CAR provided herein is a domain that typically crosses or is capable of crossing or spanning the plasma membrane and is connected, directly or indirectly (e.g. via a spacer, such as an immunoglobulin hinge sequence) to the extracellular antigen binding domain and the endoplasmic portion containing the intracellular signaling domain. In one embodiment, the transmembrane domain of the CAR is a transmembrane region of a transmembrane protein (for example Type I transmembrane proteins), an artificial hydrophobic sequence or a combination thereof. In one embodiment, the transmembrane domain comprises the CD3zeta domain or CD28 transmembrane domain. Other transmembrane domains will be apparent to those of skill in the art and may be used in connection with embodiments of a CAR provided herein.

The intracellular signaling region of a CAR provided herein contains one or more intracellular signaling domain that transmits a signal to a T cell upon engagement of the antigen binding domain of the CAR, such as upon binding antigen. In some embodiments, the intracellular region contains an intracellular signaling domain that is or contains an ITAM signaling domain. Exemplary intracellular signaling domains include, for example, a signaling domain derived from $\zeta$ chain of the T-cell receptor complex or any of its homologs (e.g., $\eta$ chain, FcsRI$\gamma$ and $\beta$ chains, MB 1 (Iga) chain, B29 (Ig) chain, etc.), human CD3zeta chain, CD3 polypeptides ($\Delta$, $\delta$ and $\epsilon$), syk family tyrosine kinases (Syk, ZAP 70, etc.), src family tyrosine kinases (Lck, Fyn, Lyn, etc.) and other molecules involved in T-cell transduction, such as CD2, CD5, OX40 and CD28. In particular embodiments, the intracellular signaling region contains an intracellular signaling domain derived from the human CD3 zeta chain.

In some embodiments, the intracellular signaling region of a CAR can further contain an intracellular signaling domain derived from a costimulatory molecule. In such examples, such a signaling domain may enhance CAR-T cell activity, such as via enhancement of proliferation, survival and/or development of memory cells, after antigen specific engagement, for example, compared to a CAR that only contains an ITAM containing signaling domain, e.g. CD3 zeta. In some embodiments, the co-stimulatory domain is a functional signaling domain obtained from a protein selected from: CD28, CD137 (4-IBB), CD134 (OX40), Dap10, CD27, CD2, CD5, ICAM-1, LFA-1 (CD1 1a/CD18), Lck, TNFR-I, TNFR-II, Fas, CD30, CD40 or combinations thereof. In particular embodiments, the costimulatory signaling domain is derived or obtained from a human protein. In some aspects, the costimulatory signaling domain is derived or obtained from human CD28 or human CD137 (4-IBB).

In some embodiments, the costimulatory signaling domain is a derived from CD28 or 41BB.

In particular embodiments, the CAR further comprises a hinge or spacer region which connects the extracellular antigen binding domain and the transmembrane domain. This hinge or spacer region can be used to achieve different lengths and flexibility of the resulting CAR. Examples of the a hinge or spacer region that can be used include, but are not limited to, Fc fragments of antibodies or fragments or derivatives thereof, hinge regions of antibodies, or fragments or derivatives thereof, CH2 regions of antibodies, CH3 regions of antibodies, artificial spacer sequences, for example peptide sequences, or combinations thereof. Other hinge or spacer region will be apparent to those of skill in the art and may be used. In one embodiment, the hinge is an IgG4 hinge or a CD8A hinge.

In some embodiments, the spacer and transmembrane domain are the hinge and transmembrane domain derived from CD8.

Also provided herein is an isolated nucleic acid construct comprising at least one nucleic acid encoding a CAR as provided herein. In some aspects, the construct is an expression vector for expression of the CAR in a cell. The expression vector may be a viral vector. Viral vector technology is well known in the art and is described, for example, in Sambrook et al. (Molecular Cloning: A Laboratory Manual, Cold Spring Harbor Laboratory, New York, 2013). A number of viral based systems have been developed for gene transfer into mammalian cells. For example, retroviruses such as, adenovirus vectors are used. In one embodiment, a lentivirus vector is used.

In a further aspect, also provided is an isolated cell or cell population comprising one or more nucleic acid construct as described above. Also provided is an isolated cell or cell population that has been genetically modified to express a CAR provided herein. Thus, provided herein are genetically engineered cells which comprise, such as stably express, a CAR provided herein. In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. In some cases, the cell is a T cell, such as a CD4 and/or CD8 T cell. In some embodiments, the cells are autologous to the subject. For example, in some embodiments, T cells may be isolated from a patient (also called primary T cells) for engineering, e.g. transfection or transduction, with a CAR nucleic acid construct.

In an exemplary example, primary T-cells can be purified ex vivo (CD4 cells or CD8 cells or both) and stimulated with a TCR/CD28 agonists, such as anti-CD3/anti-CD28 coated beads. After a 2 or 3 day activation process, a recombinant expression vector encoding the CAR can be stably introduced into the primary T cells through standard lentiviral or retroviral transduction protocols or plasmid electroporation strategies. Cells can be monitored for CAR expression by, for example, flow cytometry using anti-epitope tag or antibodies that cross-react with native parental molecule. T-cells that express the CAR can be enriched through sorting with anti-epitope tag antibodies or enriched for high or low expression depending on the application.

The CAR engineered T-cells can be assayed for appropriate function by a variety of means. In some cases, in vitro cytotoxicity, proliferation, or cytokine assays (e.g., IFN-gamma expression) can be used to assess the function of engineered T-cells. Exemplary standard endpoints are percent lysis of a tumor line, proliferation of the engineered T-cell, or IFN-gamma protein expression in culture supernatant. In some cases, the ability to stimulate activation of T cells upon stimulation of the CAR, e.g. via antigen, can be assessed, such as by monitoring expression of activation markers such as CD69, CD44, or CD62L, proliferation and/or cytokine production.

Polypeptide Expression and Production

Nucleic acid molecules comprising polynucleotides that encode a CLEC12a-binding polypeptide are provided. In some embodiments, the nucleic acid molecule may also encode a leader sequence that directs secretion of the CLEC12a-binding polypeptide, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors comprising nucleic acids that encode the CLEC12a-binding polypeptides described herein are provided. Such vectors include, but are not limited to, DNA vectors, phage vectors, viral vectors, retroviral vectors, etc. In some embodiments, a vector is selected that is optimized for expression of polypeptides in a desired cell type, such as CHO or CHO-derived cells, or in NSO cells. Exemplary such vectors are described, for example, in Running Deer et al., *Biotechnol. Prog.* 20:880-889 (2004).

In some embodiments, a CLEC12a-binding polypeptide may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the CLEC12a-binding polypeptides may be expressed in yeast. See, e.g., U.S. Publication No. US 2006/0270045 A1. In some embodiments, a particular eukaryotic host cell is selected based on its ability to make desired post-translational modifications to the polypeptide. For example, in some embodiments, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

Host cells comprising any of the nucleic acids or vectors described herein are also provided. In some embodiments, a host cell that expresses a CLEC12a-binding polypeptide described herein is provided. The CLEC12a-binding polypeptides expressed in host cells can be purified by any suitable method. Such methods include, but are not limited to, the use of affinity matrices or hydrophobic interaction chromatography. Suitable affinity ligands include the ROR1 ECD and agents that bind Fc regions. For example, a Protein A, Protein G, Protein A/G, or an antibody affinity column may be used to bind the Fc region and to purify a CLEC12a-binding polypeptide that comprises an Fc region. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, the CLEC12a-binding polypeptide is produced in a cell-free system. Nonlimiting exemplary cell-free systems are described, for example, in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

In some embodiments, CLEC12a-binding polypeptides prepared by the methods described above are provided. In some embodiments, the CLEC12a-binding polypeptide is prepared in a host cell. In some embodiments, the CLEC12a-binding polypeptide is prepared in a cell-free system. In some embodiments, the CLEC12a-binding polypeptide is purified. In some embodiments, a cell culture media comprising a CLEC12a-binding polypeptide is provided.

In some embodiments, compositions comprising antibodies prepared by the methods described above are provided. In some embodiments, the composition comprises a CLEC12a-binding polypeptide prepared in a host cell. In some embodiments, the composition comprises a CLEC12a-binding polypeptide prepared in a cell-free system. In some embodiments, the composition comprises a purified CLEC12a-binding polypeptide.

Exemplary Methods of Treating Diseases Using CLEC12a-Binding Polypeptides

In some embodiments, methods of treating disease in an individual comprising administering a CLEC12a-binding polypeptide or cells expressing a CLEC12a-binding polypeptide are provided. In some embodiments, methods for treating cancer in an individual are provided. In some embodiments, methods for treating CLEC12a-expressing or CLEC12a-positive cancer in an individual are provided. The method comprises administering to the individual an effective amount of a CLEC12a-binding polypeptide or cells expressing a CLEC12a-binding polypeptide provided herein. In some embodiments, the CLEC12a-binding polypeptide is used to bring a cytotoxic agent to a CLEC12a-expressing cell. In some such embodiments, the CLEC12a-binding polypeptide comprises a binding domain that binds a cytotoxic T cell or NK cell. In some such embodiments, the binding domain binds CD3, T-cell receptor (TCR) α, TCRβ, CD28, CD16, CD32A, CD64, CD89, NKp46, or NKG2D. The binding domain may be, in some embodiments, a VHH domain or an antibody binding domain comprising a heavy chain variable region and a light chain variable region, such as a VH/VL, scFv, Fab fragment, etc.

In some embodiments, the CLEC12a-binding polypeptide is linked to a cytotoxic agent to form an immunoconjugate. Various cytotoxic agents used in immunoconjugates are known in the art, and include, but are not limited to, calicheamicins, auristatins, dolastatins, tubulicins, maytansinoids, cryptophycins, duocarmycins, esperamicins, pyrrolobenzodiazepines, and enediyne antibiotics.

In some embodiments, the CLEC12a-binding polypeptide is a chimeric antigen receptor expressed on a cytotoxic cell, such as a T cell (CAR-T) or NK cell (CAR-NK). Such methods of treatment may be in humans or animals. In some embodiments, methods of treating humans are provided.

Nonlimiting exemplary cancers that may be treated with CLEC12a-binding polypeptides or cells expressing CLEC12a-bindign polypeptides provided herein include, but are not limited to, lymphoma; Hodgkin's lymphoma; non-Hodgkin's lymphoma; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; acute myeloid leukemia (AML); chronic lymphocytic leukemia (CLL); acute lymphoblastic leukemia (ALL); Hairy cell leukemia; chronic myeloblastic leukemia. In some embodiments, the cancer is a CLEC12a-expressing (i.e., CLEC12a-positive cancer).

The CLEC12a-binding polypeptides or cells expressing CLEC12a-binding polypeptides can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of a CLEC12a-binding polypeptides or cells expressing CLEC12a-binding polypeptides is administered to a subject one or more times. In some embodiments, an effective dose of a CLEC12a-binding polypeptides or cells expressing CLEC12a-binding polypeptides is administered to the subject daily, semiweekly, weekly, every two weeks, once a month, etc. An effective dose of a CLEC12a-binding polypeptide or cells expressing a CLEC12a-binding polypeptide is administered to the subject at least once. In some embodiments, the effective dose of a CLEC12a-binding polypeptide or cells expressing a CLEC12a-binding polypeptide may be administered multiple times, including multiple times over the course of at least a month, at least six months, or at least a year.

In some embodiments, pharmaceutical compositions are administered in an amount effective for treating (including prophylaxis of) cancer. The therapeutically effective amount is typically dependent on the weight of the subject being treated, his or her physical or health condition, the extensiveness of the condition to be treated, or the age of the subject being treated. In general, antibodies may be administered in an amount in the range of about 0.05 mg/kg body weight to about 100 mg/kg body weight per dose. In some embodiments, antibodies may be administered in an amount in the range of about 10 µg/kg body weight to about 100 mg/kg body weight per dose. In some embodiments, antibodies may be administered in an amount in the range of about 50 µg/kg body weight to about 5 mg/kg body weight per dose. In some embodiments, antibodies may be administered in an amount in the range of about 100 µg/kg body weight to about 10 mg/kg body weight per dose. In some embodiments, antibodies may be administered in an amount in the range of about 100 µg/kg body weight to about 20 mg/kg body weight per dose. In some embodiments, antibodies may be administered in an amount in the range of about 0.5 mg/kg body weight to about 20 mg/kg body weight per dose. In some embodiments, antibodies may be administered in an amount in the range of about 0.5 mg/kg body weight to about 10 mg/kg body weight per dose. In some embodiments, antibodies may be administered in an amount in the range of about 0.05 mg/kg body weight to about 20 mg/kg body weight per dose. In some embodiments, antibodies may be administered in an amount in the range of about 0.05 mg/kg body weight to about 10 mg/kg body weight per dose. In some embodiments, antibodies may be administered in an amount in the range of about 5 mg/kg body weight or lower, for example less than 4, less than 3, less than 2, or less than 1 mg/kg of the antibody.

In some embodiments, CLEC12a-binding polypeptides or cells expressing CLEC12a-binding polypeptides can be administered in vivo by various routes, including, but not limited to, intravenous, intra-arterial, parenteral, intraperitoneal or subcutaneous. The appropriate formulation and route of administration may be selected according to the intended application.

In some embodiments, a therapeutic treatment using a CLEC12a-binding polypeptide is achieved by targeting a cytotoxic agent to a CLEC12a-expressing cell, such as a CLEC12a-expressing cancer cell. In some such embodiments, the CLEC12a-binding polypeptide is a chimeric antigen receptor expressed on a cytotoxic cell, such as a T cell or NK cell.

Pharmaceutical Compositions

In some embodiments, compositions comprising CLEC12a-binding polypeptides are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, a pharmaceutical composition comprises a CLEC12a-binding polypeptide at a concentration of at least 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 125 mg/mL, 150 mg/mL, 175 mg/mL, 200 mg/mL, 225 mg/mL, or 250 mg/mL.

Combination Therapy

CLEC12a-binding polypeptides or engineered cells of the present disclosure can be administered alone or in combination with other modes of treatment, such as other anti-cancer agents. They can be provided before, substantially contemporaneous with, or after other modes of treatment (i.e., concurrently or sequentially). In some embodiments, the method of treatment described herein can further include administering: radiation therapy, chemotherapy, vaccination, targeted tumor therapy, CAR-T therapy, oncolytic virus therapy, cancer immunotherapy, cytokine therapy, surgical resection, chromatin modification, ablation, cryotherapy, an antisense agent against a tumor target, a siRNA agent against a tumor target, a microRNA agent against a tumor target or an anti-cancer/tumor agent, or a biologic, such as an antibody, cytokine, or receptor extracellular domain-Fc fusion.

In some embodiments, a CLEC12a-binding polypeptide provided herein is given concurrently with one or more chemotherapeutic agent, CAR-T (chimeric antigen receptor T-cell) therapy, oncolytic virus therapy, cytokine therapy, and/or agents that target other checkpoint molecules, such as VISTA, gpNMB, B7H4, HHLA2, CD73, CTLA4, TIGIT, etc.

In some embodiments, the CLEC12a-binding polypeptide or engineered cells of the present disclosure is used in combination with other anti-tumor agents, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®)), PD-1 inhibitors (e.g., anti-PD1 antibodies, BMS-936558), PDL1 inhibitors anti-PDL1 antibodies, MPDL3280A), PDL2 inhibitors (e.g., anti-PDL2 antibodies) cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, or VEGF receptor(s), TRAIL/Apo2, and other bioactive and organic chemical agents, etc.

In some embodiments, a CLEC12a-binding polypeptide or engineered cell provided herein is given concurrently with a PD-1/PD-L1 therapy. Examples of PD-1/PD-L1 therapy include nivolumab (BMS); pidilizumab (CureTech, CT-011), pembrolizumab (Merck); durvalumab (Medimmune/AstraZeneca); atezolizumab (Genentech/Roche); avelumab (Pfizer); AMP-224 (Amplimmune); BMS-936559; AMP-514 (Amplimmune); MDX-1105 (Merck); TSR-042 (Tesaro/AnaptysBio, ANB-011); STI-A1010 (Sorrento Therapeutics); STI-A1110 (Sorrento Therapeutics); and other agents that are directed against programmed death-1 (PD-1) or programmed death ligand 1 (PD-L1).

In some embodiments, the CLEC12a-binding polypeptide or engineered cell of the present disclosure may be used in combination with a chemotherapeutic agent. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® (aldesleukin) rIL-2; LUIRTOTECAN® topoisomerase 1 inhibitor; ABARELIX® GnRH agoninst; and pharmaceutically acceptable salts, acids or derivatives of any of the above.

In some embodiments, the CLEC12a-binding polypeptide and the additional agent are formulated into a single therapeutic composition, and the CLEC12a-binding polypeptide and additional agent are administered simultaneously. Alternatively, the CLEC12a-binding polypeptide or engineered cell and the additional agent are separate from each other, e.g., each is formulated into a separate therapeutic composition, and the CLEC12a-binding polypeptide or engineered cell and the additional agent are administered simultaneously, or the CLEC12a-binding polypeptide or engineered cell and the additional agent are administered at different times during a treatment regimen. For example, the CLEC12a-binding polypeptide or engineered cell is administered prior to the administration of the additional agent, the CLEC12a-binding polypeptide or engineered cell is administered subsequent to the administration of the additional agent, or the CLEC12a-binding polypeptide or engineered cell and the additional agent are administered in an alternating fashion. The CLEC12a-binding polypeptide and additional agent may be administered in single doses or in multiple doses.

In some embodiments, the CLEC12a-binding polypeptide or engineered cell and the additional agent(s) are administered simultaneously. For example, the CLEC12a-binding polypeptide and the additional agent(s) can be formulated in a single composition or administered as two or more separate compositions. In some embodiments, the CLEC12a-binding polypeptide or engineered cell and the additional agent(s) are administered sequentially, or the CLEC12a-binding polypeptide or engineered cell and the additional agent are administered at different times during a treatment regimen.

Nonlimiting Exemplary Methods of Diagnosis and Treatment

In some embodiments, the methods described herein are useful for evaluating a subject and/or a specimen from a subject (e.g. a cancer patient). In some embodiments, evaluation is one or more of diagnosis, prognosis, and/or response to treatment.

In some embodiments, the methods described herein comprise evaluating a presence, absence, or level of a protein. In some embodiments, the methods described herein comprise evaluating a presence, absence, or level of expression of a nucleic acid. The compositions described herein may be used for these measurements. For example, in some embodiments, the methods described herein comprise contacting a specimen of the tumor or cells cultured from the tumor with a therapeutic agent as described herein.

In some embodiments, the evaluation may direct treatment (including treatment with the antibodies described herein). In some embodiments, the evaluation may direct the use or withholding of adjuvant therapy after resection. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, the polypeptides are used as an adjuvant therapy in the treatment of a cancer. In some embodiments, the polypeptides are used as the sole adjuvant therapy in the treatment of a cancer. In some embodiments, the polypeptides described herein are withheld as an adjuvant therapy in the treatment of a cancer. For example, if a patient is unlikely to respond to an antibody described herein or will have a minimal response, treatment may not be administered in the interest of quality of life and to avoid unnecessary toxicity from ineffective chemotherapies. In such cases, palliative care may be used.

In some embodiments the polypeptides are administered as a neoadjuvant therapy prior to resection. In some embodiments, neoadjuvant therapy refers to therapy to shrink and/or downgrade the tumor prior to any surgery. In some embodiments, neoadjuvant therapy means chemotherapy administered to cancer patients prior to surgery. In some embodiments, neoadjuvant therapy means an antibody is administered to cancer patients prior to surgery. Types of cancers for which neoadjuvant chemotherapy is commonly considered include, for example, breast, colorectal, ovarian, cervical, bladder, and lung. In some embodiments, the polypeptides are used as a neoadjuvant therapy in the treatment of a cancer. In some embodiments, the use is prior to resection.

In some embodiments, the tumor microenvironment contemplated in the methods described herein is one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells; macrophages; other lymphoid cells; neutrophils; and other immune cells located proximal to a tumor.

Kits

Also provided are articles of manufacture and kits that include any of CLEC12a-binding polypeptides as described herein, and suitable packaging. In some embodiments, the invention includes a kit with (i) a CLEC12a-binding polypeptide, and (ii) instructions for using the kit to administer the CLEC12a-binding polypeptide to an individual.

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed. Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of the antibodies generally include information as to dosage, dosing schedule, and route of administration for the intended treatment or industrial use. The kit may further comprise a description of selecting an individual suitable or treatment.

The containers may be unit doses, bulk packages (e.g., multi-dose packages) or sub-unit doses. For example, kits may also be provided that contain sufficient dosages of molecules disclosed herein to provide effective treatment for an individual for an extended period, such as about any of a week, 2 weeks, 3 weeks, 4 weeks, 6 weeks, 8 weeks, 3 months, 4 months, 5 months, 6 months, 7 months, 8 months, 9 months, or more. Kits may also include multiple unit doses of molecules and instructions for use and packaged in quantities sufficient for storage and use in pharmacies, for example, hospital pharmacies and compounding pharmacies. In some embodiments, the kit includes a dry (e.g., lyophilized) composition that can be reconstituted, resuspended, or rehydrated to form generally a stable aqueous suspension of antibody.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: CLEC12a Single-Domain Antibodies

Single domain antibodies targeting human CLEC12a were generated via immunization of llamas and alpaca with a recombinant version of the human CLEC12a extracellular domain.

Following the development of specific anti-CLEC12a antibody titers, llama/alpaca peripheral blood mononuclear cells (PBMCs) were isolated from 500 mL of blood from the immunized animal and total mRNA was isolated using the Qiagen RNeasy Maxi Kit and subsequently converted to first strand cDNA using Thermo Superscript IV Reverse Transcriptase and oligo-dT priming. VHH sequences were specifically amplified via PCR using the cDNA as template and cloned into a yeast surface display vector as VHH-Fc-AGA2 fusion proteins.

Yeast libraries displaying the VHH-Fc-AGA2 fusion proteins were enriched using recombinant forms of the CLEC12a ECD via magnetic bead isolation followed by fluorescence activated cell sorting (FACS). Sorted yeast were plated out and isolated colonies were picked into 96-well blocks and grown in media that switched the expression from surface displayed VHH-Fc to secretion into the media. Supernatants from the 96-well yeast secretion cultures were applied to 293F cells transiently transfected with CLEC12a (CLEC12a positive) or untransfected 293F cells (CLEC12a negative), washed, treated with fluorophore labelled anti-human IgG1 Fc secondary antibody, and analyzed by 96-well flow cytometry.

Nucleic acid sequences encoding VHHs that bound to CLEC12a positive cells and not to CLEC12a negative cells were cloned in-frame with a human Fc encoding region into mammalian expression vectors, and expressed by transient transfection in HEK293 Freestyle cells (293F cells) or CHO cells using polyethylenimine. Supernatant was collected after 3-7 days, secreted recombinant protein was purified by protein A chromatography, and concentration was calculated from the absorbance at 280 nm and extinction coefficient.

The epitopes of single domain antibodies (sdAbs) that comprise VHH domains that bind CLEC12a were compared using Bio-Layer Interferometry. 7 µg/mL of mFc-CLEC12a-ECD (SEQ ID NO: 87) was immobilized on anti-mFc coated capture sensors. 100 nM of one sdAb was then loaded onto the CLEC12a antigen and allowed to come to equilibrium. The sensors were then transferred into 100 nM of a second sdAb. An increase in assay signal represents binding, indicating that the second sdAb was targeting an epitope distinct from the epitope of the first sdAb.

Camelid-derived CLEC12a VHHs were humanized using the human VH3-23 germline as scaffold. Camelid residues that contribute to solubility, specificity, stability and/or affinity remained unmodified. Furthermore, where possible and as needed amino acid sequences that posse potential developability liabilities were modified to mitigate this risk. In addition all humanized variants contained a LeuIlGlu (L11E) modification, as described in US20160207981.

Figure 1B:
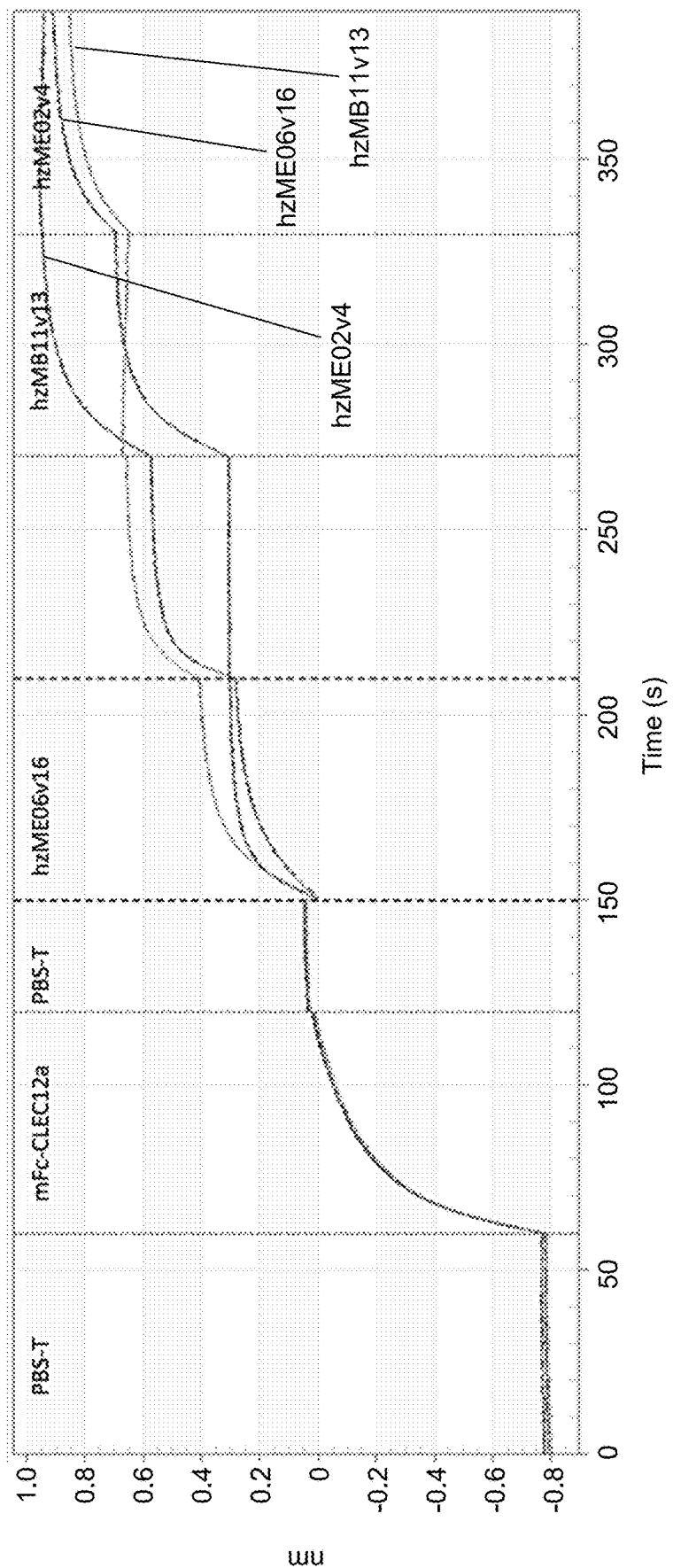
Figure 2A:
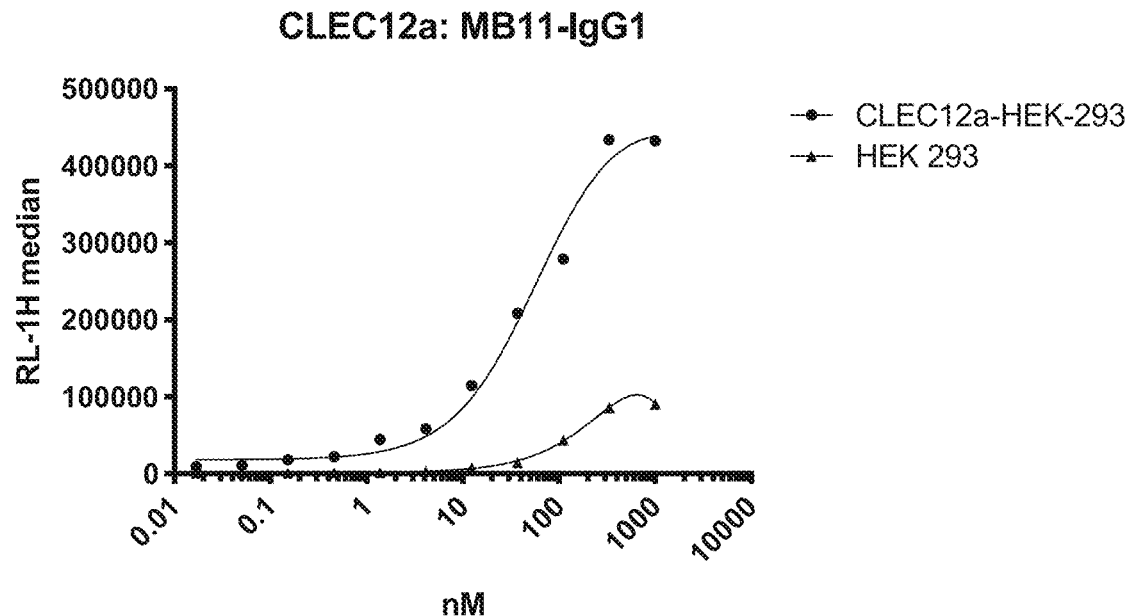
FIG. 2A-2L show binding of certain single-domain antibodies (sdAbs) to CLEC12a expressed on HEK 293 cells. "CLEC12a-HEK-293" indicates HEK 293 cells that have been transfected with a plasmid encoding CLEC12a, as described in Example 2. "HEK-293" indicates untransfected HEK 293 cells.
Figure 2B:
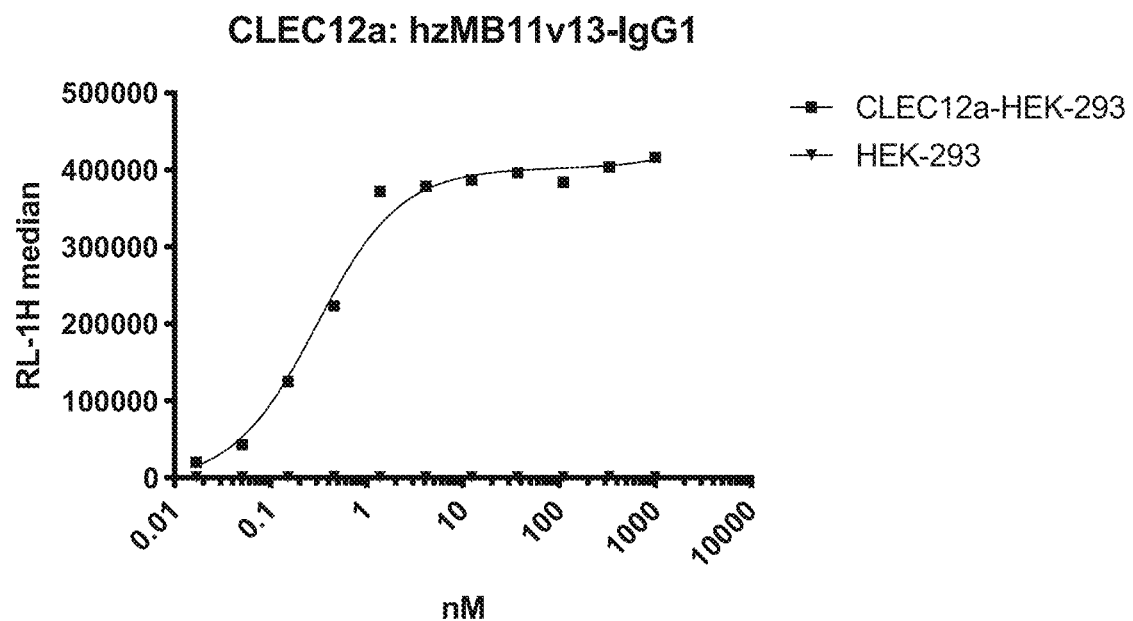
Figure 2C:
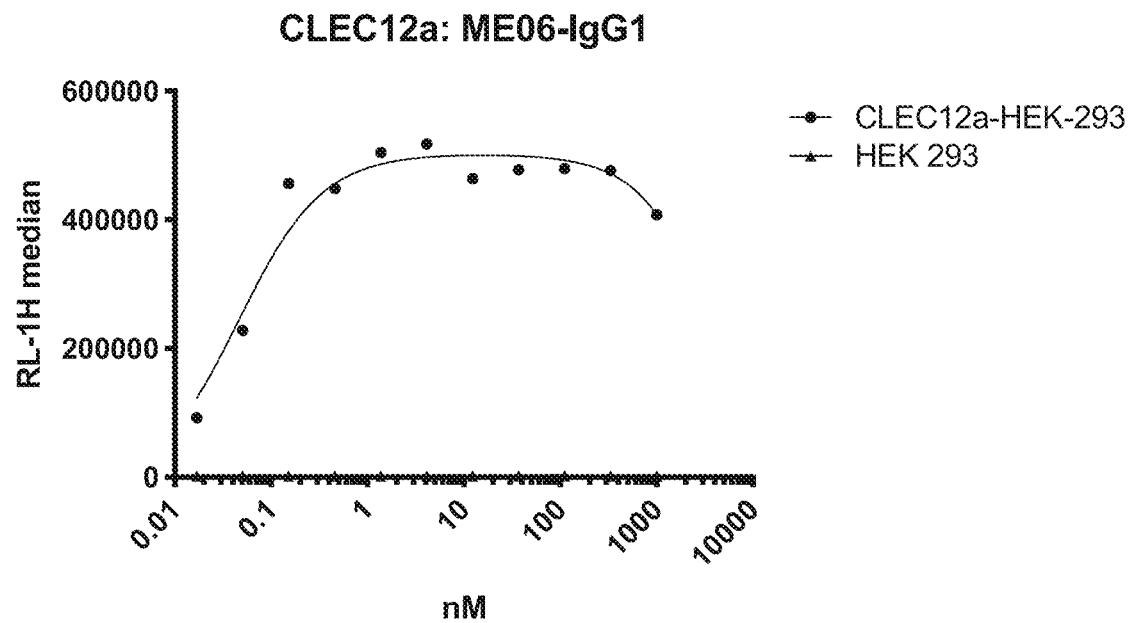
Figure 2D:
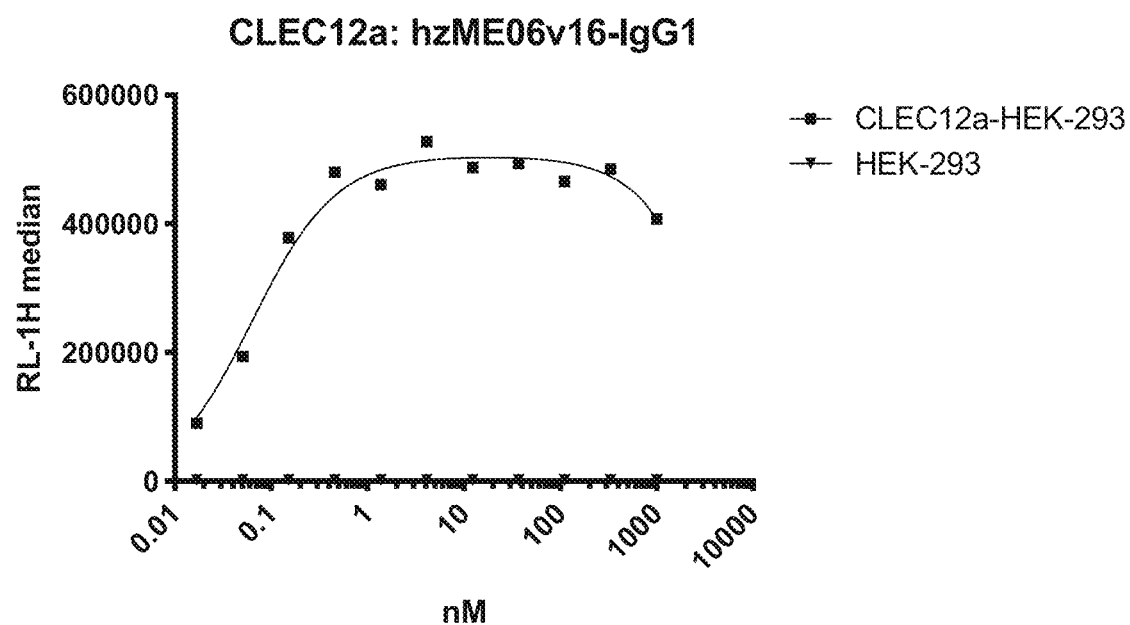
Figure 2E:
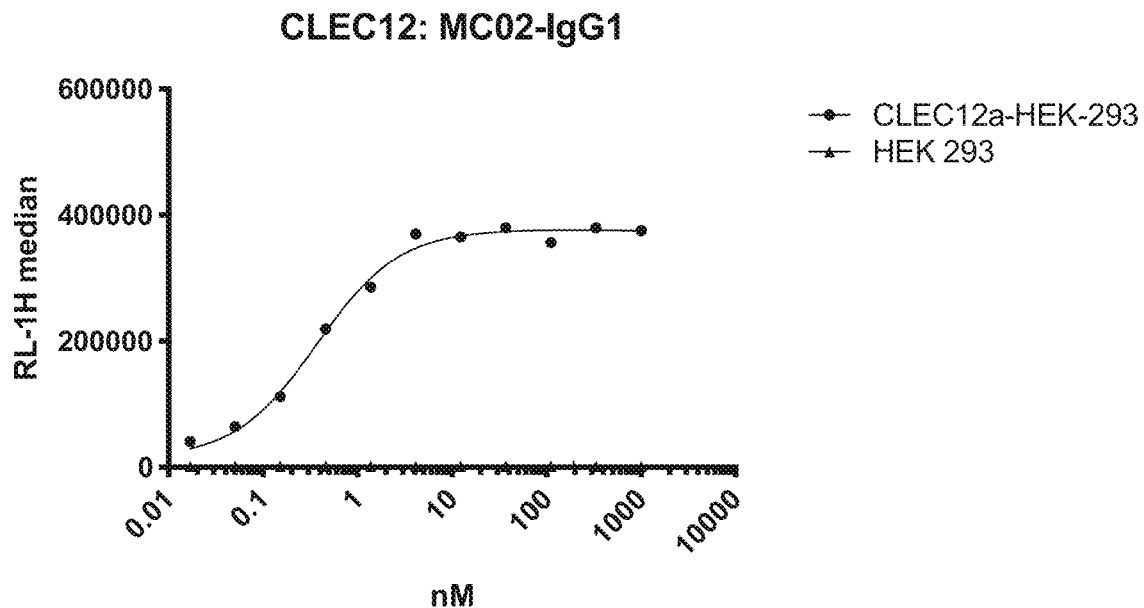
Figure 2F:
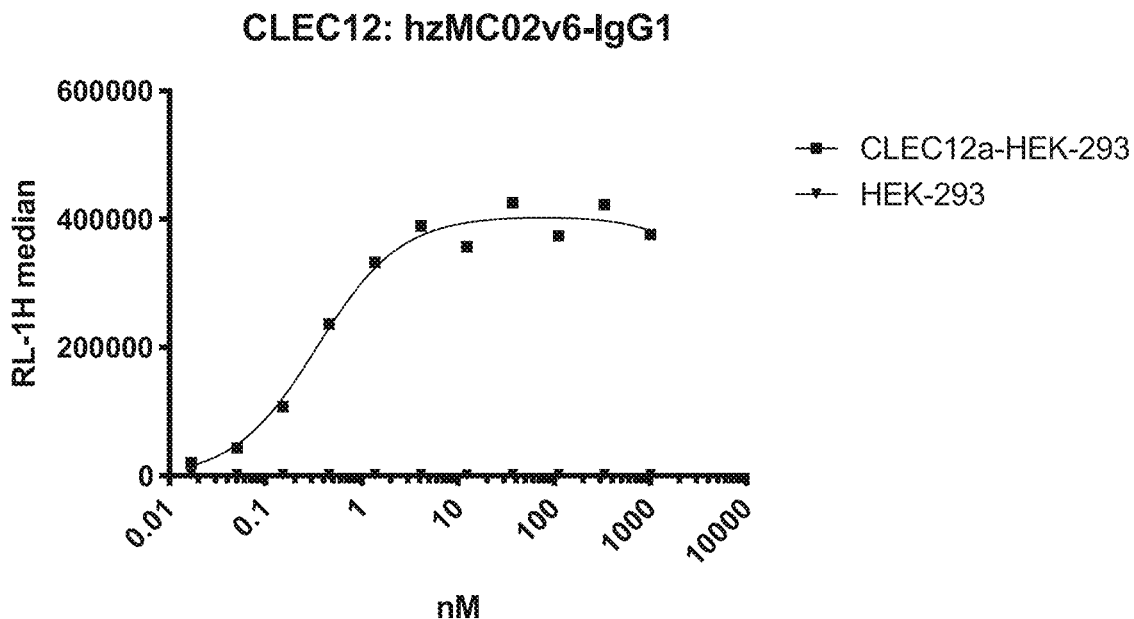
Figure 2G:
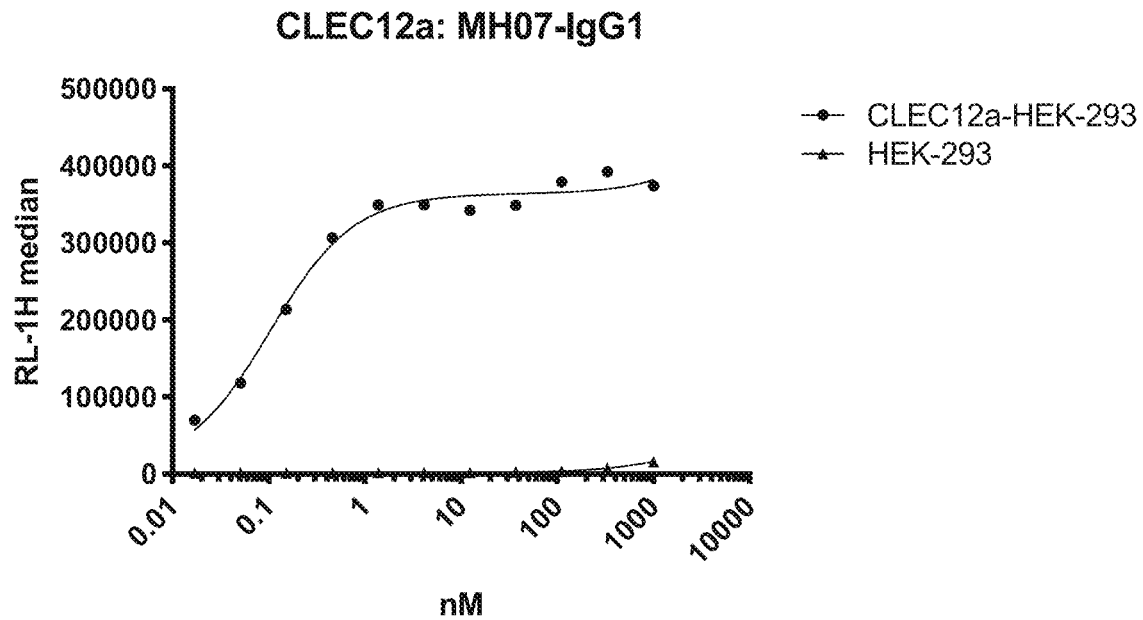
Figure 2H:
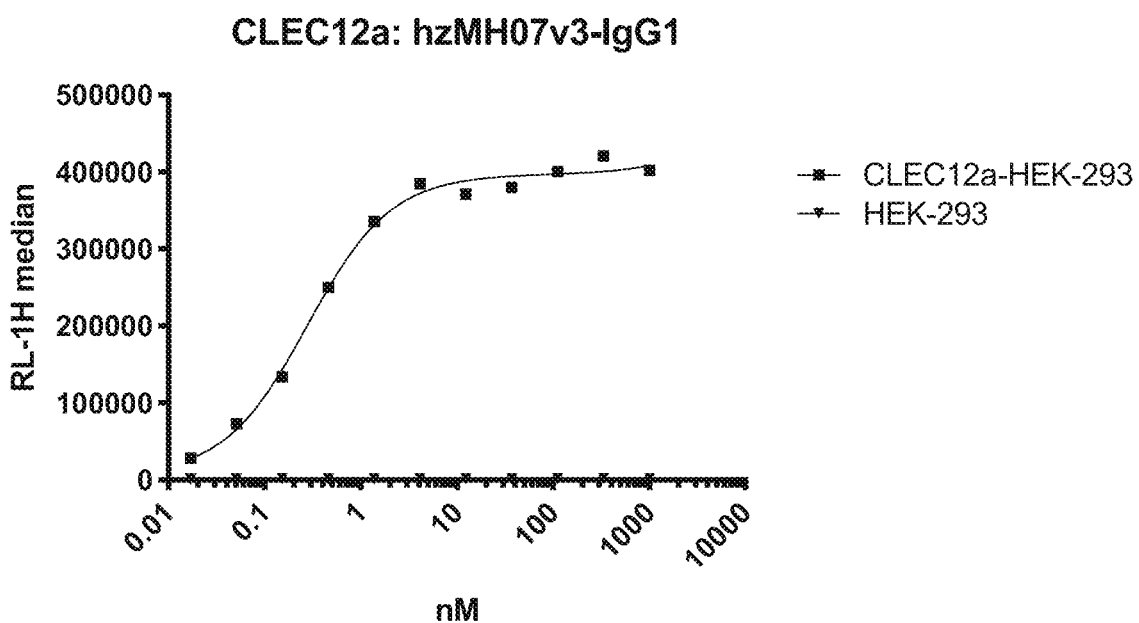
Figure 2I:
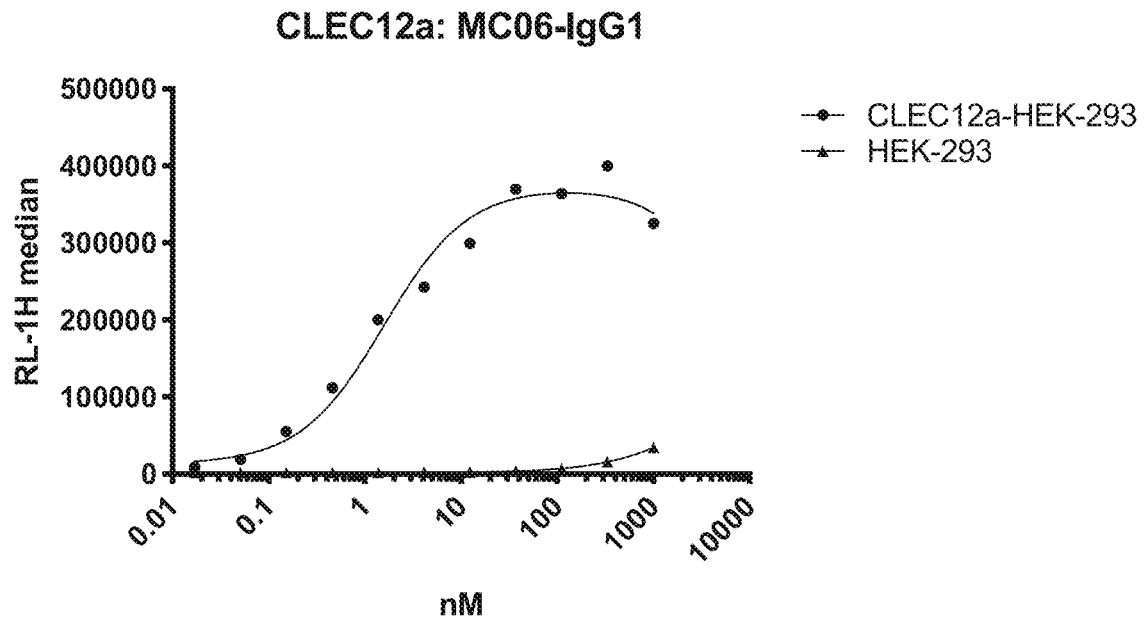
Figure 2J:
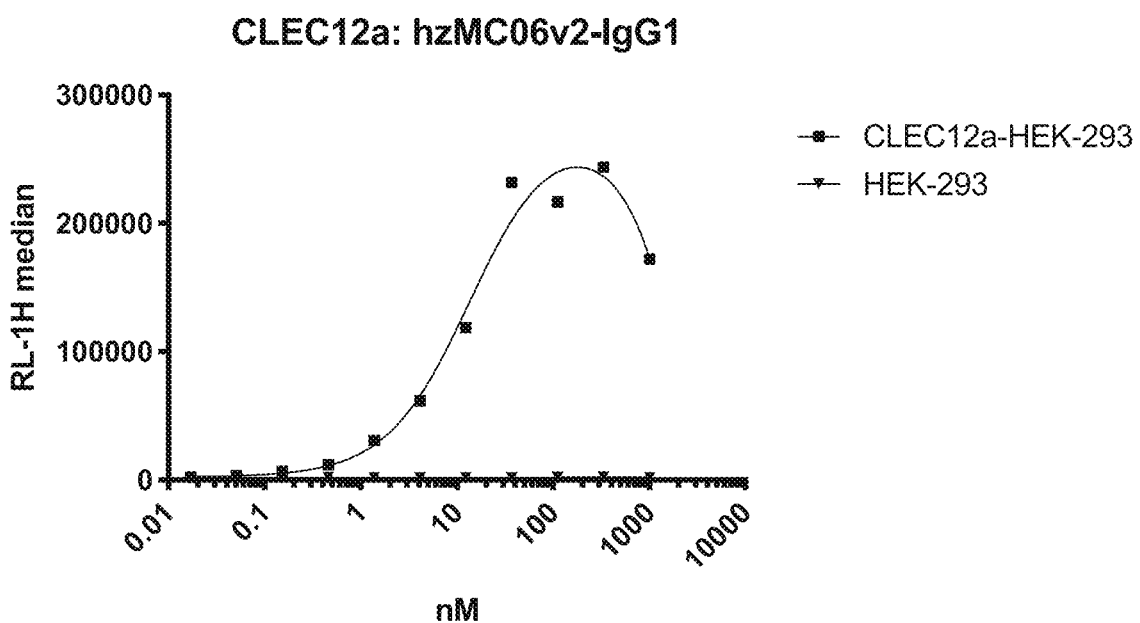
Figure 2K:
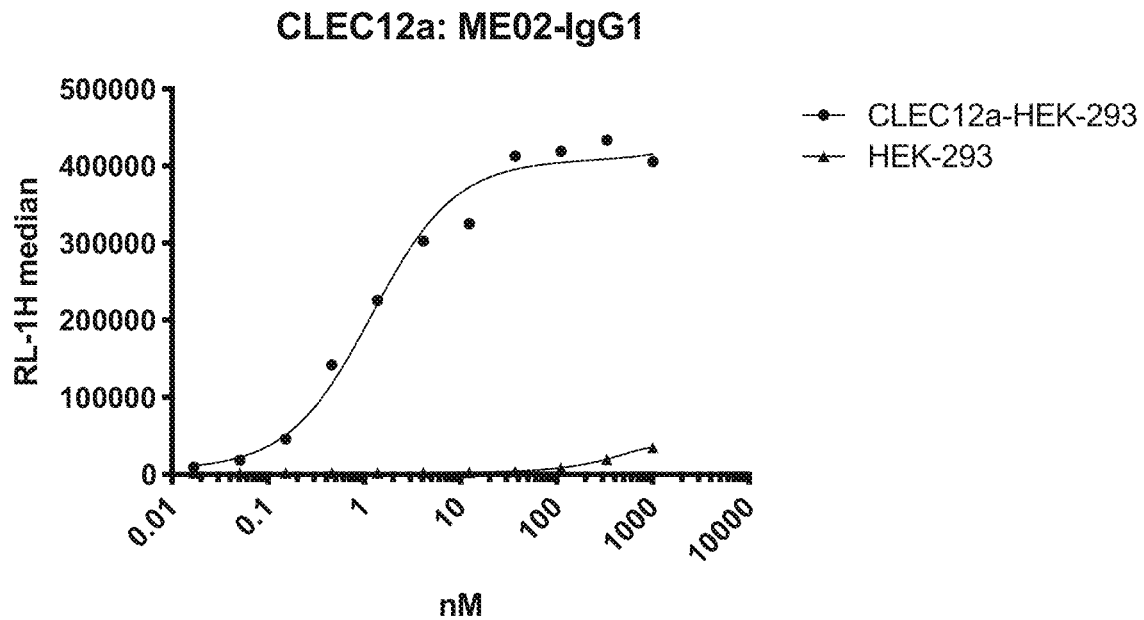
Figure 2L:
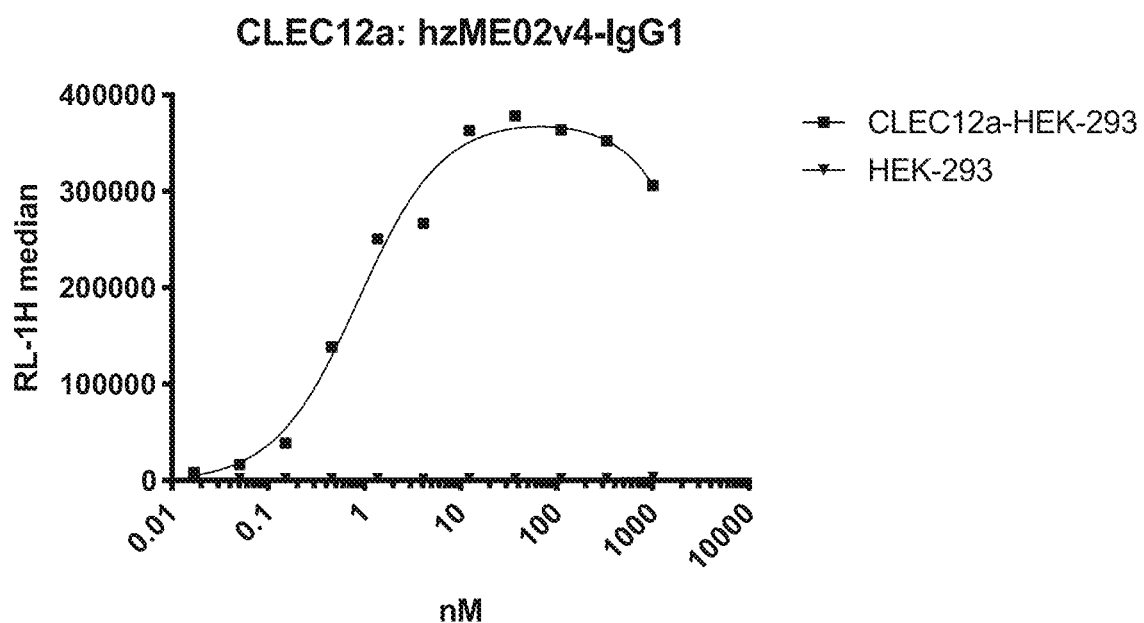

The results indicate that three distinct epitopes were found among humanized versions of sdAbs MB11, ME06, MC02, MH07, MC06, and ME02. As shown in FIG. 1A, sdAbs hzME02v4 and hzME06v16 have different epitopes than sdAbs hzMB11v13, hzMC02v6, hzMH07v3, and hzMC06v2. As shown in FIG. 1B, none of sdAbs hzME06v16, hzME02v4, and hzMB11v13 have a common epitope. A summary of the results is shown in Table 3 below.

TABLE 3

| sdAb | Epitope Bin |
| --- | --- |
| hzMB11v13 | 1 |
| hzME06v16 | 2 |
| hzMC02v6 | 1 |
| hzMH07v3 | 1 |
| hzMC06v2 | 1 |
| hzME02v4 | 3 |

Example 2: Binding of Polypeptides to CLEC12a

Binding of sdAbs to human CLEC12a was assessed by flow cytometry. Each sdAb comprised a VHH domain, as indicated in Table 4 below, and a human IgG1 xELL Fc region in which amino acids Glu233, Leu234, and Leu235, according to EU numbering, were deleted (SEQ ID NO: 51). HEK 293 cells were transiently transfected with a plasmid encoding CLEC12a (UniProt Accession No. Q5QGZ9.3; SEQ ID NO: 1) and used as the positive cell line, and untransfected HEK 293 cells were used as CLEC12a-negative cells. Each cell type was plated at 30,000 cells/well in FACS buffer (PBS 1% BSA, 0.1% NaN$_3$ pH 7.4) on a 96-well round-bottom plate. The sdAbs were diluted in FACS buffer in a 3-fold, 11 point serial dilution. The sdAb dilutions were added to the plated cells, and assay plates were incubated for 30 minutes at 4° C. After washing twice in 150 µL of FACS buffer, cells in each well were resuspended in 100 µL of 1:2000 Alexa Fluor 647-conjugated Anti-Human IgG secondary diluted in FACS buffer and incubated at 4° C. for 30 minutes. The cells were washed twice more, then bound antibody was detected by flow cytometry.

Flow cytometric analysis was performed on an Intellicyte iQue Plus and fluorescence was plotted as median fluorescence intensity. The apparent affinity ($K_d$, nM) was determined using one site binding non-linear regression in PRISM graph software.

As shown in FIGS. 2A to 2L, the tested sdAbs displayed CLEC12a binding and did not bind or exhibited minimal binding to untransfected HEK 293 cells that do not express CLEC12a. The apparent binding affinities are shown in Table 4 below.

TABLE 4

| sdAb | Apparent $K_d$ (nM) | SEQ ID NO of VHH domain |
|---|---|---|
| MB11 | 58.6 | 2 |
| hzMB11v13 | 0.3 | 26 |
| ME06 | 0.05 | 18 |
| hzME06v16 | 0.06 | 30 |
| MC02 | 0.37 | 6 |
| hzMC02v6 | 0.35 | 27 |
| MH07 | 0.10 | 22 |
| hzMH07v3 | 0.28 | 31 |
| MC06 | 1.58 | 10 |

TABLE 4-continued

| sdAb | Apparent $K_d$ (nM) | SEQ ID NO of VHH domain |
|---|---|---|
| hzMC06v2 | 13.98 | 28 |
| ME02 | 1.2 | 14 |
| hzME02v4 | 0.87 | 29 |

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

Table of Certain Sequences

| SEQ ID NO | Description | Sequence |
|---|---|---|
| 1 | Human CLEC12a | MSEEVTYADL QFQNSSEMEK IPEIGKFGEK APPAPSHVWR PAALFLTLLC LLLLIGLGVL ASMFHVTLKI EMKKMNKLQN ISEELQRNIS LQLMSNMNIS NKIRNLSTTL QTIATKLCRE LYSKEQEHKC KPCPRRWIWH KDSCYFLSDD VQTWQESKMA CAAQNASLLK INNKNALEFI KSQSRSYDYW LGLSPEEDST RGMRVDNIIN SSAWVIRNAP DLNNMYCGYI NRLYVQYYHC TYKKRMICEK MANPVQLGST YFREA |
| 2 | MB11 | QVQLQQSGGGLVQPGGSLRLSCVASGFLFSIYDMNWYRQAPGKEREWIAGITNNG YSTAYTDSVQGRFTISRDNAKNTIYLQMTSLKPEDTAVYYCHADLTKCYDGEYAW GQGTQVTV |
| 88 | MB11 K version | QVQLQQSGGGLVQPGGSLRLSCVASGFLFSIYDMNWYRQAPGKEREWIAGITNNG YSTAYTDSVQGRFTISRDNAKNTIYLQMTSLKPEDTAVYYCHADLTKCYDGEYAW GQGTQVTVK |
| 3 | MB11 CDR1 | GFLFSIYDMN |
| 4 | MB11 CDR2 | GITNNGYSTA |
| 5 | MB11 CDR3 | DLTKCYDGEYA |
| 6 | MC02 | QVQLVQSGGGLAQPGGSLRLSCTASGFTFRINDMGWYRQAPGKECEMVAGISNNG FSTAYADSVKGRFTISRDNAKNTVSLQMDSLKSEDTAVYYCHRTDDGAAHACSRG QGTQVTV |
| 89 | MC02 K version | QVQLVQSGGGLAQPGGSLRLSCTASGFTFRINDMGWYRQAPGKECEMVAGISNNG FSTAYADSVKGRFTISRDNAKNTVSLQMDSLKSEDTAVYYCHRTDDGAAHACSRG QGTQVTVK |
| 7 | MC02 CDR1 | GFTFRINDMG |
| 8 | MC02 CDR2 | GISNNGFSTA |
| 9 | MC02 CDR3 | TDDGAAHACS |
| 10 | MC06 | QVQLQESGGGLVQPGGSLRLSCAASGFTFSVYDMNWYRQTPGKEREWVAGISNNG FSTAYAGSVKGRFTISRDNAENTVYLQMNSLKSEDTAVYYCNLDVHGRVGAQGDY WGQGTQVTV |
| 90 | MC06 K version | QVQLQESGGGLVQPGGSLRLSCAASGFTFSVYDMNWYRQTPGKEREWVAGISNNG FSTAYAGSVKGRFTISRDNAENTVYLQMNSLKSEDTAVYYCNLDVHGRVGAQGDY WGQGTQVTVK |
| 11 | MC06 CDR1 | GFTFSVYDMN |
| 12 | MC06 CDR2 | GISNNGFSTA |
| 13 | MC06 CDR3 | DVHGRVGAQGDY |
| 14 | ME02 | QVQLQQSGGGLVQVGGSQRLSCAASGRTFEYDDMVWFRQAPGKEREEVAGISWSG GSIYYADSVKGRFSISRDNAKNTVYLEMNRLKPEDTAVYYCNVGSYWGQGTQVTV |

Table of Certain Sequences

| SEQ ID NO | Description | Sequence |
|---|---|---|
| 91 | ME02 K version | QVQLQQSGGGLVQVGGSQRLSCAASGRTFEYDDMVWFRQAPGKEREEVAGISWSGGSIYYADSVKGRFSISRDNAKNTVYLEMNRLKPEDTAVYYCNVGSYWGQGTQVTVK |
| 15 | ME02 CDR1 | GRTFEYDDMV |
| 16 | ME02 CDR2 | GISWSGGSIY |
| 17 | ME02 CDR3 | GSY |
| 18 | ME06 | QVQLVQSGGGLVQAGGSLRLSCVASGFTFDDYAIGWFRQAPGKEREGVSCISNSDGSTYYADSVKGRFTISSDNAKNTVYLHVNSLNPEDTAVYYCALREGLPLLLDSLWRQPVEYDYWGQGTQVTV |
| 92 | ME06 K version | QVQLVQSGGGLVQAGGSLRLSCVASGFTFDDYAIGWFRQAPGKEREGVSCISNSDGSTYYADSVKGRFTISSDNAKNTVYLHVNSLNPEDTAVYYCALREGLPLLLDSLWRQPVEYDYWGQGTQVTVK |
| 19 | ME06 CDR1 | GFTFDDYAIG |
| 20 | ME06 CDR2 | CISNSDGSTY |
| 21 | ME06 CDR3 | REGLPLLLDSLWRQPVEYDY |
| 22 | MH07 | QVQLVQSGGGLVQPGGSLRLSCVASGLLFSIYDMNWYRQAPGKEREWIAGITNNGYSTAYTDSVQGRFTISRDNAKNTVYLQMNSLKPEDTAVYYCHTDEWGREYWGQGTQVTV |
| 93 | MH07 K version | QVQLVQSGGGLVQPGGSLRLSCVASGLLFSIYDMNWYRQAPGKEREWIAGITNNGYSTAYTDSVQGRFTISRDNAKNTVYLQMNSLKPEDTAVYYCHTDEWGREYWGQGTQVTVK |
| 23 | MH07 CDR1 | GLLFSIYDMN |
| 24 | MH07 CDR2 | GITNNGYSTA |
| 25 | MH07 CDR3 | DEWGREY |
| 26 | hzMB11v13 | EVQLVESGGGEVQPGGSLRLSCAASGFLFSIYDMNWYRQAPGKEREWVAGITNNGYSTAYAESVKGRFTISRDNAKNTIYLQMSSLRAEDTAVYYCHADLTKAYDVEYAWGQGTLVTV |
| 94 | hzMB11v13 KP version | EVQLVESGGGEVQPGGSLRLSCAASGFLFSIYDMNWYRQAPGKEREWVAGITNNGYSTAYAESVKGRFTISRDNAKNTIYLQMSSLRAEDTAVYYCHADLTKAYDVEYAWGQGTLVTVKP |
| 27 | hzMC02v6 | EVQLVESGGGEVQPGGSLRLSCAASGFTFRINDMGWYRQAPGKECEMVAGISNNGFSTAYAESVKGRFTISRDNAKNTVYLQMSSLRAEDTAVYYCHRTDEGAAHACSRGQGTLVTV |
| 95 | hzMC02v6 KP version | EVQLVESGGGEVQPGGSLRLSCAASGFTFRINDMGWYRQAPGKECEMVAGISNNGFSTAYAESVKGRFTISRDNAKNTVYLQMSSLRAEDTAVYYCHRTDEGAAHACSRGQGTLVTVKP |
| 28 | hzMC06v2 | EVQLVESGGGEVQPGGSLRLSCAASGFTFSVYDMNWYRQAPGKEREWVSGISNNGFSTAYAESVKGRFTISRDNAKNTLYLQMSSLRAEDTAVYYCNLDVHGRVGAQGDYWGQGTLVTV |
| 96 | hzMC06v2 KP version | EVQLVESGGGEVQPGGSLRLSCAASGFTFSVYDMNWYRQAPGKEREWVSGISNNGFSTAYAESVKGRFTISRDNAKNTLYLQMSSLRAEDTAVYYCNLDVHGRVGAQGDYWGQGTLVTVKP |
| 29 | hzME02v4 | EVQLVESGGGEVQPGGSLRLSCAASGRTFEYDDMVWFRQAPGKEREEVAGISWSGGSIYYAESVKGRFSISRDNAKNTVYLEMNRLKPEDTAVYYCNVGSYWGQGTLVTV |
| 97 | hzME02v4 KP version | EVQLVESGGGEVQPGGSLRLSCAASGRTFEYDDMVWFRQAPGKEREEVAGISWSGGSIYYAESVKGRFSISRDNAKNTVYLEMNRLKPEDTAVYYCNVGSYWGQGTLVTVKP |
| 30 | hzME06v16 | EVQLVESGGGEVQPGGSLRLSCAASGFTFDDYAIGWFRQAPGKEREGVSTISSSDGSTYYAESVKGRFTISRDNAKNTVYLQMSSLRAEDTAVYYCALREGLPLLLDTLWRQPVEYDYWGQGTQVTV |

-continued

Table of Certain Sequences

| SEQ ID NO | Description | Sequence |
|---|---|---|
| 98 | hzME06v16 KP version | EVQLVESGGGEVQPGGSLRLSCAASGFTFDDYAIGWFRQAPGKEREGVSTISSSDGSTYYAESVKGRFTISRDNAKNTVYLQMSSLRAEDTAVYYCALREGLPLLLDTLWRQPVEYDYWGQGTQVTVKP |
| 31 | hzMH07v3 | EVQLVESGGGEVQPGGSLRLSCAASGLLFSIYDMNWYRQAPGKEREWVAGITNNGYSTAYAESVKGRFTISRDNAKNTVYLQMSSLRAEDTAVYYCHTDEWGREYWGQGTLVTV |
| 99 | hzMH07v3 KP version | EVQLVESGGGEVQPGGSLRLSCAASGLLFSIYDMNWYRQAPGKEREWVAGITNNGYSTAYAESVKGRFTISRDNAKNTVYLQMSSLRAEDTAVYYCHTDEWGREYWGQGTLVTVKP |
| 32 | CDR1 of hzMB11v13 | GFLFSIYDMN |
| 33 | CDR2 of hzMB11v13 | GITNNGYSTA |
| 34 | CDR3 of hzMB11v13 | DLTKAYDVEYA |
| 35 | CDR1 of hzMC02v6 | GFTFRINDMG |
| 36 | CDR2 of hzMC02v6 | GISNNGFSTA |
| 37 | CDR3 of hzMC02v6 | TDEGAAHACS |
| 38 | CDR1 of hzMC06v2 | GFTFSVYDMN |
| 39 | CDR2 of hzMC06v2 | GISNNGFSTA |
| 40 | CDR3 of hzMC06v2 | DVHGRVGAQGDY |
| 41 | CDR1 of hzME02v4 | GRTFEYDDMV |
| 42 | CDR2 of hzME02v4 | GISWSGGSIY |
| 43 | CDR3 of hzME02v4 | GSY |
| 44 | CDR1 of hzME06v16 | GFTFDDYAIG |
| 45 | CDR2 of hzME06v16 | TISSSDGSTY |
| 46 | CDR3 of hzME06v16 | REGLPLLLDTLWRQPVEYDY |
| 47 | CDR1 of hzMH07v3 | GLLFSIYDMN |
| 48 | CDR2 of hzMH07v3 | GITNNGYSTA |
| 49 | CDR3 of hzMH07v3 | DEWGREY |
| 50 | human IgG1 Fc region | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |

| SEQ ID NO | Description | Sequence |
|---|---|---|
| 51 | human IgG1 xELL Fc region | DKTHTCPPCPAPGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSL SPGK |
| 52 | Fc region M252Y and M428V (YV) S354C T366W knob | DKTHTCPPCP APELLGGPSV FLFPPKPKDT LYISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPCRDELTK NQVSLWCLVK GFYPSDIAVE WESNGQPENN YKTTPPVLDS DGSFFLYSKL TVDKSRWQQG NVFSCSVVHE ALHNHYTQKS LSLSPGK |
| 53 | Fc region M252Y, M428V, H435R (YVR) T366S, L368A, Y407V hole | DKTHTCPPCP APELLGGPSV FLFPPKPKDT LYISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVCT LPPSRDELTK NQVSLSCAVK GFYPSDIAVE WESNGQPENN YKTTPPVLDS DGSFFLVSKL TVDKSRWQQG NVFSCSVVHE ALHNRYTQKS LSLSPGK |
| 54 | Fc region xELL H435R | DKTHTC PPCPAPGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNRYTQK SLSLSPGK |
| 55 | Fc region xELL M252Y and M428V (YV) | DKTHTC PPCPAPGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNHYTQK SLSLSPGK |
| 56 | Fc region xELL M252Y and M428L (YL) | DKTHTC PPCPAPGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNHYTQK SLSLSPGK |
| 57 | Fc region xELL M252Y, M428L, H435R(YLR) | DKTHTC PPCPAPGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNRYTQK SLSLSPGK |
| 58 | Fc region xELL M252Y, M428V, H435R(YVR) | DKTHTC PPCPAPGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVVH EALHNRYTQK SLSLSPGK |
| 59 | Fc region xELL S354C T366W knob | DKTHTC PPCPAPGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCRDELT KNQVSLWCLV KGFYPSDIAV EWESNGQPEN NYKTTPPVLD SDGSFFLYSK LTVDKSRWQQ GNVFSCSVMH EALHNHYTQK SLSLSPGK |
| 60 | Fc region xELL H435R S354C T366W knob | DKTHTC PPCPAPGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCRDELT KNQVSLWCLV KGFYPSDIAV EWESNGQPEN NYKTTPPVLD SDGSFFLYSK LTVDKSRWQQ GNVFSCSVMH EALHNRYTQK SLSLSPGK |
| 61 | Fc region xELL M4252Y and M428V (YV) S354C T366W knob | DKTHTCPPCPAPGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVYTLPPCRDELTKNQVSLWCLVKGFYPSDIAVEWESNGQPE NNYKTTPPVLDSDGSFFLYSKLTVDKSRWQQGNVFSCSVVHEALHNHYTQKSLSL SPGK |
| 62 | Fc region xELL M252Y and M428L (YL) S354C T366W knob | DKTHTCPPCPAPGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVYTLPPCRDELTKNQVSLWCLVKGFYPSDIAVEWESNGQPE NNYKTTPPVLDSDGSFFLYSKLTVDKSRWQQGNVFSCSVLHEALHNHYTQKSLSL SPGK |

Table of Certain Sequences

| SEQ ID NO | Description | Sequence |
|---|---|---|
| 63 | Fc region xELL M252Y, M428L, H435R (YLR) S354C T366W knob | DKTHTCPPCPAPGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVYTLPPCRDELTKNQVSLWCLVKGFYPSDIAVEWESNGQPE NNYKTTPPVLDSDGSFFLYSKLTVDKSRWQQGNVFSCSVLHEALHNRYTQKSLSL SPGK |
| 64 | Fc region xELL M252Y, M428V, H435R (YVR) S354C T366W knob | DKTHTCPPCPAPGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVYTLPPCRDELTKNQVSLWCLVKGFYPSDIAVEWESNGQPE NNYKTTPPVLDSDGSFFLYSKLTVDKSRWQQGNVFSCSVVHEALHNRYTQKSLSL SPGK |
| 65 | Fc region xELL T366S, L368A, Y407V hole | DKTHTCPPCPAPGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVCTLPPSRDELTKNQVSLSCAVKGFYPSDIAVEWESNGQPE NNYKTTPPVLDSDGSFFLVSKLTVDKSRWQQGNVFSCSVMHEALHNHYTQKSLSL SPGK |
| 66 | Fc region xELL, H435R, T366S, L368A, Y407V hole | DKTHTCPPCPAPGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVCTLPPSRDELTKNQVSLSCAVKGFYPSDIAVEWESNGQPE NNYKTTPPVLDSDGSFFLVSKLTVDKSRWQQGNVFSCSVMHEALHNRYTQKSLSL SPGK |
| 67 | Fc region xELL M252Y and M428V (YV) T366S, L368A, Y407V hole | DKTHTCPPCPAPGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVCTLPPSRDELTKNQVSLSCAVKGFYPSDIAVEWESNGQPE NNYKTTPPVLDSDGSFFLVSKLTVDKSRWQQGNVFSCSVVHEALHNHYTQKSLSL SPGK |
| 68 | Fc region xELL M252Y and M428L (YL) T366S, L368A, Y407V hole | DKTHTCPPCPAPGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVCTLPPSRDELTKNQVSLSCAVKGFYPSDIAVEWESNGQPE NNYKTTPPVLDSDGSFFLVSKLTVDKSRWQQGNVFSCSVLHEALHNHYTQKSLSL SPGK |
| 69 | Fc region xELL M252Y, M428L, H435R (YLR) T366S, L368A, Y407V hole | DKTHTCPPCPAPGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVCTLPPSRDELTKNQVSLSCAVKGFYPSDIAVEWESNGQPE NNYKTTPPVLDSDGSFFLVSKLTVDKSRWQQGNVFSCSVLHEALHNRYTQKSLSL SPGK |
| 70 | Fc region xELL M252Y, M428V, H435R (YVR) T366S, L368A, Y407V hole | DKTHTCPPCPAPGGPSVFLFPPKPKDTLYISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVCTLPPSRDELTKNQVSLSCAVKGFYPSDIAVEWESNGQPE NNYKTTPPVLDSDGSFFLVSKLTVDKSRWQQGNVFSCSVVHEALHNRYTQKSLSL SPGK |
| 71 | Fc region H435R | DKTHTCPPCP APELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNRYTQK SLSLSPGK |
| 72 | Fc region M252Y and M428V (YV) | DKTHTCPPCP APELLGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVVH EALHNHYTQK SLSLSPGK |
| 73 | Fc region M252Y and | DKTHTCPPCP APELLGGPS VFLFPPKPKD TLYISRTPEV TCVVVDVSHE DPEVKFNWYV DGVEVHNAKT KPREEQYNST YRVVSVLTVL HQDWLNGKEY |

| SEQ ID NO | Description | Sequence |
|---|---|---|
| | M428L (YL) | KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNHYTQK SLSLSPGK |
| 74 | Fc region M252Y, M428L, H435R(YLR) | DKTHTCPPCP APELLGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVLH EALHNRYTQK SLSLSPGK |
| 75 | Fc region M252Y, M428V, H435R(YVR) | DKTHTCPPCP APELLGGPS VFLFPPKPKD TLYISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVVH EALHNRYTQK SLSLSPGK |
| 76 | Fc region S354C T366W knob | DKTHTCPPCP APELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCRDELT KNQVSLWCLV KGFYPSDIAV EWESNGQPEN NYKTTPPVLD SDGSFFLYSK LTVDKSRWQQ GNVFSCSVMH EALHNHYTQK SLSLSPGK |
| 77 | Fc region H435R S354C T366W knob | DKTHTCPPCP APELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCRDELT KNQVSLWCLV KGFYPSDIAV EWESNGQPEN NYKTTPPVLD SDGSFFLYSK LTVDKSRWQQ GNVFSCSVMH EALHNRYTQK SLSLSPGK |
| 78 | Fc region M252Y and M428L (YL) S354C T366W knob | DKTHTCPPCPAPELLGGPSVFLFPPKPKDTLYISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVLHEALHNHYTQKS LSLSPGK |
| 79 | Fc region M252Y, M428L, H435R (YLR) S354C T366W knob | DKTHTCPPCPAPELLGGPSVFLFPPKPKDTLYISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVLHEALHNRYTQKS LSLSPGK |
| 80 | Fc region M252Y, M428V, H435R (YVR) kS354C T366W knob | DKTHTCPPCPAPELLGGPSVFLFPPKPKDTLYISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVVHEALHNRYTQKS LSLSPGK |
| 81 | Fc region T366S, L368A, Y407V hole | DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVCTLPPSRDELTKNQVSLSCAVKGFYPSDIAVEWESNG QPENNYKTTPPVLDSDGSFFLVSKLTVDKSRWQQGNVFSCSVMHEALHNHYTQKS LSLSPGK |
| 82 | Fc region H435R, T366S, L368A, Y407V hole | DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVCTLPPSRDELTKNQVSLSCAVKGFYPSDIAVEWESNG QPENNYKTTPPVLDSDGSFFLVSKLTVDKSRWQQGNVFSCSVMHEALHNRYTQKS LSLSPGK |
| 83 | Fc region M252Y and M428V (YV) T366S, L368A, Y407V hole | DKTHTCPPCPAPELLGGPSVFLFPPKPKDTLYISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVCTLPPSRDELTKNQVSLSCAVKGFYPSDIAVEWESNG QPENNYKTTPPVLDSDGSFFLVSKLTVDKSRWQQGNVFSCSVVHEALHNHYTQKS LSLSPGK |
| 84 | Fc region M252Y and M428L (YL) T366S, L368A, Y407V hole | DKTHTCPPCPAPELLGGPSVFLFPPKPKDTLYISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVCTLPPSRDELTKNQVSLSCAVKGFYPSDIAVEWESNG QPENNYKTTPPVLDSDGSFFLVSKLTVDKSRWQQGNVFSCSVLHEALHNHYTQKS LSLSPGK |

| Table of Certain Sequences | | |
|---|---|---|
| SEQ ID NO | Description | Sequence |
| 85 | Fc region M252Y, M428L, H435R (YLR) T366S, L368A, Y407V hole | DKTHTCPPCPAPELLGGPSVFLFPPKPKDTLYISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVCTLPPSRDELTKNQVSLSCAVKGFYPSDIAVEWESNG QPENNYKTTPPVLDSDGSFFLVSKLTVDKSRWQQGNVFSCSVLHEALHNRYTQKS LSLSPGK |
| 86 | CLEC12a-ECD | TLKIEMKKMNKLQNISEELQRNISLQLMSNMNISNKIRNLSTTLQTIATKLCREL YSKEQEHCKPCPRRWIWHKDSCYFLSDDVQTWQESKMACAAQNASLLKINNKNA LEFIKSQSRSYDYWLGLSPEEDSTRGMRVDNIINSSAWVIRNAPDLNNMYCGYIN RLYVQYYHCTYKKRMICEKMANPVQLGSTYFREA |
| 87 | mFc-CLEC12a-ECD | LEVLFQGPGSPPLKECPPCAAPDLLGGPSVFIFPPKIKDVLMISLSPMVTCVVVD VSEDDPDVQISWFVNNVEVHTAQTQTHREDYNSTLRVVSALPIQHQDWMSGKEFK CKVNNRALPSPIEKTISKPRGPVRAPQVYVLPPPAEEMTKKEFSLTCMITGFLPA EIAVDWTSNGRTEQNYKNTATVLDSDGSYFMYSKLRVQKSTWERGSLFACSVVHE GLHNHLTTKTISRSLGKGGTGGSTLKIEMKKMNKLQNISEELQRNISLQLMSNMN ISNKIRNLSTTLQTIATKLCRELYSKEQEHCKPCPRRWIWHKDSCYFLSDDVQT WQESKMACAAQNASLLKINNKNALEFIKSQSRSYDYWLGLSPEEDSTRGMRVDNI INSSAWVIRNAPDLNNMYCGYINRLYVQYYHCTYKKRMICEKMANPVQLGSTYFR EA |

What is claimed is:

1. A polypeptide comprising at least one VHH domain that binds CLEC12a, wherein each VHH domain comprises a CDR1, a FR2, a CDR2, a FR3, and a CDR3, in that order, and wherein at least one VHH domain that binds CLEC12a comprises:
   a CDR1 comprising the amino acid sequence of SEQ ID NO: 32; a CDR2 comprising the amino acid sequence of SEQ ID NO: 33; and a CDR3 comprising the amino acid sequence of SEQ ID NO: 34 or 5.

2. The polypeptide of claim 1, wherein at least one VHH domain comprises a CDR1 comprising the amino acid sequence of SEQ ID NO: 32; a CDR2 comprising the amino acid sequence of SEQ ID NO: 33; and a CDR3 comprising the amino acid sequence of SEQ ID NO: 34.

3. The polypeptide of claim 1, wherein at least one VHH domain is humanized.

4. The polypeptide of claim 1, wherein at least one VHH domain that binds CLEC12a comprises an amino acid sequence at least 90% identical to the amino acid sequence of SEQ ID NO: 26 or 94.

5. The polypeptide of claim 1, wherein at least one VHH domain that binds CLEC12a comprises the amino acid sequence of SEQ ID NO: 26 or 94.

6. The polypeptide of claim 1, comprising one, two, or three VHH domains, wherein each VHH domain binds CLEC12a.

7. The polypeptide of claim 6, wherein at least one VHH domain that binds CLEC12a comprises the amino acid sequence of SEQ ID NO: 26 or 94.

8. The polypeptide of claim 1, wherein the polypeptide comprises at least one binding domain that binds an antigen other than CLEC12a, wherein the at least one binding domain binds CD3, T-cell receptor (TCR)α, TCRβ, CD28, CD16, CD32A, CD64, CD89, NKp46, or NKG2D.

9. The polypeptide of claim 8, wherein at least one VHH domain that binds CLEC12a comprises the amino acid sequence of SEQ ID NO: 26 or 94.

10. The polypeptide of claim 1, wherein the polypeptide comprises an Fc region.

11. The polypeptide of claim 10, wherein the Fc region comprises an amino acid sequence selected from SEQ ID NOs: 50 to 85.

12. The polypeptide of claim 10, which is a homodimer under physiological conditions.

13. An immunoconjugate comprising the polypeptide of claim 1 linked to a cytotoxic agent.

14. The immunoconjugate of claim 13, wherein the cytotoxic agent is selected from a calicheamicin, an auristatin, a dolastatin, a tubulicin, a maytansinoid, a cryptophycin, a duocarmycin, an esperamicin, a pyrrolobenzodiazepine, and an enediyne antibiotic.

15. The immunoconjugate of claim 13, wherein at least one VHH domain that binds CLEC12a comprises an amino acid sequence at least 95% identical to the amino acid sequence of SEQ ID NO: 26 or 94.

16. A method of inhibiting or slowing the progression of cancer comprising administering to a subject with cancer a pharmaceutically effective amount of the immunoconjugate of claim 15, wherein the cancer is selected from chronic lymphocytic leukemia (CLL); acute lymphoblastic leukemia (ALL); acute myeloid leukemia (AML); Hairy cell leukemia; and chronic myeloblastic leukemia.

17. The method of claim 16, wherein the cytotoxic agent is selected from a calicheamicin, an auristatin, a dolastatin, a tubulicin, a maytansinoid, a cryptophycin, a duocarmycin, an esperamicin, a pyrrolobenzodiazepine, and an enediyne antibiotic.

18. The method of claim 17, wherein the polypeptide comprises at least one VHH domain that binds CLEC12a comprising the amino acid sequence of SEQ ID NO: 26 or 94.

19. The method of claim 16, wherein the polypeptide comprises at least one VHH domain that binds CLEC12a comprising the amino acid sequence of SEQ ID NO: 26 or 94.

20. The immunoconjugate of claim 13, wherein at least one VHH domain that binds CLEC12a comprises an amino acid sequence at least 90% identical to the amino acid sequence of SEQ ID NO: 26 or 94.

21. A pharmaceutical composition comprising the polypeptide of claim 1, and a pharmaceutically acceptable carrier.

22. The polypeptide of claim 1, wherein at least one VHH domain that binds CLEC12a comprises an amino acid sequence at least 95% identical to the amino acid sequence of SEQ ID NO: 26 or 94.

23. A method of inhibiting or slowing the progression of cancer comprising administering to a subject with cancer a pharmaceutically effective amount of a polypeptide comprising at least one VHH domain that binds CLEC12a, and wherein at least one VHH domain that binds CLEC12a comprises a CDR1 comprising the amino acid sequence of SEQ ID NO: 32; a CDR2 comprising the amino acid sequence of SEQ ID NO: 33; and a CDR3 comprising the amino acid sequence of SEQ ID NO: 34 or 5, and is at least 95% identical to the amino acid sequence of SEQ ID NO: 26 or 94, wherein the polypeptide comprises at least one binding domain that binds an antigen other than CLEC12a, wherein the at least one binding domain binds CD3, T-cell receptor (TCR)α, TCRβ, CD28, CD16, CD32A, CD64, CD89, NKp46, or NKG2D; and wherein the cancer is selected from chronic lymphocytic leukemia (CLL); acute lymphoblastic leukemia (ALL); acute myeloid leukemia (AML); Hairy cell leukemia; and chronic myeloblastic leukemia.

24. The method of claim 23, further comprising administering an additional therapy or therapeutic agent.

25. The method of claim 24, wherein the additional therapy or therapeutic agent is an anti-cancer therapy or agent, wherein the anti-cancer therapy or agent is selected from a chemotherapeutic agent, an anti-cancer biologic, radiation therapy, CAR-T therapy, and an oncolytic virus.

26. The method of claim 23, wherein at least one VHH domain that binds CLEC12a comprises a CDR1 comprising the amino acid sequence of SEQ ID NO: 32; a CDR2 comprising the amino acid sequence of SEQ ID NO: 33; and a CDR3 comprising the amino acid sequence of SEQ ID NO: 34.

27. The method of claim 23, wherein at least one VHH domain that binds CLEC12a comprises the amino acid sequence of SEQ ID NO: 26 or 94.

\* \* \* \* \*

SEQUENCE LISTING

<160> NUMBER OF SEQ ID NOS: 99

<210> SEQ ID NO 1
<211> LENGTH: 265
<212> TYPE: PRT
<213> ORGANISM: Homo sapiens

<400> SEQUENCE: 1

```
Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
    130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
```

```
                    180                 185                 190
Leu Ser Pro Glu Glu Asp Ser Thr Arg Gly Met Arg Val Asp Asn Ile
            195                 200                 205

Ile Asn Ser Ser Ala Trp Val Ile Arg Asn Ala Pro Asp Leu Asn Asn
    210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
                245                 250                 255

Leu Gly Ser Thr Tyr Phe Arg Glu Ala
            260                 265

<210> SEQ ID NO 2
<211> LENGTH: 118
<212> TYPE: PRT
<213> ORGANISM: Artificial Sequence
<220> FEATURE:
<223> OTHER INFORMATION: MB11

<400> SEQUENCE: 2

Gln Val Gln Leu Gln Gln Ser Gly Gly Gly Leu Val Gln Pro Gly Gly
1               5                   10                  15

Ser Leu Arg Leu Ser Cys Val Ala Ser Gly Phe Leu Phe Ser Ile Tyr
            20                  25                  30

Asp Met Asn Trp Tyr Arg Gln Ala Pro Gly Lys Glu Arg Glu Trp Ile
        35                  40                  45

Ala Gly Ile Thr Asn Asn Gly Tyr Ser Thr Ala Tyr Thr Asp Ser Val
    50                  55                  60

Gln Gly Arg Phe Thr Ile Ser Arg Asp Asn Ala Lys Asn Thr Ile Tyr
65                  70                  75                  80

Leu Gln Met Thr Ser Leu Lys Pro Glu Asp Thr Ala Val Tyr Tyr Cys
                85                  90                  95

His Ala Asp Leu Thr Lys Cys Tyr Asp Gly Glu Tyr Ala Trp Gly Gln
            100                 105                 110

Gly Thr Gln Val Thr Val
        115

<210> SEQ ID NO 3
<211> LENGTH: 10
<212> TYPE: PRT
<213> ORGANISM: Artificial Sequence
<220> FEATURE:
<223> OTHER INFORMATION: MB11 CDR1

<400> SEQUENCE: 3

Gly Phe Leu Phe Ser Ile Tyr Asp Met Asn
1               5                   10

<210> SEQ ID NO 4
<211> LENGTH: 10
<212> TYPE: PRT
<213> ORGANISM: Artificial Sequence
<220> FEATURE:
<223> OTHER INFORMATION: MB11 CDR2

<400> SEQUENCE: 4

Gly Ile Thr Asn Asn Gly Tyr Ser Thr Ala
1               5                   10

<210> SEQ ID NO 5
```

```
<211> LENGTH: 11
<212> TYPE: PRT
<213> ORGANISM: Artificial Sequence
<220> FEATURE:
<223> OTHER INFORMATION: MB11 CDR3

<400> SEQUENCE: 5

Asp Leu Thr Lys Cys Tyr Asp Gly Glu Tyr Ala
1               5                   10

<210> SEQ ID NO 6
<211> LENGTH: 117
<212> TYPE: PRT
<213> ORGANISM: Artificial Sequence
<220> FEATURE:
<223> OTHER INFORMATION: MC02

<400> SEQUENCE: 6

Gln Val Gln Leu Val Gln Ser Gly Gly Gly Leu Ala Gln Pro Gly Gly
1               5                   10                  15

Ser Leu Arg Leu Ser Cys Thr Ala Ser Gly Phe Thr Phe Arg Ile Asn
            20                  25                  30

Asp Met Gly Trp Tyr Arg Gln Ala Pro Gly Lys Glu Cys Glu Met Val
        35                  40                  45

Ala Gly Ile Ser Asn Asn Gly Phe Ser Thr Ala Tyr Ala Asp Ser Val
    50                  55                  60

Lys Gly Arg Phe Thr Ile Ser Arg Asp Asn Ala Lys Asn Thr Val Ser
65                  70                  75                  80

Leu Gln Met Asp Ser Leu Lys Ser Glu Asp Thr Ala Val Tyr Tyr Cys
                85                  90                  95

His Arg Thr Asp Asp Gly Ala Ala His Ala Cys Ser Arg Gly Gln Gly
            100                 105                 110

Thr Gln Val Thr Val
        115

<210> SEQ ID NO 7
<211> LENGTH: 10
<212> TYPE: PRT
<213> ORGANISM: Artificial Sequence
<220> FEATURE:
<223> OTHER INFORMATION: MC02 CDR1

<400> SEQUENCE: 7

Gly Phe Thr Phe Arg Ile Asn Asp Met Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: MC02 CDR2

<400> SEQUENCE: 8

Gly Ile Ser Asn Asn Gly Phe Ser Thr Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: MC02 CDR3
```

```
<400> SEQUENCE: 9

Thr Asp Asp Gly Ala Ala His Ala Cys Ser
1               5                   10

<210> SEQ ID NO 10
<211> LENGTH: 119
<212> TYPE: PRT
<213> ORGANISM: Artificial Sequence
<220> FEATURE:
<223> OTHER INFORMATION: MC06

<400> SEQUENCE: 10

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Asp Met Asn Trp Tyr Arg Gln Thr Pro Gly Lys Glu Arg Glu Trp Val
        35                  40                  45

Ala Gly Ile Ser Asn Asn Gly Phe Ser Thr Ala Tyr Ala Gly Ser Val
    50                  55                  60

Lys Gly Arg Phe Thr Ile Ser Arg Asp Asn Ala Glu Asn Thr Val Tyr
65                  70                  75                  80

Leu Gln Met Asn Ser Leu Lys Ser Glu Asp Thr Ala Val Tyr Tyr Cys
                85                  90                  95

Asn Leu Asp Val His Gly Arg Val Gly Ala Gln Gly Asp Tyr Trp Gly
            100                 105                 110

Gln Gly Thr Gln Val Thr Val
        115

<210> SEQ ID NO 11
<211> LENGTH: 10
<212> TYPE: PRT
<213> ORGANISM: Artificial Sequence
<220> FEATURE:
<223> OTHER INFORMATION: MC06 CDR1

<400> SEQUENCE: 11

Gly Phe Thr Phe Ser Val Tyr Asp Met Asn
1               5                   10

<210> SEQ ID NO 12
<211> LENGTH: 10
<212> TYPE: PRT
<213> ORGANISM: Artificial Sequence
<220> FEATURE:
<223> OTHER INFORMATION: MC06 CDR2

<400> SEQUENCE: 12

Gly Ile Ser Asn Asn Gly Phe Ser Thr Ala
1               5                   10

<210> SEQ ID NO 13
<211> LENGTH: 12
<212> TYPE: PRT
<213> ORGANISM: Artificial Sequence
<220> FEATURE:
<223> OTHER INFORMATION: MC06 CDR3

<400> SEQUENCE: 13

Asp Val His Gly Arg Val Gly Ala Gln Gly Asp Tyr
1               5                   10
```

```
<210> SEQ ID NO 14
<211> LENGTH: 110
<212> TYPE: PRT
<213> ORGANISM: Artificial Sequence
<220> FEATURE:
<223> OTHER INFORMATION: ME02

<400> SEQUENCE: 14

Gln Val Gln Leu Gln Gln Ser Gly Gly Leu Val Gln Val Gly Gly
1               5                   10                  15

Ser Gln Arg Leu Ser Cys Ala Ala Ser Gly Arg Thr Phe Glu Tyr Asp
            20                  25                  30

Asp Met Val Trp Phe Arg Gln Ala Pro Gly Lys Glu Arg Glu Val
        35                  40                  45

Ala Gly Ile Ser Trp Ser Gly Gly Ser Ile Tyr Tyr Ala Asp Ser Val
        50                  55                  60

Lys Gly Arg Phe Ser Ile Ser Arg Asp Asn Ala Lys Asn Thr Val Tyr
65                  70                  75                  80

Leu Glu Met Asn Arg Leu Lys Pro Glu Asp Thr Ala Val Tyr Tyr Cys
                85                  90                  95

Asn Val Gly Ser Tyr Trp Gly Gln Gly Thr Gln Val Thr Val
                100                 105                 110

<210> SEQ ID NO 15
<211> LENGTH: 10
<212> TYPE: PRT
<213> ORGANISM: Artificial Sequence
<220> FEATURE:
<223> OTHER INFORMATION: ME02 CDR1

<400> SEQUENCE: 15

Gly Arg Thr Phe Glu Tyr Asp Asp Met Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: ME02 CDR2

<400> SEQUENCE: 16

Gly Ile Ser Trp Ser Gly Gly Ser Ile Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: ME02 CDR3

<400> SEQUENCE: 17

Gly Ser Tyr
1

<210> SEQ ID NO 18
<211> LENGTH: 127
<212> TYPE: PRT
<213> ORGANISM: Artificial Sequence
<220> FEATURE:
<223> OTHER INFORMATION: ME06

<400> SEQUENCE: 18
```

```
Gln Val Gln Leu Val Gln Ser Gly Gly Gly Leu Val Gln Ala Gly Gly
1               5                   10                  15

Ser Leu Arg Leu Ser Cys Val Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Ile Ser Asn Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu His Val Asn Ser Leu Asn Pro Glu Asp Thr Ala Val Tyr Tyr Cys
                85                  90                  95

Ala Leu Arg Glu Gly Leu Pro Leu Leu Leu Asp Ser Leu Trp Arg Gln
            100                 105                 110

Pro Val Glu Tyr Asp Tyr Trp Gly Gln Gly Thr Gln Val Thr Val
            115                 120                 125
```

<210> SEQ ID NO 19
<211> LENGTH: 10
<212> TYPE: PRT
<213> ORGANISM: Artificial Sequence
<220> FEATURE:
<223> OTHER INFORMATION: ME06 CDR1

<400> SEQUENCE: 19

```
Gly Phe Thr Phe Asp Asp Tyr Ala Ile Gly
1               5                   10
```

<210> SEQ ID NO 20
<211> LENGTH: 10
<212> TYPE: PRT
<213> ORGANISM: Artificial Sequence
<220> FEATURE:
<223> OTHER INFORMATION: ME06 CDR2

<400> SEQUENCE: 20

```
Cys Ile Ser Asn Ser Asp Gly Ser Thr Tyr
1               5                   10
```

<210> SEQ ID NO 21
<211> LENGTH: 20
<212> TYPE: PRT
<213> ORGANISM: Artificial Sequence
<220> FEATURE:
<223> OTHER INFORMATION: ME06 CDR3

<400> SEQUENCE: 21

```
Arg Glu Gly Leu Pro Leu Leu Leu Asp Ser Leu Trp Arg Gln Pro Val
1               5                   10                  15

Glu Tyr Asp Tyr
            20
```

<210> SEQ ID NO 22
<211> LENGTH: 114
<212> TYPE: PRT
<213> ORGANISM: Artificial Sequence
<220> FEATURE:
<223> OTHER INFORMATION: MH07

<400> SEQUENCE: 22

```
Gln Val Gln Leu Val Gln Ser Gly Gly Gly Leu Val Gln Pro Gly Gly
1               5                   10                  15
```

-continued

Ser Leu Arg Leu Ser Cys Val Ala Ser Gly Leu Phe Ser Ile Tyr
            20                  25                  30

Asp Met Asn Trp Tyr Arg Gln Ala Pro Gly Lys Glu Arg Glu Trp Ile
            35                  40                  45

Ala Gly Ile Thr Asn Asn Gly Tyr Ser Thr Ala Tyr Thr Asp Ser Val
        50                  55                  60

Gln Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

His Thr Asp Glu Trp Gly Arg Glu Tyr Trp Gly Gln Gly Thr Gln Val
            100                 105                 110

Thr Val

<210> SEQ ID NO 23
<211> LENGTH: 10
<212> TYPE: PRT
<213> ORGANISM: Artificial Sequence
<220> FEATURE:
<223> OTHER INFORMATION: MH07 CDR1

<400> SEQUENCE: 23

Gly Leu Leu Phe Ser Ile Tyr Asp Met Asn
1               5                   10

<210> SEQ ID NO 24
<211> LENGTH: 10
<212> TYPE: PRT
<213> ORGANISM: Artificial Sequence
<220> FEATURE:
<223> OTHER INFORMATION: MH07 CDR2

<400> SEQUENCE: 24

Gly Ile Thr Asn Asn Gly Tyr Ser Thr Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: MH07 CDR3

<400> SEQUENCE: 25

Asp Glu Trp Gly Arg Glu Tyr
1               5

<210> SEQ ID NO 26
<211> LENGTH: 118
<212> TYPE: PRT
<213> ORGANISM: Artificial Sequence
<220> FEATURE:
<223> OTHER INFORMATION: hzMB11v13

<400> SEQUENCE: 26

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Leu Phe Ser Ile Tyr
            20                  25                  30

Asp Met Asn Trp Tyr Arg Gln Ala Pro Gly Lys Glu Arg Glu Trp Val
            35                  40                  45

Ala Gly Ile Thr Asn Asn Gly Tyr Ser Thr Ala Tyr Ala Glu Ser Val
        50                  55                  60

```
                    50                  55                  60
Lys Gly Arg Phe Thr Ile Ser Arg Asp Asn Ala Lys Asn Thr Ile Tyr
 65                  70                  75                  80

Leu Gln Met Ser Ser Leu Arg Ala Glu Asp Thr Ala Val Tyr Tyr Cys
                    85                  90                  95

His Ala Asp Leu Thr Lys Ala Tyr Asp Val Tyr Ala Trp Gly Gln
                    100                 105                 110

Gly Thr Leu Val Thr Val
            115

<210> SEQ ID NO 27
<211> LENGTH: 117
<212> TYPE: PRT
<213> ORGANISM: Artificial Sequence
<220> FEATURE:
<223> OTHER INFORMATION: hzMC02v6

<400> SEQUENCE: 27

Glu Val Gln Leu Val Glu Ser Gly Gly Gly Val Gln Pro Gly Gly
 1               5                  10                  15

Ser Leu Arg Leu Ser Cys Ala Ala Ser Gly Phe Thr Phe Arg Ile Asn
                 20                  25                  30

Asp Met Gly Trp Tyr Arg Gln Ala Pro Gly Lys Glu Cys Glu Met Val
                 35                  40                  45

Ala Gly Ile Ser Asn Asn Gly Phe Ser Thr Ala Tyr Ala Glu Ser Val
                 50                  55                  60

Lys Gly Arg Phe Thr Ile Ser Arg Asp Asn Ala Lys Asn Thr Val Tyr
 65                  70                  75                  80

Leu Gln Met Ser Ser Leu Arg Ala Glu Asp Thr Ala Val Tyr Tyr Cys
                    85                  90                  95

His Arg Thr Asp Glu Gly Ala Ala His Ala Cys Ser Arg Gly Gln Gly
                    100                 105                 110

Thr Leu Val Thr Val
            115

<210> SEQ ID NO 28
<211> LENGTH: 119
<212> TYPE: PRT
<213> ORGANISM: Artificial Sequence
<220> FEATURE:
<223> OTHER INFORMATION: hzMC06v2

<400> SEQUENCE: 28

Glu Val Gln Leu Val Glu Ser Gly Gly Gly Val Gln Pro Gly Gly
 1               5                  10                  15

Ser Leu Arg Leu Ser Cys Ala Ala Ser Gly Phe Thr Phe Ser Val Tyr
                 20                  25                  30

Asp Met Asn Trp Tyr Arg Gln Ala Pro Gly Lys Glu Arg Glu Trp Val
                 35                  40                  45

Ser Gly Ile Ser Asn Asn Gly Phe Ser Thr Ala Tyr Ala Glu Ser Val
                 50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ala Glu Asp Thr Ala Val Tyr Tyr Cys
                    85                  90                  95

Asn Leu Asp Val His Gly Arg Val Gly Ala Gln Gly Asp Tyr Trp Gly
                    100                 105                 110
```

```
Gln Gly Thr Leu Val Thr Val
        115

<210> SEQ ID NO 29
<211> LENGTH: 110
<212> TYPE: PRT
<213> ORGANISM: Artificial Sequence
<220> FEATURE:
<223> OTHER INFORMATION: hzME02v4

<400> SEQUENCE: 29

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Thr Phe Glu Tyr Asp
            20                  25                  30

Asp Met Val Trp Phe Arg Gln Ala Pro Gly Lys Glu Arg Glu Val
        35                  40                  45

Ala Gly Ile Ser Trp Ser Gly Gly Ser Ile Tyr Tyr Ala Glu Ser Val
    50                  55                  60

Lys Gly Arg Phe Ser Ile Ser Arg Asp Asn Ala Lys Asn Thr Val Tyr
65                  70                  75                  80

Leu Glu Met Asn Arg Leu Lys Pro Glu Asp Thr Ala Val Tyr Tyr Cys
                85                  90                  95

Asn Val Gly Ser Tyr Trp Gly Gln Gly Thr Leu Val Thr Val
            100                 105                 110

<210> SEQ ID NO 30
<211> LENGTH: 127
<212> TYPE: PRT
<213> ORGANISM: Artificial Sequence
<220> FEATURE:
<223> OTHER INFORMATION: hzME06v16

<400> SEQUENCE: 30

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Thr Ile Ser Ser Ser Asp Gly Ser Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Leu Arg Glu Gly Leu Pro Leu Leu Leu Asp Thr Leu Trp Arg Gln
            100                 105                 110

Pro Val Glu Tyr Asp Tyr Trp Gly Gln Gly Thr Gln Val Thr Val
        115                 120                 125

<210> SEQ ID NO 31
<211> LENGTH: 114
<212> TYPE: PRT
<213> ORGANISM: Artificial Sequence
<220> FEATURE:
<223> OTHER INFORMATION: hzMH07v3

<400> SEQUENCE: 31

Glu Val Gln Leu Val Glu Ser Gly Gly Gly Glu Val Gln Pro Gly Gly
```

```
                1               5                  10                 15
Ser Leu Arg Leu Ser Cys Ala Ala Ser Gly Leu Leu Phe Ser Ile Tyr
                20                 25                 30

Asp Met Asn Trp Tyr Arg Gln Ala Pro Gly Lys Glu Arg Glu Trp Val
                35                 40                 45

Ala Gly Ile Thr Asn Asn Gly Tyr Ser Thr Ala Tyr Ala Glu Ser Val
        50                 55                 60

Lys Gly Arg Phe Thr Ile Ser Arg Asp Asn Ala Lys Asn Thr Val Tyr
65                  70                 75                 80

Leu Gln Met Ser Ser Leu Arg Ala Glu Asp Thr Ala Val Tyr Tyr Cys
                85                 90                 95

His Thr Asp Glu Trp Gly Arg Glu Tyr Trp Gly Gln Gly Thr Leu Val
                100                105                110

Thr Val

<210> SEQ ID NO 32
<211> LENGTH: 10
<212> TYPE: PRT
<213> ORGANISM: Artificial Sequence
<220> FEATURE:
<223> OTHER INFORMATION: CDR1 of hzMB11v13

<400> SEQUENCE: 32

Gly Phe Leu Phe Ser Ile Tyr Asp Met Asn
1               5                   10

<210> SEQ ID NO 33
<211> LENGTH: 10
<212> TYPE: PRT
<213> ORGANISM: Artificial Sequence
<220> FEATURE:
<223> OTHER INFORMATION: CDR2 of hzMB11v13

<400> SEQUENCE: 33

Gly Ile Thr Asn Asn Gly Tyr Ser Thr Ala
1               5                   10

<210> SEQ ID NO 34
<211> LENGTH: 11
<212> TYPE: PRT
<213> ORGANISM: Artificial Sequence
<220> FEATURE:
<223> OTHER INFORMATION: CDR3 of hzMB11v13

<400> SEQUENCE: 34

Asp Leu Thr Lys Ala Tyr Asp Val Glu Tyr Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: CDR1 of hzMC02v6

<400> SEQUENCE: 35

Gly Phe Thr Phe Arg Ile Asn Asp Met Gly
1               5                   10

<210> SEQ ID NO 36
<211> LENGTH: 10
<212> TYPE: PRT
<213> ORGANISM: Artificial Sequence
```

```
<220> FEATURE:
<223> OTHER INFORMATION: CDR2 of hzMC02v6

<400> SEQUENCE: 36

Gly Ile Ser Asn Asn Gly Phe Ser Thr Ala
1               5                   10

<210> SEQ ID NO 37
<211> LENGTH: 10
<212> TYPE: PRT
<213> ORGANISM: Artificial Sequence
<220> FEATURE:
<223> OTHER INFORMATION: CDR3 of hzMC02v6

<400> SEQUENCE: 37

Thr Asp Glu Gly Ala Ala His Ala Cys Ser
1               5                   10

<210> SEQ ID NO 38
<211> LENGTH: 10
<212> TYPE: PRT
<213> ORGANISM: Artificial Sequence
<220> FEATURE:
<223> OTHER INFORMATION: CDR1 of hzMC06v2

<400> SEQUENCE: 38

Gly Phe Thr Phe Ser Val Tyr Asp Met Asn
1               5                   10

<210> SEQ ID NO 39
<211> LENGTH: 10
<212> TYPE: PRT
<213> ORGANISM: Artificial Sequence
<220> FEATURE:
<223> OTHER INFORMATION: CDR2 of hzMC06v2

<400> SEQUENCE: 39

Gly Ile Ser Asn Asn Gly Phe Ser Thr Ala
1               5                   10

<210> SEQ ID NO 40
<211> LENGTH: 12
<212> TYPE: PRT
<213> ORGANISM: Artificial Sequence
<220> FEATURE:
<223> OTHER INFORMATION: CDR3 of hzMC06v2

<400> SEQUENCE: 40

Asp Val His Gly Arg Val Gly Ala Gln Gly Asp Tyr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: CDR1 of hzME02v4

<400> SEQUENCE: 41

Gly Arg Thr Phe Glu Tyr Asp Asp Met Val
1               5                   10

<210> SEQ ID NO 42
<211> LENGTH: 10
<212> TYPE: PRT
<213> ORGANISM: Artificial Sequence
<220> FEATURE:
```

<223> OTHER INFORMATION: CDR2 of hzME02v4

<400> SEQUENCE: 42

Gly Ile Ser Trp Ser Gly Gly Ser Ile Tyr
1               5                   10

<210> SEQ ID NO 43
<211> LENGTH: 3
<212> TYPE: PRT
<213> ORGANISM: Artificial Sequence
<220> FEATURE:
<223> OTHER INFORMATION: CDR3 of hzME02v4

<400> SEQUENCE: 43

Gly Ser Tyr
1

<210> SEQ ID NO 44
<211> LENGTH: 10
<212> TYPE: PRT
<213> ORGANISM: Artificial Sequence
<220> FEATURE:
<223> OTHER INFORMATION: CDR1 of hzME06v16

<400> SEQUENCE: 44

Gly Phe Thr Phe Asp Asp Tyr Ala Ile Gly
1               5                   10

<210> SEQ ID NO 45
<211> LENGTH: 10
<212> TYPE: PRT
<213> ORGANISM: Artificial Sequence
<220> FEATURE:
<223> OTHER INFORMATION: CDR2 of hzME06v16

<400> SEQUENCE: 45

Thr Ile Ser Ser Ser Asp Gly Ser Thr Tyr
1               5                   10

<210> SEQ ID NO 46
<211> LENGTH: 20
<212> TYPE: PRT
<213> ORGANISM: Artificial Sequence
<220> FEATURE:
<223> OTHER INFORMATION: CDR3 of hzME06v16

<400> SEQUENCE: 46

Arg Glu Gly Leu Pro Leu Leu Leu Asp Thr Leu Trp Arg Gln Pro Val
1               5                   10                  15

Glu Tyr Asp Tyr
            20

<210> SEQ ID NO 47
<211> LENGTH: 10
<212> TYPE: PRT
<213> ORGANISM: Artificial Sequence
<220> FEATURE:
<223> OTHER INFORMATION: CDR1 of hzMH07v3

<400> SEQUENCE: 47

Gly Leu Leu Phe Ser Ile Tyr Asp Met Asn
1               5                   10

<210> SEQ ID NO 48
<211> LENGTH: 10
<212> TYPE: PRT

```
<213> ORGANISM: Artificial Sequence
<220> FEATURE:
<223> OTHER INFORMATION: CDR2 of hzMH07v3

<400> SEQUENCE: 48

Gly Ile Thr Asn Asn Gly Tyr Ser Thr Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: CDR3 of hzMH07v3

<400> SEQUENCE: 49

Asp Glu Trp Gly Arg Glu Tyr
1               5

<210> SEQ ID NO 50
<211> LENGTH: 227
<212> TYPE: PRT
<213> ORGANISM: Homo sapiens

<400> SEQUENCE: 50

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 51
<211> LENGTH: 224
<212> TYPE: PRT
```

<213> ORGANISM: Artificial Sequence
<220> FEATURE:
<223> OTHER INFORMATION: human IgG1 xELL Fc region

<400> SEQUENCE: 51

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65              70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220
```

<210> SEQ ID NO 52
<211> LENGTH: 227
<212> TYPE: PRT
<213> ORGANISM: Artificial Sequence
<220> FEATURE:
<223> OTHER INFORMATION: Fc region M252Y and M428V (YV) S354C T366W knob

<400> SEQUENCE: 52

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

-continued

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
            195                 200                 205

His Glu Ala Leu His Asn His Tyr Thr Gln Lys Ser Leu Ser Leu Ser
    210                 215                 220

Pro Gly Lys
225

<210> SEQ ID NO 53
<211> LENGTH: 227
<212> TYPE: PRT
<213> ORGANISM: Artificial Sequence
<220> FEATURE:
<223> OTHER INFORMATION: Fc region M252Y, M428V, H435R (YVR) T366S,
      L368A, Y407V hole

<400> SEQUENCE: 53

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
            195                 200                 205

His Glu Ala Leu His Asn Arg Tyr Thr Gln Lys Ser Leu Ser Leu Ser
    210                 215                 220

Pro Gly Lys
225

<210> SEQ ID NO 54
<211> LENGTH: 224
<212> TYPE: PRT
<213> ORGANISM: Artificial Sequence
<220> FEATURE:
<223> OTHER INFORMATION: Fc region xELL H435R

<400> SEQUENCE: 54

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Gly Lys
    210                 215                 220

<210> SEQ ID NO 55
<211> LENGTH: 224
<212> TYPE: PRT
<213> ORGANISM: Artificial Sequence
<220> FEATURE:
<223> OTHER INFORMATION: Fc region xELL M252Y and M428V (YV)

<400> SEQUENCE: 55

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr

```
                    85                  90                  95
Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Ser Arg Asp Glu Leu Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Val His Glu Ala
                195                 200                 205

Leu His Asn His Tyr Thr Gln Lys Ser Leu Ser Leu Ser Pro Gly Lys
                210                 215                 220
```

<210> SEQ ID NO 56
<211> LENGTH: 224
<212> TYPE: PRT
<213> ORGANISM: Artificial Sequence
<220> FEATURE:
<223> OTHER INFORMATION: Fc region xELL M252Y and M428L (YL)

<400> SEQUENCE: 56

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Ser Arg Asp Glu Leu Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Leu His Glu Ala
                195                 200                 205

Leu His Asn His Tyr Thr Gln Lys Ser Leu Ser Leu Ser Pro Gly Lys
                210                 215                 220
```

```
<210> SEQ ID NO 57
<211> LENGTH: 224
<212> TYPE: PRT
<213> ORGANISM: Artificial Sequence
<220> FEATURE:
<223> OTHER INFORMATION: Fc region xELL M252Y, M428L, H435R (YLR)

<400> SEQUENCE: 57
```

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Leu His Glu Ala
        195                 200                 205

Leu His Asn Arg Tyr Thr Gln Lys Ser Leu Ser Leu Ser Pro Gly Lys
    210                 215                 220

```
<210> SEQ ID NO 58
<211> LENGTH: 224
<212> TYPE: PRT
<213> ORGANISM: Artificial Sequence
<220> FEATURE:
<223> OTHER INFORMATION: Fc region xELL M252Y, M428V, H435R (YVR)

<400> SEQUENCE: 58
```

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

```
Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Ser Arg Asp Glu Leu Thr Lys Asn Gln Val Ser Leu Thr Cys
        130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro Gly Lys
210                 215                 220
```

```
<210> SEQ ID NO 59
<211> LENGTH: 224
<212> TYPE: PRT
<213> ORGANISM: Artificial Sequence
<220> FEATURE:
<223> OTHER INFORMATION: Fc region xELL S354C T366W knob

<400> SEQUENCE: 59
```

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Cys Arg Asp Glu Leu Thr Lys Asn Gln Val Ser Leu Trp Cys
        130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
210                 215                 220
```

```
<210> SEQ ID NO 60
<211> LENGTH: 224
```

```
<212> TYPE: PRT
<213> ORGANISM: Artificial Sequence
<220> FEATURE:
<223> OTHER INFORMATION: Fc region xELL H435R S354C T366W knob

<400> SEQUENCE: 60

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Gly Lys
    210                 215                 220

<210> SEQ ID NO 61
<211> LENGTH: 224
<212> TYPE: PRT
<213> ORGANISM: Artificial Sequence
<220> FEATURE:
<223> OTHER INFORMATION: Fc region xELL M252Y and M428V (YV) S354C T366W
      knob

<400> SEQUENCE: 61

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
```

```
            100                 105                 110
Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Gly Lys
    210                 215                 220
```

<210> SEQ ID NO 62
<211> LENGTH: 224
<212> TYPE: PRT
<213> ORGANISM: Artificial Sequence
<220> FEATURE:
<223> OTHER INFORMATION: Fc region xELL M252Y and M428L (YL) S354C T366W knob

<400> SEQUENCE: 62

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
            85                  90                  95

Lys Cys Lys Val Ser Asn Lys Ala Leu Pro Ala Pro Ile Glu Lys Thr
        100                 105                 110

Ile Ser Lys Ala Lys Gly Gln Pro Arg Glu Pro Gln Val Tyr Thr Leu
    115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Leu His Glu Ala
        195                 200                 205

Leu His Asn His Tyr Thr Gln Lys Ser Leu Ser Leu Ser Pro Gly Lys
    210                 215                 220
```

<210> SEQ ID NO 63
<211> LENGTH: 224

```
<212> TYPE: PRT
<213> ORGANISM: Artificial Sequence
<220> FEATURE:
<223> OTHER INFORMATION: Fc region xELL M252Y, M428L, H435R (YLR) S354C
      T366W knob

<400> SEQUENCE: 63

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Asp Val Ser His Glu Asp Pro
        35                  40                  45

Glu Val Lys Phe Asn Trp Tyr Val Asp Gly Val Glu Val His Asn Ala
50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Leu His Glu Ala
        195                 200                 205

Leu His Asn Arg Tyr Thr Gln Lys Ser Leu Ser Leu Ser Pro Gly Lys
210                 215                 220

<210> SEQ ID NO 64
<211> LENGTH: 224
<212> TYPE: PRT
<213> ORGANISM: Artificial Sequence
<220> FEATURE:
<223> OTHER INFORMATION: Fc region xELL M252Y, M428V, H435R (YVR) S354C
      T366W knob

<400> SEQUENCE: 64

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Asp Val Ser His Glu Asp Pro
        35                  40                  45

Glu Val Lys Phe Asn Trp Tyr Val Asp Gly Val Glu Val His Asn Ala
50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95
```

```
Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
            195                 200                 205

Leu His Asn Arg Tyr Thr Gln Lys Ser Leu Ser Leu Ser Pro Gly Lys
        210                 215                 220

<210> SEQ ID NO 65
<211> LENGTH: 224
<212> TYPE: PRT
<213> ORGANISM: Artificial Sequence
<220> FEATURE:
<223> OTHER INFORMATION: Fc region xELL T366S, L368A, Y407V hole

<400> SEQUENCE: 65

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
        50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
            195                 200                 205

Leu His Asn His Tyr Thr Gln Lys Ser Leu Ser Leu Ser Pro Gly Lys
        210                 215                 220

<210> SEQ ID NO 66
<211> LENGTH: 224
```

<212> TYPE: PRT
<213> ORGANISM: Artificial Sequence
<220> FEATURE:
<223> OTHER INFORMATION: Fc region xELL H435R, T366S, L368A, Y407V hole

<400> SEQUENCE: 66

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Gly Lys
    210                 215                 220

<210> SEQ ID NO 67
<211> LENGTH: 224
<212> TYPE: PRT
<213> ORGANISM: Artificial Sequence
<220> FEATURE:
<223> OTHER INFORMATION: Fc region xELL M252Y and M428V (YV) T366S,
      L368A, Y407V hole

<400> SEQUENCE: 67

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr

```
            100                 105                 110
Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Gly Lys
    210                 215                 220

<210> SEQ ID NO 68
<211> LENGTH: 224
<212> TYPE: PRT
<213> ORGANISM: Artificial Sequence
<220> FEATURE:
<223> OTHER INFORMATION: Fc region xELL M252Y and M428L (YL) T366S,
      L368A, Y407V hole

<400> SEQUENCE: 68

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
            85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Leu His Glu Ala
        195                 200                 205

Leu His Asn His Tyr Thr Gln Lys Ser Leu Ser Leu Ser Pro Gly Lys
    210                 215                 220

<210> SEQ ID NO 69
<211> LENGTH: 224
```

```
<212> TYPE: PRT
<213> ORGANISM: Artificial Sequence
<220> FEATURE:
<223> OTHER INFORMATION: Fc region xELL M252Y, M428L, H435R (YLR) T366S,
      L368A, Y407V hole

<400> SEQUENCE: 69
```

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Leu His Glu Ala
        195                 200                 205

Leu His Asn Arg Tyr Thr Gln Lys Ser Leu Ser Leu Ser Pro Gly Lys
    210                 215                 220

```
<210> SEQ ID NO 70
<211> LENGTH: 224
<212> TYPE: PRT
<213> ORGANISM: Artificial Sequence
<220> FEATURE:
<223> OTHER INFORMATION: Fc region xELL M252Y, M428V, H435R (YVR) T366S,
      L368A, Y407V hole

<400> SEQUENCE: 70
```

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

```
Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro Gly Lys
            210                 215                 220

<210> SEQ ID NO 71
<211> LENGTH: 227
<212> TYPE: PRT
<213> ORGANISM: Artificial Sequence
<220> FEATURE:
<223> OTHER INFORMATION: Fc region H435R

<400> SEQUENCE: 71

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225
```

<210> SEQ ID NO 72
<211> LENGTH: 227
<212> TYPE: PRT
<213> ORGANISM: Artificial Sequence
<220> FEATURE:
<223> OTHER INFORMATION: Fc region M252Y and M428V (YV)

<400> SEQUENCE: 72

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro Gly Lys
225
```

<210> SEQ ID NO 73
<211> LENGTH: 227
<212> TYPE: PRT
<213> ORGANISM: Artificial Sequence
<220> FEATURE:
<223> OTHER INFORMATION: Fc region M252Y and M428L (YL)

<400> SEQUENCE: 73

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225

<210> SEQ ID NO 74
<211> LENGTH: 227
<212> TYPE: PRT
<213> ORGANISM: Artificial Sequence
<220> FEATURE:
<223> OTHER INFORMATION: Fc region M252Y, M428L, H435R (YLR)

<400> SEQUENCE: 74

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205
```

His Glu Ala Leu His Asn Arg Tyr Thr Gln Lys Ser Leu Ser Leu Ser
    210                 215                 220

Pro Gly Lys
225

<210> SEQ ID NO 75
<211> LENGTH: 227
<212> TYPE: PRT
<213> ORGANISM: Artificial Sequence
<220> FEATURE:
<223> OTHER INFORMATION: Fc region M252Y, M428V, H435R (YVR)

<400> SEQUENCE: 75

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro Gly Lys
225

<210> SEQ ID NO 76
<211> LENGTH: 227
<212> TYPE: PRT
<213> ORGANISM: Artificial Sequence
<220> FEATURE:
<223> OTHER INFORMATION: Fc region S354C T366W knob

<400> SEQUENCE: 76

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

```
              35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Cys Arg Asp Glu Leu Thr Lys Asn Gln Val Ser
                130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
                210                 215                 220
Pro Gly Lys
225

<210> SEQ ID NO 77
<211> LENGTH: 227
<212> TYPE: PRT
<213> ORGANISM: Artificial Sequence
<220> FEATURE:
<223> OTHER INFORMATION: Fc region H435R S354C T366W knob

<400> SEQUENCE: 77

Asp Lys Thr His Thr Cys Pro Pro Cys Pro Ala Pro Glu Leu Leu Gly
 1               5                  10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
                35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Cys Arg Asp Glu Leu Thr Lys Asn Gln Val Ser
                130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
```

165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225

<210> SEQ ID NO 78
<211> LENGTH: 227
<212> TYPE: PRT
<213> ORGANISM: Artificial Sequence
<220> FEATURE:
<223> OTHER INFORMATION: Fc region M252Y and M428L (YL) S354C T366W knob

<400> SEQUENCE: 78

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225

<210> SEQ ID NO 79
<211> LENGTH: 227
<212> TYPE: PRT
<213> ORGANISM: Artificial Sequence
<220> FEATURE:
<223> OTHER INFORMATION: Fc region M252Y, M428L, H435R (YLR) S354C T366W
      knob

<400> SEQUENCE: 79

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                      55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Leu
            195                 200                 205

His Glu Ala Leu His Asn Arg Tyr Thr Gln Lys Ser Leu Ser Leu Ser
    210                 215                 220

Pro Gly Lys
225

<210> SEQ ID NO 80
<211> LENGTH: 227
<212> TYPE: PRT
<213> ORGANISM: Artificial Sequence
<220> FEATURE:
<223> OTHER INFORMATION: Fc region M252Y, M428V, H435R (YVR) S354C T366W
      knob

<400> SEQUENCE: 80

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                      55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val

```
            115                 120                 125
Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Val
                195                 200                 205

His Glu Ala Leu His Asn Arg Tyr Thr Gln Lys Ser Leu Ser Leu Ser
    210                 215                 220

Pro Gly Lys
225

<210> SEQ ID NO 81
<211> LENGTH: 227
<212> TYPE: PRT
<213> ORGANISM: Artificial Sequence
<220> FEATURE:
<223> OTHER INFORMATION: Fc region T366S, L368A, Y407V hole

<400> SEQUENCE: 81

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
    210                 215                 220

Pro Gly Lys
225
```

-continued

<210> SEQ ID NO 82
<211> LENGTH: 227
<212> TYPE: PRT
<213> ORGANISM: Artificial Sequence
<220> FEATURE:
<223> OTHER INFORMATION: Fc region H435R, T366S, L368A, Y407V hole

<400> SEQUENCE: 82

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225

<210> SEQ ID NO 83
<211> LENGTH: 227
<212> TYPE: PRT
<213> ORGANISM: Artificial Sequence
<220> FEATURE:
<223> OTHER INFORMATION: Fc region M252Y and M428V (YV) T366S, L368A,
    Y407V hole

<400> SEQUENCE: 83

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro Gly Lys
225

<210> SEQ ID NO 84
<211> LENGTH: 227
<212> TYPE: PRT
<213> ORGANISM: Artificial Sequence
<220> FEATURE:
<223> OTHER INFORMATION: Fc region M252Y and M428L (YL) T366S, L368A,
      Y407V hole

<400> SEQUENCE: 84

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Leu
```

```
                195                 200                 205

His Glu Ala Leu His Asn His Tyr Thr Gln Lys Ser Leu Ser Leu Ser
        210                 215                 220

Pro Gly Lys
225

<210> SEQ ID NO 85
<211> LENGTH: 227
<212> TYPE: PRT
<213> ORGANISM: Artificial Sequence
<220> FEATURE:
<223> OTHER INFORMATION: Fc region M252Y, M428L, H435R (YLR) T366S,
      L368A, Y407V hole

<400> SEQUENCE: 85

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn Arg Tyr Thr Gln Lys Ser Leu Ser Leu Ser
    210                 215                 220

Pro Gly Lys
225

<210> SEQ ID NO 86
<211> LENGTH: 199
<212> TYPE: PRT
<213> ORGANISM: Artificial Sequence
<220> FEATURE:
<223> OTHER INFORMATION: CLEC12a-ECD

<400> SEQUENCE: 86

Thr Leu Lys Ile Glu Met Lys Lys Met Asn Lys Leu Gln Asn Ile Ser
1               5                   10                  15

Glu Glu Leu Gln Arg Asn Ile Ser Leu Gln Leu Met Ser Asn Met Asn
            20                  25                  30
```

Ile Ser Asn Lys Ile Arg Asn Leu Ser Thr Thr Leu Gln Thr Ile Ala
            35                  40                  45

Thr Lys Leu Cys Arg Glu Leu Tyr Ser Lys Glu Gln Glu His Lys Cys
 50                  55                  60

Lys Pro Cys Pro Arg Arg Trp Ile Trp His Lys Asp Ser Cys Tyr Phe
 65                  70                  75                  80

Leu Ser Asp Asp Val Gln Thr Trp Gln Glu Ser Lys Met Ala Cys Ala
                85                  90                  95

Ala Gln Asn Ala Ser Leu Leu Lys Ile Asn Asn Lys Asn Ala Leu Glu
            100                 105                 110

Phe Ile Lys Ser Gln Ser Arg Ser Tyr Asp Tyr Trp Leu Gly Leu Ser
            115                 120                 125

Pro Glu Glu Asp Ser Thr Arg Gly Met Arg Val Asp Asn Ile Ile Asn
            130                 135                 140

Ser Ser Ala Trp Val Ile Arg Asn Ala Pro Asp Leu Asn Asn Met Tyr
145                 150                 155                 160

Cys Gly Tyr Ile Asn Arg Leu Tyr Val Gln Tyr Tyr His Cys Thr Tyr
                165                 170                 175

Lys Lys Arg Met Ile Cys Glu Lys Met Ala Asn Pro Val Gln Leu Gly
            180                 185                 190

Ser Thr Tyr Phe Arg Glu Ala
            195

<210> SEQ ID NO 87
<211> LENGTH: 442
<212> TYPE: PRT
<213> ORGANISM: Artificial Sequence
<220> FEATURE:
<223> OTHER INFORMATION: mFc-CLEC12a-ECD

<400> SEQUENCE: 87

Leu Glu Val Leu Phe Gln Gly Pro Gly Ser Pro Pro Leu Lys Glu Cys
1               5                   10                  15

Pro Pro Cys Ala Ala Pro Asp Leu Leu Gly Gly Pro Ser Val Phe Ile
            20                  25                  30

Phe Pro Pro Lys Ile Lys Asp Val Leu Met Ile Ser Leu Ser Pro Met
            35                  40                  45

Val Thr Cys Val Val Val Asp Val Ser Glu Asp Asp Pro Asp Val Gln
 50                  55                  60

Ile Ser Trp Phe Val Asn Asn Val Glu Val His Thr Ala Gln Thr Gln
 65                  70                  75                  80

Thr His Arg Glu Asp Tyr Asn Ser Thr Leu Arg Val Val Ser Ala Leu
                85                  90                  95

Pro Ile Gln His Gln Asp Trp Met Ser Gly Lys Glu Phe Lys Cys Lys
            100                 105                 110

Val Asn Asn Arg Ala Leu Pro Ser Pro Ile Glu Lys Thr Ile Ser Lys
            115                 120                 125

Pro Arg Gly Pro Val Arg Ala Pro Gln Val Tyr Val Leu Pro Pro Pro
            130                 135                 140

Ala Glu Glu Met Thr Lys Lys Glu Phe Ser Leu Thr Cys Met Ile Thr
145                 150                 155                 160

Gly Phe Leu Pro Ala Glu Ile Ala Val Asp Trp Thr Ser Asn Gly Arg
                165                 170                 175

Thr Glu Gln Asn Tyr Lys Asn Thr Ala Thr Val Leu Asp Ser Asp Gly
            180                 185                 190

```
Ser Tyr Phe Met Tyr Ser Lys Leu Arg Val Gln Lys Ser Thr Trp Glu
        195                 200                 205

Arg Gly Ser Leu Phe Ala Cys Ser Val Val His Glu Gly Leu His Asn
    210                 215                 220

His Leu Thr Thr Lys Thr Ile Ser Arg Ser Leu Gly Lys Gly Gly Thr
225                 230                 235                 240

Gly Gly Ser Thr Leu Lys Ile Glu Met Lys Lys Met Asn Lys Leu Gln
                245                 250                 255

Asn Ile Ser Glu Glu Leu Gln Arg Asn Ile Ser Leu Gln Leu Met Ser
            260                 265                 270

Asn Met Asn Ile Ser Asn Lys Ile Arg Asn Leu Ser Thr Thr Leu Gln
        275                 280                 285

Thr Ile Ala Thr Lys Leu Cys Arg Glu Leu Tyr Ser Lys Glu Gln Glu
    290                 295                 300

His Lys Cys Lys Pro Cys Pro Arg Arg Trp Ile Trp His Lys Asp Ser
305                 310                 315                 320

Cys Tyr Phe Leu Ser Asp Asp Val Gln Thr Trp Gln Glu Ser Lys Met
                325                 330                 335

Ala Cys Ala Ala Gln Asn Ala Ser Leu Leu Lys Ile Asn Asn Lys Asn
            340                 345                 350

Ala Leu Glu Phe Ile Lys Ser Gln Ser Arg Ser Tyr Asp Tyr Trp Leu
        355                 360                 365

Gly Leu Ser Pro Glu Glu Asp Ser Thr Arg Gly Met Arg Val Asp Asn
    370                 375                 380

Ile Ile Asn Ser Ser Ala Trp Val Ile Arg Asn Ala Pro Asp Leu Asn
385                 390                 395                 400

Asn Met Tyr Cys Gly Tyr Ile Asn Arg Leu Tyr Val Gln Tyr Tyr His
                405                 410                 415

Cys Thr Tyr Lys Lys Arg Met Ile Cys Glu Lys Met Ala Asn Pro Val
            420                 425                 430

Gln Leu Gly Ser Thr Tyr Phe Arg Glu Ala
        435                 440

<210> SEQ ID NO 88
<211> LENGTH: 119
<212> TYPE: PRT
<213> ORGANISM: Artificial Sequence
<220> FEATURE:
<223> OTHER INFORMATION: MB11 K version

<400> SEQUENCE: 88

Gln Val Gln Leu Gln Gln Ser Gly Gly Gly Leu Val Gln Pro Gly Gly
1               5                   10                  15

Ser Leu Arg Leu Ser Cys Val Ala Ser Gly Phe Leu Phe Ser Ile Tyr
            20                  25                  30

Asp Met Asn Trp Tyr Arg Gln Ala Pro Gly Lys Glu Arg Glu Trp Ile
        35                  40                  45

Ala Gly Ile Thr Asn Asn Gly Tyr Ser Thr Ala Tyr Thr Asp Ser Val
    50                  55                  60

Gln Gly Arg Phe Thr Ile Ser Arg Asp Asn Ala Lys Asn Thr Ile Tyr
65                  70                  75                  80

Leu Gln Met Thr Ser Leu Lys Pro Glu Asp Thr Ala Val Tyr Tyr Cys
                85                  90                  95

His Ala Asp Leu Thr Lys Cys Tyr Asp Gly Glu Tyr Ala Trp Gly Gln
            100                 105                 110
```

```
Gly Thr Gln Val Thr Val Lys
        115

<210> SEQ ID NO 89
<211> LENGTH: 118
<212> TYPE: PRT
<213> ORGANISM: Artificial Sequence
<220> FEATURE:
<223> OTHER INFORMATION: MC02 K version

<400> SEQUENCE: 89

Gln Val Gln Leu Val Gln Ser Gly Gly Leu Ala Gln Pro Gly Gly
1               5                   10                  15

Ser Leu Arg Leu Ser Cys Thr Ala Ser Gly Phe Thr Phe Arg Ile Asn
                20                  25                  30

Asp Met Gly Trp Tyr Arg Gln Ala Pro Gly Lys Glu Cys Glu Met Val
                35                  40                  45

Ala Gly Ile Ser Asn Asn Gly Phe Ser Thr Ala Tyr Ala Asp Ser Val
                50                  55                  60

Lys Gly Arg Phe Thr Ile Ser Arg Asp Asn Ala Lys Asn Thr Val Ser
65                  70                  75                  80

Leu Gln Met Asp Ser Leu Lys Ser Glu Asp Thr Ala Val Tyr Tyr Cys
                    85                  90                  95

His Arg Thr Asp Asp Gly Ala Ala His Ala Cys Ser Arg Gly Gln Gly
                100                 105                 110

Thr Gln Val Thr Val Lys
        115

<210> SEQ ID NO 90
<211> LENGTH: 120
<212> TYPE: PRT
<213> ORGANISM: Artificial Sequence
<220> FEATURE:
<223> OTHER INFORMATION: MC06 K version

<400> SEQUENCE: 90

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
                20                  25                  30

Asp Met Asn Trp Tyr Arg Gln Thr Pro Gly Lys Glu Arg Glu Trp Val
                35                  40                  45

Ala Gly Ile Ser Asn Asn Gly Phe Ser Thr Ala Tyr Ala Gly Ser Val
                50                  55                  60

Lys Gly Arg Phe Thr Ile Ser Arg Asp Asn Ala Glu Asn Thr Val Tyr
65                  70                  75                  80

Leu Gln Met Asn Ser Leu Lys Ser Glu Asp Thr Ala Val Tyr Tyr Cys
                    85                  90                  95

Asn Leu Asp Val His Gly Arg Val Gly Ala Gly Asn Gly Asp Tyr Trp Gly
                100                 105                 110

Gln Gly Thr Gln Val Thr Val Lys
        115                 120

<210> SEQ ID NO 91
<211> LENGTH: 111
<212> TYPE: PRT
<213> ORGANISM: Artificial Sequence
<220> FEATURE:
<223> OTHER INFORMATION: ME02 K version
```

<400> SEQUENCE: 91

Gln Val Gln Leu Gln Gln Ser Gly Gly Leu Val Gln Val Gly Gly
1               5                   10                  15

Ser Gln Arg Leu Ser Cys Ala Ala Ser Gly Arg Thr Phe Glu Tyr Asp
            20                  25                  30

Asp Met Val Trp Phe Arg Gln Ala Pro Gly Lys Glu Arg Glu Glu Val
        35                  40                  45

Ala Gly Ile Ser Trp Ser Gly Ser Ile Tyr Tyr Ala Asp Ser Val
    50                  55                  60

Lys Gly Arg Phe Ser Ile Ser Arg Asp Asn Ala Lys Asn Thr Val Tyr
65                  70                  75                  80

Leu Glu Met Asn Arg Leu Lys Pro Glu Asp Thr Ala Val Tyr Tyr Cys
                85                  90                  95

Asn Val Gly Ser Tyr Trp Gly Gln Gly Thr Gln Val Thr Val Lys
            100                 105                 110

<210> SEQ ID NO 92
<211> LENGTH: 128
<212> TYPE: PRT
<213> ORGANISM: Artificial Sequence
<220> FEATURE:
<223> OTHER INFORMATION: ME06 K version

<400> SEQUENCE: 92

Gln Val Gln Leu Val Gln Ser Gly Gly Gly Leu Val Gln Ala Gly Gly
1               5                   10                  15

Ser Leu Arg Leu Ser Cys Val Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Ile Ser Asn Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu His Val Asn Ser Leu Asn Pro Glu Asp Thr Ala Val Tyr Tyr Cys
                85                  90                  95

Ala Leu Arg Glu Gly Leu Pro Leu Leu Leu Asp Ser Leu Trp Arg Gln
            100                 105                 110

Pro Val Glu Tyr Asp Tyr Trp Gly Gln Gly Thr Gln Val Thr Val Lys
        115                 120                 125

<210> SEQ ID NO 93
<211> LENGTH: 115
<212> TYPE: PRT
<213> ORGANISM: Artificial Sequence
<220> FEATURE:
<223> OTHER INFORMATION: MH07 K version

<400> SEQUENCE: 93

Gln Val Gln Leu Val Gln Ser Gly Gly Gly Leu Val Gln Pro Gly Gly
1               5                   10                  15

Ser Leu Arg Leu Ser Cys Val Ala Ser Gly Leu Leu Phe Ser Ile Tyr
            20                  25                  30

Asp Met Asn Trp Tyr Arg Gln Ala Pro Gly Lys Glu Arg Glu Trp Ile
        35                  40                  45

Ala Gly Ile Thr Asn Asn Gly Tyr Ser Thr Ala Tyr Thr Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

His Thr Asp Glu Trp Gly Arg Glu Tyr Trp Gly Gln Gly Thr Gln Val
            100                 105                 110

Thr Val Lys
        115

<210> SEQ ID NO 94
<211> LENGTH: 120
<212> TYPE: PRT
<213> ORGANISM: Artificial Sequence
<220> FEATURE:
<223> OTHER INFORMATION: hzMB11v13 KP version

<400> SEQUENCE: 94

Glu Val Gln Leu Val Glu Ser Gly Gly Glu Val Gln Pro Gly Gly
1               5                   10                  15

Ser Leu Arg Leu Ser Cys Ala Ala Ser Gly Phe Leu Phe Ser Ile Tyr
            20                  25                  30

Asp Met Asn Trp Tyr Arg Gln Ala Pro Gly Lys Glu Arg Glu Trp Val
            35                  40                  45

Ala Gly Ile Thr Asn Asn Gly Tyr Ser Thr Ala Tyr Ala Glu Ser Val
            50                  55                  60

Lys Gly Arg Phe Thr Ile Ser Arg Asp Asn Ala Lys Asn Thr Ile Tyr
65                  70                  75                  80

Leu Gln Met Ser Ser Leu Arg Ala Glu Asp Thr Ala Val Tyr Tyr Cys
            85                  90                  95

His Ala Asp Leu Thr Lys Ala Tyr Asp Val Glu Tyr Ala Trp Gly Gln
            100                 105                 110

Gly Thr Leu Val Thr Val Lys Pro
        115                 120

<210> SEQ ID NO 95
<211> LENGTH: 119
<212> TYPE: PRT
<213> ORGANISM: Artificial Sequence
<220> FEATURE:
<223> OTHER INFORMATION: hzMC02v6 KP version

<400> SEQUENCE: 95

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Ile Asn
            20                  25                  30

Asp Met Gly Trp Tyr Arg Gln Ala Pro Gly Lys Glu Cys Glu Met Val
            35                  40                  45

Ala Gly Ile Ser Asn Asn Gly Phe Ser Thr Ala Tyr Ala Glu Ser Val
            50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
            85                  90                  95

His Arg Thr Asp Glu Gly Ala Ala His Ala Cys Ser Arg Gly Gln Gly
            100                 105                 110

Thr Leu Val Thr Val Lys Pro

-continued

```
              115

<210> SEQ ID NO 96
<211> LENGTH: 121
<212> TYPE: PRT
<213> ORGANISM: Artificial Sequence
<220> FEATURE:
<223> OTHER INFORMATION: hzMC06v2 KP version

<400> SEQUENCE: 96

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Val Tyr
            20                  25                  30

Asp Met Asn Trp Tyr Arg Gln Ala Pro Gly Lys Glu Arg Glu Trp Val
        35                  40                  45

Ser Gly Ile Ser Asn Asn Gly Phe Ser Thr Ala Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Asn Leu Asp Val His Gly Arg Val Gly Ala Gln Gly Asp Tyr Trp Gly
            100                 105                 110

Gln Gly Thr Leu Val Thr Val Lys Pro
        115                 120

<210> SEQ ID NO 97
<211> LENGTH: 112
<212> TYPE: PRT
<213> ORGANISM: Artificial Sequence
<220> FEATURE:
<223> OTHER INFORMATION: hzME02v4 KP version

<400> SEQUENCE: 97

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Thr Phe Glu Tyr Asp
            20                  25                  30

Asp Met Val Trp Phe Arg Gln Ala Pro Gly Lys Glu Arg Glu Val
        35                  40                  45

Ala Gly Ile Ser Trp Ser Gly Ser Ile Tyr Tyr Ala Glu Ser Val
    50                  55                  60

Lys Gly Arg Phe Ser Ile Ser Arg Asp Asn Ala Lys Asn Thr Val Tyr
65                  70                  75                  80

Leu Glu Met Asn Arg Leu Lys Pro Glu Asp Thr Ala Val Tyr Tyr Cys
                85                  90                  95

Asn Val Gly Ser Tyr Trp Gly Gln Gly Thr Leu Val Thr Val Lys Pro
            100                 105                 110

<210> SEQ ID NO 98
<211> LENGTH: 129
<212> TYPE: PRT
<213> ORGANISM: Artificial Sequence
<220> FEATURE:
<223> OTHER INFORMATION: hzME06v16 KP version

<400> SEQUENCE: 98

Glu Val Gln Leu Val Glu Ser Gly Gly Gly Glu Val Gln Pro Gly Gly
1               5                   10                  15
```

```
Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
            35                  40                  45

Ser Thr Ile Ser Ser Ser Asp Gly Ser Thr Tyr Tyr Ala Glu Ser Val
 50                      55                  60

Lys Gly Arg Phe Thr Ile Ser Arg Asp Asn Ala Lys Asn Thr Val Tyr
 65                  70                  75                  80

Leu Gln Met Ser Ser Leu Arg Ala Glu Asp Thr Ala Val Tyr Tyr Cys
                 85                  90                  95

Ala Leu Arg Glu Gly Leu Pro Leu Leu Leu Asp Thr Leu Trp Arg Gln
            100                 105                 110

Pro Val Glu Tyr Asp Tyr Trp Gly Gln Gly Thr Gln Val Thr Val Lys
            115                 120                 125

Pro

<210> SEQ ID NO 99
<211> LENGTH: 116
<212> TYPE: PRT
<213> ORGANISM: Artificial Sequence
<220> FEATURE:
<223> OTHER INFORMATION: hzMH07v3 KP version

<400> SEQUENCE: 99

Glu Val Gln Leu Val Glu Ser Gly Gly Gly Val Gln Pro Gly Gly
 1               5                  10                  15

Ser Leu Arg Leu Ser Cys Ala Ala Ser Gly Leu Leu Phe Ser Ile Tyr
            20                  25                  30

Asp Met Asn Trp Tyr Arg Gln Ala Pro Gly Lys Glu Arg Glu Trp Val
            35                  40                  45

Ala Gly Ile Thr Asn Asn Gly Tyr Ser Thr Ala Tyr Ala Glu Ser Val
 50                      55                  60

Lys Gly Arg Phe Thr Ile Ser Arg Asp Asn Ala Lys Asn Thr Val Tyr
 65                  70                  75                  80

Leu Gln Met Ser Ser Leu Arg Ala Glu Asp Thr Ala Val Tyr Tyr Cys
                 85                  90                  95

His Thr Asp Glu Trp Gly Arg Glu Tyr Trp Gly Gln Gly Thr Leu Val
            100                 105                 110

Thr Val Lys Pro
        115
```